(12) United States Patent
Barber et al.

(10) Patent No.: US 9,394,561 B2
(45) Date of Patent: Jul. 19, 2016

(54) CYCLIC PEPTIDE PRODUCTION

(71) Applicant: National Research Council of Canada, Ottawa (CA)

(72) Inventors: Carla Jann Siobhan Barber, Saskatoon (CA); Darwin Wilfred Reed, Saskatoon (CA); Janet Anne Condie, Saskatoon (CA); Sheila Diniwe Sherin Chiwocha, Saskatoon (CA); Patrick Smithers Covello, Saskatoon (CA)

(73) Assignee: National Research Council of Canada, Ottawa, Onatrio ( * ) Notice: Subject to any disclaimer, the term of this patent is extended or adjusted under 35 U.S.C. 154(b) by 0 days.

(21) Appl. No.: 14/363,561

(22) PCT Filed: Dec. 7, 2012

(86) PCT No.: PCT/CA2012/001130
§ 371 (c)(1),
(2) Date: Jun. 6, 2014

(87) PCT Pub. No.: WO2013/082708
PCT Pub. Date: Jun. 13, 2013

(65) Prior Publication Data
US 2014/0363844 A1    Dec. 11, 2014

Related U.S. Application Data

(60) Provisional application No. 61/640,115, filed on Apr. 30, 2012, provisional application No. 61/567,844, filed on Dec. 7, 2011.

(51) Int. Cl.
C12P 21/06 (2006.01)
C07K 7/64 (2006.01)
C07K 14/415 (2006.01)
C12N 15/63 (2006.01)
C12N 15/82 (2006.01)
C12N 9/00 (2006.01)
C12N 9/48 (2006.01)

(52) U.S. Cl.
CPC . *C12P 21/06* (2013.01); *C07K 7/64* (2013.01); *C07K 14/415* (2013.01); *C12N 9/48* (2013.01); *C12N 9/93* (2013.01); *C12N 15/63* (2013.01); *C12N 15/8257* (2013.01)

(58) Field of Classification Search
None
See application file for complete search history.

(56) References Cited

FOREIGN PATENT DOCUMENTS

| CN | 102174530 | 9/2011 |
| WO | 2007103739 | 9/2007 |
| WO | 2010130030 A1 | 11/2010 |
| WO | 2011005598 A1 | 1/2011 |

OTHER PUBLICATIONS

Lee et al., Using Marine Natural Products to Discover a Protease that Catalyzes Peptide Macrocyclization of Diverse Substrates., J. Am. Chem. Soc., (2009), vol. 131 (6), pp. 2122-2124.*

(Continued)

*Primary Examiner* — Alexander Kim
(74) *Attorney, Agent, or Firm* — Laura Catherine Eckenswiller

(57) ABSTRACT

An enzyme useful for producing cyclic peptides from linear peptide precursors and a gene encoding the enzyme are described. The enzyme is particularly useful for producing segetalins from linear presegetalin precursors. The linear presegetalin precursors may be derived from other linear presegetalin precursors farther upstream in the biosynthetic synthesis of the segetalin.

9 Claims, 10 Drawing Sheets

(56) References Cited

OTHER PUBLICATIONS

Schmidt et al., Patellamide A and C biosynthesis by a microcin-like pathway in Prochloron didemni, the cyanobacterial symbiont of Lissoclinum patella., Proc Natl Acad Sci U S A. (2005), vol. 102(20), pp. 7315-7320.*

Q52QJ1-patG from Prochloron (last viewed on Mar. 11, 2015).*

GenBank AGL51088.1 (May 18, 2013).*

Jaillon et al., The grapevine genome sequence suggests ancestral hexaploidization in major angiosperm phyla., Nature (2007), vol. 449, pp. 463-467.*

Guo et al., Protein tolerance to random amino acid change, 2004, Proc. Natl. Acad. Sci. USA 101: 9205-9210.*

Lazar et al., Transforming Growth Factor α: Mutation of Aspartic Acid 47 and Leucine 48 Results in Different Biological Activity, 1988, Mol. Cell. Biol. 8:1247-1252.*

Hill et al., Functional Analysis of conserved Histidines in ADP-Glucose Pyrophosphorylase from *Escherichia coli*, 1998, Biochem. Biophys. Res. Comm. 244:573-577.*

Wacey et al., Disentangling the perturbational effects of amino acid substitutions in the DNA-binding domain of p53., Hum Genet, 1999, vol. 104, pp. 15-22.*

Easton et al. (Glycosylation of Proteins-Structure, Function and Analysis., Life Science Technical Bulletin (Jul. 2011), Issue 48, pp. 1-5.*

* cited by examiner

A class

| | | | | | |
|---|---|---|---|---|---|
| MSPILAHDVVKPQ | GVPVWA | FQ | AKDVENASAPV | A1 | (SEQ ID NO: 3) |
| MSPILAHDVVKPQ | GVAWA | FQ | AKDVENASAPV | B1 | (SEQ ID NO: 4) |
| MSPIFAHDVVNPQ | GLSFA | FP | AKDAENASSPV | D1 | (SEQ ID NO: 5) |
| MSPIFAHDVVKPQ | GLSFA | FP | AKDAENASSPV | D2 | (SEQ ID NO: 6) |
| MSPILAHDVVKPQ | GLSFA | FP | AKDAENASSPV | D3 | (SEQ ID NO: 7) |
| MSPIFVHEVVKPQ | GVKYA | FQ | PKDSENASAPV | G1 | (SEQ ID NO: 8) |
| MSPIFAHDIVKPK | GYRFS | FQ | AKDAENASAPV | H1 | (SEQ ID NO: 9) |
| MSPILALDRYKPE | GRVKA | FQ | AKDAENASAPV | K1 | (SEQ ID NO: 10) |
| MSPILSHDVVKPQ | GLPGWP | FQ | AKDVENASAPV | L1 | (SEQ ID NO: 11) |

F class

| | | | | | |
|---|---|---|---|---|---|
| MATSFQFDGLKPS | FSASYSSKP | IQ | TQVSNGMDNASAPV | F1 | (SEQ ID NO: 12) |
| MATSFQLDGLKPS | FGTHGLPAP | IQ | VPNGMDDACAPM | J1 | (SEQ ID NO: 13) |

Fig. 1

```
ATGGCGACTTCAGGATTCTCGAAACCGCTGCATTATCCACCGGTTCGCCGCGACGAGACCGTCGTCGA
CGATTACTTTGGCGTTAAAGTCGCTGATCCTTACCGTTGGCTAGAGGATCCGAATTCGGAGGAGACGA
AGGAATTCGTGGATAATCAGGAAAAACTCGCGAATTCAGTGCTTGAAGAATGCGAGTTGATAGACAAA
TTCAAGCAAAAAATCATTGATTTTGTTAATTTTCCGCGGTGTGGCGTGCCGTTTAGGCGTGCCAACAA
GTATTTTCACTTCTATAATTCCGGCCTTCAAGCGCAAAATGTTTTTCAGATGCAGGATGATTTGGACG
GAAAGCCAGAGGTGCTATACGATCCTAATCTTAGAGAGGGTGGACGATCCGGTTTGAGCCTGTATTCT
GTAAGCGAGGATGCCAAATATTTTGCATTTGGTATACATTCAGGTTTGACTGAATGGGTGACTATCAA
AATATTGAAAACTGAAGACCGGAGCTATTTACCCGACACTTTAGAGTGGGTGAAGTTTAGTCCTGCCA
TCTGGACTCATGACAATAAAGGATTTTTCTATTGCCCGTATCCACCCCTCAAGGAAGGAGAAGATCAT
ATGACTCGTTCTGCCGTCAATCAAGAGGCAAGATATCATTTTTGGGTACTGACCAGTCCGAAGATAT
TTTGTTGTGGAGAGACCTTGAGAACCCCGCACATCACTTAAAGTGCCAGATAACTGATGACGGAAAGT
ATTTTCTTCTCTACATTCTGGACGGCTGTGATGATGCGAACAAAGTATACTGTTTGGATTTAACAAAG
CTGCCTAATGGGCTTGAAAGTTTCCGGGGAGAGAAGACTCAGCTCCTTTCATGAAGCTTATCGATAG
TTTTGATGCATCATATACAGCCATTGCTAATGATGGCTCTGTGTTTACATTTCAAACTAATAAGGATG
CGCCCAGAAAAAAGTTAGTTCGTGTTGATTTGAATAATCCCAGTGTATGGACTGATCTCGTTCCAGAG
TCGAAGAAGGATTTGCTTGAATCAGCACATGCTGTCAATGAAAACCAGCTTATTCTCCGTTACCTAAG
TGATGTCAAACATGTTCTGGAGATTAGAGATCTTGAAAGTGGCGCTCTGCAGCATCGCTTACCCATCG
ACATTGGATCTGTTGATGGTATTACTGCACGACGAAGAGACAGTGTCGTGTTTTTTAAGTTTACAAGT
ATCCTGACTCCTGGCATTGTTTATCAATGTGATTTGAAAAATGATCCTACACAGTTGAAGATCTTCAG
AGAAAGTGTGGTCCCTGATTTTGATCGTTCCGAGTTTGAAGTTAAGCAGGTTTTTGTGCCCAGCAAAG
ATGGCACAAAGATACCAATATTTATAGCGGCAAGAAAGGGAATATCTTTGGATGGATCACACCCATGT
GAAATGCATGGTTATGGCGGGTTTGGCATAAACATGATGCCAACTTTTTCCGCCAGTCGCATAGTATT
TCTGAAGCACCTAGGTGGCGTCTTCTGCTTGGCTAATATCCGAGGTGGGGGTGAATACGAGAGGAAT
GGCATAAGGCAGGATTTCGCGATAAGAAGCAAAACGTTTTTGATGACTTCATCTCTGCAGCCGAGTAT
CTTATTTCCAGTGGCTATACCAAGGCTAGAAGGTGGCTATTGAAGGTGGTAGTAATGGTGGCCTTCT
CGTTGCTGCTTGTATTAATCAGAGACCAGACCTTTTCGGTTGTGCTGAACAAACTGTGGTGTTATGG
ACATGCTTCGATTCCATAAATTTACCCTTGGTTATCTTTGGACGGGAGACTATGGATGCTCCGACAAA
GAGGAAGAATTCAAATGGCTTATCAAGTACTCACCGATTCATAACGTGAGGAGGCCATGGGAACAACC
AGGGAACGAAGAGACACAATACCCTGCTACTATGATATTGACAGCTGATCACGACGATCGTGTCGTGC
CACTGCACTCGTTTAAATTGCTGGCTACTATGCAGCATGTTTTGTGCACAAGTTTGGAGGACAGCCCT
CAGAAGAATCCAATAATTGCTCGGATTCAGCGCAAAGCTGCACATTACGGACGTGCCACAATGACCCA
GATTGCTGAAGTAGCTGATCGGTATGGCTTTATGGCAAAGGCGCTTGAAGCTCCTTGGATAGAC
```

Fig. 4 – SEQ ID NO: 1

```
MATSGFSKPLHYPPVRRDETVVDDYFGVKVADPYRWLEDPNSEETKEFVDNQEKLANSVLEECELIDK
FKQKIIDFVNFPRCGVPFRRANKYFHFYNSGLQAQNVFQMQDDLDGKPEVLYDPNLREGGRSGLSLYS
VSEDAKYFAFGIHSGLTEWVTIKILKTEDRSYLPDTLEWVKFSPAIWTHDNKGFFYCPYPPLKEGEDH
MTRSAVNQEARYHFLGTDQSEDILLWRDLENPAHHLKCQITDDGKYFLLYILDGCDDANKVYCLDLTK
LPNGLESFRGREDSAPFMKLIDSFDASYTAIANDGSVFTFQTNKDAPRKKLVRVDLNNPSVWTDLVPE
SKKDLLESAHAVNENQLILRYLSDVKHVLEIRDLESGALQHRLPIDIGSVDGITARRRDSVVFFKFTS
ILTPGIVYQCDLKNDPTQLKIFRESVVPDFDRSEFEVKQVFVPSKDGTKIPIFIAARKGISLDGSHPC
EMHGYGGFGINMMPTFSASRIVFLKHLGGVFCLANIRGGGEYGEEWHKAGFRDKKQNVFDDFISAAEY
LISSGYTKARRVAIEGGSNGGLLVAACINQRPDLFGCAEANCGVMDMLRFHKFTLGYLWTGDYGCSDK
EEEFKWLIKYSPIHNVRRPWEQPGNEETQYPATMILTADHDDRVVPLHSFKLLATMQHVLCTSLEDSP
QKNPIIARIQRKAAHYGRATMTQIAEVADRYGFMAKALEAPWID
```

Fig. 5 – SEQ ID NO: 2

SEQUENCE LISTING

```
<160> NUMBER OF SEQ ID NOS: 77

<210> SEQ ID NO 1
<211> LENGTH: 2172
<212> TYPE: DNA
<213> ORGANISM: Saponaria vaccaria

<400> SEQUENCE: 1
atggcgactt caggattctc gaaaccgctg cattatccac cggttcgccg cgacgagacc      60
gtcgtcgacg attactttgg cgttaaagtc gctgatcctt accgttggct agaggatccg     120
aattcggagg agacgaagga attcgtggat aatcaggaaa aactcgcgaa ttcagtgctt     180
gaagaatgcg agttgataga caaattcaag caaaaaatca ttgattttgt taattttccg     240
cggtgtggcg tgccgtttag gcgtgccaac aagtattttc acttctataa ttccggcctt     300
caagcgcaaa atgtttttca gatgcaggat gatttggacg gaaagccaga ggtgctatac     360
gatcctaatc ttagagaggg tggacgatcc ggtttgagcc tgtattctgt aagcgaggat     420
gccaaatatt ttgcatttgg tatacattca ggtttgactg aatgggtgac tatcaaaata     480
ttgaaaactg aagaccggag ctatttaccc gacactttag agtgggtgaa gtttagtcct     540
gccatctgga ctcatgacaa taaaggattt ttctattgcc cgtatccacc cctcaaggaa     600
ggagaagatc atatgactcg ttctgccgtc aatcaagagg caagatatca tttttttgggt     660 actgaccagt ccgaagatat tttgttgtgg agagaccttg agaacccgc acatcactta      720 aagtgccaga taactgatga cggaaagtat tttcttctct acattctgga cggctgtgat     780
gatgcgaaca aagtatactg tttggattta acaaagctgc ctaatgggct tgaaagtttc     840 cggggagag aagactcagc tcctttcatg aagcttatcg atagttttga tgcatcatat      900
```

```
acagccattg ctaatgatgg ctctgtgttt acatttcaaa ctaataagga tgcgcccaga    960
aaaaagttag ttcgtgttga tttgaataat cccagtgtat ggactgatct cgttccagag   1020
tcgaagaagg atttgcttga atcagcacat gctgtcaatg aaaaccagct tattctccgt   1080
tacctaagtg atgtcaaaca tgttctggag attagagatc ttgaaagtgg cgctctgcag   1140
catcgcttac ccatcgacat tggatctgtt gatggtatta ctgcacgacg aagagacagt   1200
gtcgtgtttt ttaagtttac aagtatcctg actcctggca ttgtttatca atgtgatttg   1260
aaaaatgatc ctacacagtt gaagatcttc agagaaagtg tggtccctga ttttgatcgt   1320
tccgagtttg aagttaagca ggttttgtg cccagcaaag atggcacaaa gataccaata   1380
tttatagcgg caagaaaggg aatatctttg gatggatcac acccatgtga atgcatggt    1440
tatggcgggt ttggcataaa catgatgcca acttttccg ccagtcgcat agtatttctg    1500
aagcacctag gtggcgtctt ctgcttggct aatatccgag gtggggtga atacggagag    1560
gaatggcata aggcaggatt tcgcgataag aagcaaaacg ttttgatga cttcatctct    1620
gcagccgagt atcttatttc cagtggctat accaaggcta aagagtggc tattgaaggt    1680
ggtagtaatg gtggccttct cgttgctgct tgtattaatc agagaccaga ccttttcggt   1740
tgtgctgaag caaactgtgg tgttatggac atgcttcgat ccataaaatt taccccttggt  1800
tatctttgga cgggagacta tggatgctcc gacaaagagg aagaattcaa atggcttatc   1860
aagtactcac cgattcataa cgtgaggagg ccatgggaac aaccagggaa cgaagagaca   1920
caatacctgc tactatgat attgacagct gatcacgacg atcgtgtcgt gccactgcac    1980
tcgtttaaat tgctggctac tatgcagcat gtttttgtgca caagtttgga ggacagccct  2040
cagaagaatc caataattgc tcggattcag cgcaaagctg cacattacgg acgtgccaca   2100
atgacccaga ttgctgaagt agctgatcgg tatggcttta tggcaaaggc gcttgaagct   2160
ccttggatag ac                                                      2172

<210> SEQ ID NO 2
<211> LENGTH: 724
<212> TYPE: PRT
<213> ORGANISM: Saponaria vaccaria

<400> SEQUENCE: 2

Met Ala Thr Ser Gly Phe Ser Lys Pro Leu His Tyr Pro Pro Val Arg
1               5                   10                  15

Arg Asp Glu Thr Val Val Asp Asp Tyr Phe Gly Val Lys Val Ala Asp
                20                  25                  30

Pro Tyr Arg Trp Leu Glu Asp Pro Asn Ser Glu Glu Thr Lys Glu Phe
            35                  40                  45

Val Asp Asn Gln Glu Lys Leu Ala Asn Ser Val Leu Glu Glu Cys Glu
        50                  55                  60

Leu Ile Asp Lys Phe Lys Gln Lys Ile Ile Asp Phe Val Asn Phe Pro
65                  70                  75                  80

Arg Cys Gly Val Pro Phe Arg Arg Ala Asn Lys Tyr Phe His Phe Tyr
                85                  90                  95

Asn Ser Gly Leu Gln Ala Gln Asn Val Phe Gln Met Gln Asp Asp Leu
            100                 105                 110

Asp Gly Lys Pro Glu Val Leu Tyr Asp Pro Asn Leu Arg Glu Gly Gly
        115                 120                 125

Arg Ser Gly Leu Ser Leu Tyr Ser Val Ser Glu Asp Ala Lys Tyr Phe
    130                 135                 140
```

-continued

```
Ala Phe Gly Ile His Ser Gly Leu Thr Glu Trp Val Thr Ile Lys Ile
145                 150                 155                 160

Leu Lys Thr Glu Asp Arg Ser Tyr Leu Pro Asp Thr Leu Glu Trp Val
                165                 170                 175

Lys Phe Ser Pro Ala Ile Trp Thr His Asp Asn Lys Gly Phe Phe Tyr
                    180                 185                 190

Cys Pro Tyr Pro Pro Leu Lys Glu Gly Glu Asp His Met Thr Arg Ser
                        195                 200                 205

Ala Val Asn Gln Glu Ala Arg Tyr His Phe Leu Gly Thr Asp Gln Ser
210                 215                 220

Glu Asp Ile Leu Leu Trp Arg Asp Leu Glu Asn Pro Ala His His Leu
225                 230                 235                 240

Lys Cys Gln Ile Thr Asp Asp Gly Lys Tyr Phe Leu Leu Tyr Ile Leu
                    245                 250                 255

Asp Gly Cys Asp Asp Ala Asn Lys Val Tyr Cys Leu Asp Leu Thr Lys
                260                 265                 270

Leu Pro Asn Gly Leu Glu Ser Phe Arg Gly Arg Glu Asp Ser Ala Pro
            275                 280                 285

Phe Met Lys Leu Ile Asp Ser Phe Asp Ala Ser Tyr Thr Ala Ile Ala
290                 295                 300

Asn Asp Gly Ser Val Phe Thr Phe Gln Thr Asn Lys Asp Ala Pro Arg
305                 310                 315                 320

Lys Lys Leu Val Arg Val Asp Leu Asn Asn Pro Ser Val Trp Thr Asp
                325                 330                 335

Leu Val Pro Glu Ser Lys Lys Asp Leu Glu Ser Ala His Ala Val
                340                 345                 350

Asn Glu Asn Gln Leu Ile Leu Arg Tyr Leu Ser Asp Val Lys His Val
                355                 360                 365

Leu Glu Ile Arg Asp Leu Glu Ser Gly Ala Leu Gln His Arg Leu Pro
370                 375                 380

Ile Asp Ile Gly Ser Val Asp Gly Ile Thr Ala Arg Arg Arg Asp Ser
385                 390                 395                 400

Val Val Phe Phe Lys Phe Thr Ser Ile Leu Thr Pro Gly Ile Val Tyr
                405                 410                 415

Gln Cys Asp Leu Lys Asn Asp Pro Thr Gln Leu Lys Ile Phe Arg Glu
                420                 425                 430

Ser Val Val Pro Asp Phe Asp Arg Ser Glu Phe Glu Val Lys Gln Val
                435                 440                 445

Phe Val Pro Ser Lys Asp Gly Thr Lys Ile Pro Ile Phe Ile Ala Ala
            450                 455                 460

Arg Lys Gly Ile Ser Leu Asp Gly Ser His Pro Cys Glu Met His Gly
465                 470                 475                 480

Tyr Gly Gly Phe Gly Ile Asn Met Met Pro Thr Phe Ser Ala Ser Arg
                    485                 490                 495

Ile Val Phe Leu Lys His Leu Gly Gly Val Phe Cys Leu Ala Asn Ile
                500                 505                 510

Arg Gly Gly Gly Glu Tyr Gly Glu Glu Trp His Lys Ala Gly Phe Arg
                515                 520                 525

Asp Lys Lys Gln Asn Val Phe Asp Asp Phe Ile Ser Ala Ala Glu Tyr
            530                 535                 540

Leu Ile Ser Ser Gly Tyr Thr Lys Ala Arg Arg Val Ala Ile Glu Gly
545                 550                 555                 560
```

```
Gly Ser Asn Gly Gly Leu Leu Val Ala Ala Cys Ile Asn Gln Arg Pro
            565                 570                 575

Asp Leu Phe Gly Cys Ala Glu Ala Asn Cys Gly Val Met Asp Met Leu
        580                 585                 590

Arg Phe His Lys Phe Thr Leu Gly Tyr Leu Trp Thr Gly Asp Tyr Gly
            595                 600                 605

Cys Ser Asp Lys Glu Glu Phe Lys Trp Leu Ile Lys Tyr Ser Pro
    610                 615                 620

Ile His Asn Val Arg Arg Pro Trp Glu Gln Pro Gly Asn Glu Glu Thr
625                 630                 635                 640

Gln Tyr Pro Ala Thr Met Ile Leu Thr Ala Asp His Asp Arg Val
                645                 650                 655

Val Pro Leu His Ser Phe Lys Leu Leu Ala Thr Met Gln His Val Leu
                660                 665                 670

Cys Thr Ser Leu Glu Asp Ser Pro Gln Lys Asn Pro Ile Ile Ala Arg
            675                 680                 685

Ile Gln Arg Lys Ala Ala His Tyr Gly Arg Ala Thr Met Thr Gln Ile
        690                 695                 700

Ala Glu Val Ala Asp Arg Tyr Gly Phe Met Ala Lys Ala Leu Glu Ala
705                 710                 715                 720

Pro Trp Ile Asp

<210> SEQ ID NO 3
<211> LENGTH: 32
<212> TYPE: PRT
<213> ORGANISM: Saponaria vaccaria

<400> SEQUENCE: 3

Met Ser Pro Ile Leu Ala His Asp Val Val Lys Pro Gln Gly Val Pro
1               5                   10                  15

Val Trp Ala Phe Gln Ala Lys Asp Val Glu Asn Ala Ser Ala Pro Val
            20                  25                  30

<210> SEQ ID NO 4
<211> LENGTH: 31
<212> TYPE: PRT
<213> ORGANISM: Saponaria vaccaria

<400> SEQUENCE: 4

Met Ser Pro Ile Leu Ala His Asp Val Val Lys Pro Gln Gly Val Ala
1               5                   10                  15

Trp Ala Phe Gln Ala Lys Asp Val Glu Asn Ala Ser Ala Pro Val
            20                  25                  30

<210> SEQ ID NO 5
<211> LENGTH: 31
<212> TYPE: PRT
<213> ORGANISM: Saponaria vaccaria

<400> SEQUENCE: 5

Met Ser Pro Ile Phe Ala His Asp Val Val Asn Pro Gln Gly Leu Ser
1               5                   10                  15

Phe Ala Phe Pro Ala Lys Asp Ala Glu Asn Ala Ser Ser Pro Val
            20                  25                  30

<210> SEQ ID NO 6
<211> LENGTH: 31
<212> TYPE: PRT
<213> ORGANISM: Saponaria vaccaria
```

```
<400> SEQUENCE: 6

Met Ser Pro Ile Phe Ala His Asp Val Val Lys Pro Gln Gly Leu Ser
1               5                   10                  15

Phe Ala Phe Pro Ala Lys Asp Ala Glu Asn Ala Ser Ser Pro Val
            20                  25                  30

<210> SEQ ID NO 7
<211> LENGTH: 31
<212> TYPE: PRT
<213> ORGANISM: Saponaria vaccaria

<400> SEQUENCE: 7

Met Ser Pro Ile Leu Ala His Asp Val Val Lys Pro Gln Gly Leu Ser
1               5                   10                  15

Phe Ala Phe Pro Ala Lys Asp Ala Glu Asn Ala Ser Ser Pro Val
            20                  25                  30

<210> SEQ ID NO 8
<211> LENGTH: 31
<212> TYPE: PRT
<213> ORGANISM: Saponaria vaccaria

<400> SEQUENCE: 8

Met Ser Pro Ile Phe Val His Glu Val Val Lys Pro Gln Gly Val Lys
1               5                   10                  15

Tyr Ala Phe Gln Pro Lys Asp Ser Glu Asn Ala Ser Ala Pro Val
            20                  25                  30

<210> SEQ ID NO 9
<211> LENGTH: 31
<212> TYPE: PRT
<213> ORGANISM: Saponaria vaccaria

<400> SEQUENCE: 9

Met Ser Pro Ile Phe Ala His Asp Ile Val Lys Pro Lys Gly Tyr Arg
1               5                   10                  15

Phe Ser Phe Gln Ala Lys Asp Ala Glu Asn Ala Ser Ala Pro Val
            20                  25                  30

<210> SEQ ID NO 10
<211> LENGTH: 31
<212> TYPE: PRT
<213> ORGANISM: Saponaria vaccaria

<400> SEQUENCE: 10

Met Ser Pro Ile Leu Ala Leu Asp Arg Tyr Lys Pro Glu Gly Arg Val
1               5                   10                  15

Lys Ala Phe Gln Ala Lys Asp Ala Glu Asn Ala Ser Ala Pro Val
            20                  25                  30

<210> SEQ ID NO 11
<211> LENGTH: 32
<212> TYPE: PRT
<213> ORGANISM: Saponaria vaccaria

<400> SEQUENCE: 11

Met Ser Pro Ile Leu Ser His Asp Val Val Lys Pro Gln Gly Leu Pro
1               5                   10                  15

Gly Trp Pro Phe Gln Ala Lys Asp Val Glu Asn Ala Ser Ala Pro Val
            20                  25                  30
```

<210> SEQ ID NO 12
<211> LENGTH: 38
<212> TYPE: PRT
<213> ORGANISM: Saponaria vaccaria

<400> SEQUENCE: 12

Met Ala Thr Ser Phe Gln Phe Asp Gly Leu Lys Pro Ser Phe Ser Ala
1               5                   10                  15

Ser Tyr Ser Ser Lys Pro Ile Gln Thr Gln Val Ser Asn Gly Met Asp
            20                  25                  30

Asn Ala Ser Ala Pro Val
        35

<210> SEQ ID NO 13
<211> LENGTH: 36
<212> TYPE: PRT
<213> ORGANISM: Saponaria vaccaria

<400> SEQUENCE: 13

Met Ala Thr Ser Phe Gln Leu Asp Gly Leu Lys Pro Ser Phe Gly Thr
1               5                   10                  15

His Gly Leu Pro Ala Pro Ile Gln Val Pro Asn Gly Met Asp Asp Ala
            20                  25                  30

Cys Ala Pro Met
        35

<210> SEQ ID NO 14
<211> LENGTH: 6
<212> TYPE: PRT
<213> ORGANISM: Saponaria vaccaria
<220> FEATURE:
<221> NAME/KEY: MISC_FEATURE
<222> LOCATION: (1)..(6)
<223> OTHER INFORMATION: Cyclic peptide

<400> SEQUENCE: 14

Gly Val Pro Val Trp Ala
1               5

<210> SEQ ID NO 15
<211> LENGTH: 19
<212> TYPE: PRT
<213> ORGANISM: Saponaria vaccaria

<400> SEQUENCE: 15

Gly Val Pro Val Trp Ala Phe Gln Ala Lys Asp Val Glu Asn Ala Ser
1               5                   10                  15

Ala Pro Val

<210> SEQ ID NO 16
<211> LENGTH: 13
<212> TYPE: PRT
<213> ORGANISM: Saponaria vaccaria

<400> SEQUENCE: 16

Met Ser Pro Ile Leu Ala His Asp Val Val Lys Pro Gln
1               5                   10

<210> SEQ ID NO 17
<211> LENGTH: 12
<212> TYPE: PRT
<213> ORGANISM: Saponaria vaccaria -continued

```
<400> SEQUENCE: 17

Ser Pro Ile Leu Ala His Asp Val Val Lys Pro Gln
1               5                   10

<210> SEQ ID NO 18
<211> LENGTH: 13
<212> TYPE: PRT
<213> ORGANISM: Saponaria vaccaria

<400> SEQUENCE: 18

Phe Gln Ala Lys Asp Val Glu Asn Ala Ser Ala Pro Val
1               5                   10

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
atggcgactt caggattctc g                                               21

<210> SEQ ID NO 20
<211> LENGTH: 25
<212> TYPE: DNA
<213> ORGANISM: Artificial Sequence
<220> FEATURE:
<223> OTHER INFORMATION: Primer

<400> SEQUENCE: 20
tcagtctatc caaggagctt caagc                                           25

<210> SEQ ID NO 21
<211> LENGTH: 2178
<212> TYPE: DNA
<213> ORGANISM: Silene vulgaris

<400> SEQUENCE: 21
atggcttcct ccgccttctc caaacccttg aactaccctc ccgtccgccg tgacgaaacc      60
gtcgtcaatg attacttcgg cgtcaaagtc gccgatcctt accgttggct agaggatcag     120
gaaggggaag agacgataga gtttgtagat aatcaagtga aattggctga ttcagtgctt     180
gaagaatgtg agttgagaga taagatcaag cagaaaatca cggatcttgt caattttccg     240
cgttgcggtg tgccgtttaa gcgtgctgac aagtattttc atttttataa ttctggactt     300
caagctcaaa atgtgcttca tatgcaggat gatttggacg gaaagccaga ggtgctatat     360
gatcctaacc ttagagaagg tggaagatct ggattgcacc agtatgctgt aagcgaggat     420
gccaaatatc tcgcgtttgg tataaattca ggttttttcag aatggttgac tatcaaagtg     480
atgagaattg aagaccggag tgttttacct gactctttat catgggtgaa gtttagtggt     540
attcactgga cacatgacag taagggattt ttcttttccc catatccacc cgccactgaa     600
ggactagaag ttgggatgaa aactaattct agcttcaatc aggagttgag gtatcatttt     660
cttggtactg atgagtctga agacgttctg tgctggagag accggaaaaa ccccacacat     720
cacttgaaat ctgatttaac tgctgacgga aagtatttac tactctatat atcagcgggt     780
tgtgatgcaa cgaacaaagt ttactatatg gatttaacaa ctttgcctaa tgggcttgaa     840
ggtttgcgtg ggggaaagga cttgcttcct ttcaaaaggc ttattgatga gtttgatgca     900
acgtatacag ctattgctaa tgatggctct gtgtttactt tcctaaccaa caaggatgct    960
```

-continued

```
ccaagaaata agatagttcg tgtagatttg aataatccag acatatggac tgaggtgatt      1020
ccagagtcta agaaggatgt gcttgaatca gcacacgctg ttaatggaaa ccaacttctt      1080
gtccgttacc taagtgatgt caaacatatt ctggaggtta gagatctaga gagtggctct      1140
ctactgcatc gcttacccgt cgacctcgga gttattgatg gaatcactgc acgaccacaa      1200
gatagtgttg tgttttcaa gttacaagc ttcctgactc ctaccataat ttatcagtgt        1260
gatttgaagg aagattctcc acagttaaag attttccgag aaagtgttgt tcctgaattt      1320
gaccgttccg agtttgaggt taaacaggtg tttgtatcag ccaaagatgg cacaaagata      1380
ccaatgttca tagtggcaag gaagggaata tctttggatg gatcacaccc atgtgaacta      1440
catggttatg gcgggttcag catatctata aaaccatttt tttccgccag tcgcattgta      1500
attttgaagc accttgatgc cgtcttctgc gtggctaata tccgaggtgg tggtgaatat      1560
ggagaggaat ggcaccaagc aggatggcgt gaaaagaagc agattgtttt tgatgacttc      1620
atctcttcag ctgagtatct tgtttctagt ggctataccc agcctcaaaa gttgagtatt      1680
gaaggaggca gtaatggtgg cctgcttgtt gctgcttgta ttaatcagag accagacctt      1740
tttggttgcg ctcaggccaa ttgcggtgta atggacatgc ttcgattcca taaatttacc      1800
ctcggttatc tttggacatc ggattatggt tgctccgaga aagaggaaga ttttaactgg      1860
cttataaagt actcaccgat acataatgtg aggaggccat gggagcactc aaagaatcca      1920
cagttacaat accctgctgt tatgatactg acagctgatc atgatgatcg tgtggtgcct      1980
cttcactcct tcaaactgct ggctactttg cagcatgttc tttgcacaag tttagaggac      2040
tcccctcaga aaaatccaat aattgctcga attgagcgca aagcatcaca ctgtgggcgt      2100
gcgacgatga agcagattga tgaagctgca gatcggtacg cctttatggc caaggcgctt      2160
agagccactt ggactgat                                                    2178
```

<210> SEQ ID NO 22
<211> LENGTH: 726
<212> TYPE: PRT
<213> ORGANISM: Silene vulgaris

<400> SEQUENCE: 22

```
Met Ala Ser Ser Ala Phe Ser Lys Pro Leu Asn Tyr Pro Pro Val Arg
1               5                   10                  15

Arg Asp Glu Thr Val Val Asn Asp Tyr Phe Gly Val Lys Val Ala Asp
                20                  25                  30

Pro Tyr Arg Trp Leu Glu Asp Gln Glu Gly Glu Thr Ile Glu Phe
            35                  40                  45

Val Asp Asn Gln Val Lys Leu Ala Asp Ser Val Leu Glu Glu Cys Glu
    50                  55                  60

Leu Arg Asp Lys Ile Lys Gln Lys Ile Thr Asp Leu Val Asn Phe Pro
65                  70                  75                  80

Arg Cys Gly Val Pro Phe Lys Arg Ala Asp Lys Tyr Phe His Phe Tyr
                85                  90                  95

Asn Ser Gly Leu Gln Ala Gln Asn Val Leu His Met Gln Asp Asp Leu
            100                 105                 110

Asp Gly Lys Pro Glu Val Leu Tyr Asp Pro Asn Leu Arg Glu Gly Gly
        115                 120                 125

Arg Ser Gly Leu His Gln Tyr Ala Val Ser Glu Asp Ala Lys Tyr Leu
    130                 135                 140

Ala Phe Gly Ile Asn Ser Gly Phe Ser Glu Trp Leu Thr Ile Lys Val
```

-continued

```
            145                 150                 155                 160
        Met Arg Ile Glu Asp Arg Ser Val Leu Pro Asp Ser Leu Ser Trp Val
                            165                 170                 175
        Lys Phe Ser Gly Ile His Trp Thr His Asp Ser Lys Gly Phe Phe Phe
                            180                 185                 190
        Ser Pro Tyr Pro Pro Ala Thr Glu Gly Leu Glu Val Gly Met Lys Thr
                            195                 200                 205
        Asn Ser Ser Phe Asn Gln Glu Leu Arg Tyr His Phe Leu Gly Thr Asp
                            210                 215                 220
        Glu Ser Glu Asp Val Leu Cys Trp Arg Asp Pro Glu Asn Pro Thr His
        225                 230                 235                 240
        His Leu Lys Ser Asp Leu Thr Ala Asp Gly Lys Tyr Leu Leu Leu Tyr
                            245                 250                 255
        Ile Ser Ala Gly Cys Asp Ala Thr Asn Lys Val Tyr Tyr Met Asp Leu
                            260                 265                 270
        Thr Thr Leu Pro Asn Gly Leu Glu Gly Leu Arg Gly Gly Lys Asp Leu
                            275                 280                 285
        Leu Pro Phe Lys Arg Leu Ile Asp Glu Phe Asp Ala Thr Tyr Thr Ala
        290                 295                 300
        Ile Ala Asn Asp Gly Ser Val Phe Thr Phe Leu Thr Asn Lys Asp Ala
        305                 310                 315                 320
        Pro Arg Asn Lys Ile Val Arg Val Asp Leu Asn Asn Pro Asp Ile Trp
                            325                 330                 335
        Thr Glu Val Ile Pro Glu Ser Lys Lys Asp Val Leu Glu Ser Ala His
                            340                 345                 350
        Ala Val Asn Gly Asn Gln Leu Leu Val Arg Tyr Leu Ser Asp Val Lys
                            355                 360                 365
        His Ile Leu Glu Val Arg Asp Leu Glu Ser Gly Ser Leu Leu His Arg
                            370                 375                 380
        Leu Pro Val Asp Leu Gly Val Ile Asp Gly Ile Thr Ala Arg Pro Gln
        385                 390                 395                 400
        Asp Ser Val Val Phe Phe Lys Phe Thr Ser Phe Leu Thr Pro Thr Ile
                            405                 410                 415
        Ile Tyr Gln Cys Asp Leu Lys Glu Asp Ser Pro Gln Leu Lys Ile Phe
                            420                 425                 430
        Arg Glu Ser Val Val Pro Glu Phe Asp Arg Ser Glu Phe Glu Val Lys
                            435                 440                 445
        Gln Val Phe Val Ser Ala Lys Asp Gly Thr Lys Ile Pro Met Phe Ile
                            450                 455                 460
        Val Ala Arg Lys Gly Ile Ser Leu Asp Gly Ser His Pro Cys Glu Leu
        465                 470                 475                 480
        His Gly Tyr Gly Gly Phe Ser Ile Ser Ile Lys Pro Phe Phe Ser Ala
                            485                 490                 495
        Ser Arg Ile Val Ile Leu Lys His Leu Asp Ala Val Phe Cys Val Ala
                            500                 505                 510
        Asn Ile Arg Gly Gly Gly Glu Tyr Gly Glu Glu Trp His Gln Ala Gly
                            515                 520                 525
        Trp Arg Glu Lys Lys Gln Ile Val Phe Asp Asp Phe Ile Ser Ser Ala
                            530                 535                 540
        Glu Tyr Leu Val Ser Ser Gly Tyr Thr Gln Pro Gln Lys Leu Ser Ile
        545                 550                 555                 560
        Glu Gly Gly Ser Asn Gly Gly Leu Leu Val Ala Ala Cys Ile Asn Gln
                            565                 570                 575
```

```
Arg Pro Asp Leu Phe Gly Cys Ala Gln Ala Asn Cys Val Met Asp
                580             585                 590

Met Leu Arg Phe His Lys Phe Thr Leu Gly Tyr Leu Trp Thr Ser Asp
        595                 600                 605

Tyr Gly Cys Ser Glu Lys Glu Glu Asp Phe Asn Trp Leu Ile Lys Tyr
    610                 615                 620

Ser Pro Ile His Asn Val Arg Arg Pro Trp Glu His Ser Lys Asn Pro
625                 630                 635                 640

Gln Leu Gln Tyr Pro Ala Val Met Ile Leu Thr Ala Asp His Asp Asp
                645                 650                 655

Arg Val Val Pro Leu His Ser Phe Lys Leu Leu Ala Thr Leu Gln His
                660                 665                 670

Val Leu Cys Thr Ser Leu Glu Asp Ser Pro Gln Lys Asn Pro Ile Ile
            675                 680                 685

Ala Arg Ile Glu Arg Lys Ala Ser His Cys Gly Arg Ala Thr Met Lys
        690                 695                 700

Gln Ile Asp Glu Ala Ala Asp Arg Tyr Ala Phe Met Ala Lys Ala Leu
705                 710                 715                 720

Arg Ala Thr Trp Thr Asp
                725

<210> SEQ ID NO 23
<211> LENGTH: 2169
<212> TYPE: DNA
<213> ORGANISM: Dianthus superbus

<400> SEQUENCE: 23
atggcgtcct gtggattcac taaacccttg cattatccta cggcacgccg tgacgaaacc      60
gtcgtcgacg attacttcgg cctcaaagtc gccgatcctt accgctggct cgaggatcgg     120
gattcggaag agacgaagaa attcgtggag gatcaagtga agtttactga ttcagtgctt     180
gaggaatgcg agttgatcgg caaagtcaag caaaagatca tagattatgt tagttttccg     240
cgttggagtg tgccgcttag gcgtgccaac aaatattttc acttctataa ctctggactt     300
caatcgcaaa atgtttatcg gatgcaggat ggtttggacg aaagccaga ggtgatatgt      360 gatcctaatc ttagagaaga cggacgaact ggcttgagcg tgtattctgt aagcgaggat     420
gccaaatatt ttgcatttgg tatagcagaa ggctttacta atggctcac gattagagta      480 atgagaacgg aagaccggag tatgttaccc gactgtttaa ccgaggtgaa atttactact     540
gttcattgga cgcatgataa taaaggattt ttctattgtg catatccgcc ctcgaggaa      600 ggacaagatc atatggttca tgctagcatc agtcaagagg cgagatatca ttatcttggt     660
acagaccagt ctgaagatat tttgtgctgg aaagatcctg aaaacccca caccacttc      720 aggagctatt ttactgatga cggaaagtat tttgttctct acattttaga gggatgtgat     780
aagaagaaca agtatactg tctggattta caaagctac ctaacgggcc tgaaagtctc      840
cgagggagag aaggctcagc tccttcata aaacttgtgg atagttttga tgcatcgtat     900
acagtcattg ctaatgatga ttctgtgttt acactcctaa ctgataagga tgcaaaaaga     960
tgtaagttag ttcgtgttga tttgaataat ccgagcgtgt ggactgatgt gattccggag    1020
tccaaggact tgcttgaatc agcacatgca gtcaacggaa accagcttct tcttcgttac    1080
ctacgtgatg tcaaacatgt acttgagctt agggatctcg aaagtggctc tctactacat    1140 agcatacccca tagacattgg agctgttgat ggtattaatg cacgacgagg agacagtatc    1200
```

```
gtgtttttta ggtttacaag catcctgact cctggcataa tttatcaatg tgatttgaaa    1260
aatgatccta cacagttaaa tatcttcaga gaaagtcttg tccctgggtt tgaccgttct    1320
gagttcgagg ttaaacaggt ttttgtgcct ggcaaagatg aacaaagat accagcattc     1380 atagcagcaa gaaagggaat atctttggat ggatcacatc catgtgaaat gcatggctac    1440
ggcggatatg ccataatat gatgccaact ttttccgcca gtcgcttagt atttttgaag     1500
caccttggtg gcgtcttctg tttggctaat attcgaggtg gtggtgaata tggagttgac    1560
tggcataaag caggagcccg tgaaaacaag caaaccagtt ttgatgactt catctcctca    1620
gctgagtttc ttgtttctag tggctacagc gcacctaaaa aaatttgtat cgaaggtgga    1680
agtaacgggg gccttctcat tgctgtttgt attactcaga gaccagacct gttcggttgt    1740
gccgagccga actgtggtcc tatggacatg cttcgattcc ataaatttac gcttggttat    1800
ctttggactg atgaatatgg taaccccgac aatgaggaag agttcaactg gcttatcaag    1860
tactcaccgc tacacaacgt gaggagacca tgggaacagc cagggcatga acagacacaa    1920
taccccgcga ctatgataat aacggctgat catgatgatc gtgtggtgcc aatgcattcg    1980
tataaaatga ttgctactat gcagcatgtt ctgtgcacaa gcttagagaa cagccctcag    2040
aagtatccaa taatttgtcg cattcagcgc aaagcttcac attacggacg ttccacaatg    2100
gttcagatcg ctgaggtagc agatcggtat ggctttatgg caaaggcgct taacgctact    2160
tggacagac                                                             2169

<210> SEQ ID NO 24
<211> LENGTH: 723
<212> TYPE: PRT
<213> ORGANISM: Dianthus superbus

<400> SEQUENCE: 24

Met Ala Ser Cys Gly Phe Thr Lys Pro Leu His Tyr Pro Thr Ala Arg
1               5                   10                  15

Arg Asp Glu Thr Val Val Asp Asp Tyr Phe Gly Leu Lys Val Ala Asp
            20                  25                  30

Pro Tyr Arg Trp Leu Glu Asp Arg Asp Ser Glu Glu Thr Lys Lys Phe
        35                  40                  45

Val Glu Asp Gln Val Lys Phe Thr Asp Ser Val Leu Glu Glu Cys Glu
    50                  55                  60

Leu Ile Gly Lys Val Lys Gln Lys Ile Ile Asp Tyr Val Ser Phe Pro
65                  70                  75                  80

Arg Trp Ser Val Pro Leu Arg Arg Ala Asn Lys Tyr Phe His Phe Tyr
                85                  90                  95

Asn Ser Gly Leu Gln Ser Gln Asn Val Tyr Arg Met Gln Asp Gly Leu
            100                 105                 110

Asp Gly Lys Pro Glu Val Ile Cys Asp Pro Asn Leu Arg Glu Asp Gly
        115                 120                 125

Arg Thr Gly Leu Ser Val Tyr Ser Val Ser Glu Asp Ala Lys Tyr Phe
    130                 135                 140

Ala Phe Gly Ile Ala Glu Gly Phe Thr Glu Trp Leu Thr Ile Arg Val
145                 150                 155                 160

Met Arg Thr Glu Asp Arg Ser Met Leu Pro Asp Cys Leu Thr Glu Val
                165                 170                 175

Lys Phe Thr Thr Val His Trp Thr His Asp Asn Lys Gly Phe Phe Tyr
            180                 185                 190

Cys Ala Tyr Pro Pro Leu Glu Glu Gly Gln Asp His Met Val His Ala
```

```
                195                 200                 205
Ser Ile Ser Gln Glu Ala Arg Tyr His Tyr Leu Gly Thr Asp Gln Ser
210                 215                 220

Glu Asp Ile Leu Cys Trp Lys Asp Pro Glu Asn Pro Thr His His Phe
225                 230                 235                 240

Arg Ser Tyr Phe Thr Asp Asp Gly Lys Tyr Phe Val Leu Tyr Ile Leu
                245                 250                 255

Glu Gly Cys Asp Lys Lys Asn Lys Val Tyr Cys Leu Asp Leu Thr Lys
            260                 265                 270

Leu Pro Asn Gly Pro Glu Ser Leu Arg Gly Arg Glu Gly Ser Ala Pro
        275                 280                 285

Phe Ile Lys Leu Val Asp Ser Phe Asp Ala Ser Tyr Thr Val Ile Ala
290                 295                 300

Asn Asp Asp Ser Val Phe Thr Leu Leu Thr Asp Lys Ala Lys Ala Arg
305                 310                 315                 320

Cys Lys Leu Val Arg Val Asp Leu Asn Asn Pro Ser Val Trp Thr Asp
                325                 330                 335

Val Ile Pro Glu Ser Lys Asp Leu Leu Glu Ser Ala His Ala Val Asn
            340                 345                 350

Gly Asn Gln Leu Leu Leu Arg Tyr Leu Arg Asp Val Lys His Val Leu
        355                 360                 365

Glu Leu Arg Asp Leu Glu Ser Gly Ser Leu Leu His Ser Ile Pro Ile
370                 375                 380

Asp Ile Gly Ala Val Asp Gly Ile Asn Ala Arg Arg Gly Asp Ser Ile
385                 390                 395                 400

Val Phe Phe Arg Phe Thr Ser Ile Leu Thr Pro Gly Ile Ile Tyr Gln
                405                 410                 415

Cys Asp Leu Lys Asn Asp Pro Thr Gln Leu Asn Ile Phe Arg Glu Ser
            420                 425                 430

Leu Val Pro Gly Phe Asp Arg Ser Glu Phe Glu Val Lys Gln Val Phe
        435                 440                 445

Val Pro Gly Lys Asp Gly Thr Lys Ile Pro Ala Phe Ile Ala Ala Arg
450                 455                 460

Lys Gly Ile Ser Leu Asp Gly Ser His Pro Cys Glu Met His Gly Tyr
465                 470                 475                 480

Gly Gly Tyr Gly His Asn Met Met Pro Thr Phe Ser Ala Ser Arg Leu
                485                 490                 495

Val Phe Leu Lys His Leu Gly Val Phe Cys Leu Ala Asn Ile Arg
            500                 505                 510

Gly Gly Gly Glu Tyr Gly Val Asp Trp His Lys Ala Gly Ala Arg Glu
        515                 520                 525

Asn Lys Gln Thr Ser Phe Asp Asp Phe Ile Ser Ser Ala Glu Phe Leu
530                 535                 540

Val Ser Ser Gly Tyr Ser Ala Pro Lys Lys Ile Cys Ile Glu Gly Gly
545                 550                 555                 560

Ser Asn Gly Gly Leu Leu Ile Ala Val Cys Ile Thr Gln Arg Pro Asp
                565                 570                 575

Leu Phe Gly Cys Ala Glu Pro Asn Cys Gly Pro Met Asp Met Leu Arg
            580                 585                 590

Phe His Lys Phe Thr Leu Gly Tyr Leu Trp Thr Asp Glu Tyr Gly Asn
        595                 600                 605

Pro Asp Asn Glu Glu Glu Phe Asn Trp Leu Ile Lys Tyr Ser Pro Leu
610                 615                 620
```

His Asn Val Arg Arg Pro Trp Glu Gln Pro Gly His Glu Gln Thr Gln
625                 630                 635                 640

Tyr Pro Ala Thr Met Ile Ile Thr Ala Asp His Asp Arg Val Val
            645                 650                 655

Pro Met His Ser Tyr Lys Met Ile Ala Thr Met Gln His Val Leu Cys
        660                 665                 670

Thr Ser Leu Glu Asn Ser Pro Gln Lys Tyr Pro Ile Ile Cys Arg Ile
            675                 680                 685

Gln Arg Lys Ala Ser His Tyr Gly Arg Ser Thr Met Val Gln Ile Ala
        690                 695                 700

Glu Val Ala Asp Arg Tyr Gly Phe Met Ala Lys Ala Leu Asn Ala Thr
705                 710                 715                 720

Trp Thr Asp

<210> SEQ ID NO 25
<211> LENGTH: 2175
<212> TYPE: DNA
<213> ORGANISM: Dianthus superbus

<400> SEQUENCE: 25
atggcggtgt cctgtggatt caccaaaacc ttgcattatc ctcccgtacg ccgtgacgaa      60
accgtcgtcg acgattattt cggcctcaaa atcgccgatc cttaccgctg gcttgaggat     120
ctgaattcag aagagacaaa gaaattcgtg gatgatcaag tgaagtttac agagtcggtg     180
cttgaagaat gcgagttgat tggcaaagtc aagcagaaaa tcatagatta tgtcagtttt     240
ccgcgttgga gtgtgccgct taggcgtgcc aacaaatatt tccacttcta taactccggc     300
cttcaatcgc aaaatgtgta tcggatgcag gatggtttgg acggaaagcc agaggtggta     360
tatgatccta accttagaga aggggaaga actggtttga ccctgtattc tgtaagcgag     420
gatgccaatt attttgcatt tggtatagct gaaggcttta ctgaatggct cacgattaga     480
gtcatgagaa ttgaagaccg gagtatgtta ccggactgta taccggggt gaaacatagc     540 ggtattcact ggacgcatga caataaagga tttttctatt gcccatatcc accctcgag     600 gaaggacaag atcttatgat tcatcctagc atgagtcaag aggtgcggta tcattttatt     660
ggtaccgacc agtctgaaga tattctgtgc tggaaagata ctgtgaaccc cactcatcac     720
ctcaagagct attttactga tgacggaaag tatttgtgc tctacatttt agaggatgt     780 aataacatga caaagtata ctgcttggat tgacagagc tgccaaatgg gcctgaaagt     840
ctccgtggga gagaaggctc agcgccttc ataaaacttg tggatagtt tgatgcattg     900 tatacagcca ttgctaatga tggttctgtg tttacattcc taactgataa ggatgcgacg     960
aggcgtaagt tagttcgcgt tgatttgaat aatccgagcg tgtggactga tgtgcttccg    1020
gagtccaagg acttgcttga atcggcacat gcagtcaacg gaaaccagct tcttattcgt    1080
tacctaagtg atgtcaaaca tatactagag cttaggggatc tcgaaagtgg ctctctattg    1140
catcgcatac ccatagacat tggagctgtt gatggtacta ttaatgcacg acgcggagac    1200
agtgtcgtgt ttttcaagtt acaagcatcc tgactccta gcattattta tcaatgtgat    1260 ttgaaaatg atcctccaca attaaagatc ttcagagaaa gtgttgtccc tgggttgac    1320 cgttctgagt tcgaggttaa acagcttttt gcgcctagca agatggcac aatgatacca    1380 acattcgtag cagcacgaaa gggaatttct tggatggtt cacacccatg tgaaatgcat    1440
ggttatggtg catatggcca gtgtatgatg ccaacttttt ctgccagtcg cttagtattt    1500

-continued

```
ttgaagcacc ttggcggcgt cttctgtttg gctaatattc gaggcggtgg tgaatatgga      1560
gtagaatggc ataaagcagg agcccgtgaa acaagcaaa acagttatga tgacttcatc       1620
gcctcagctg agtttcttgt ttctagtggc tacaccgcac ctaaaaaaat ttgtatcgaa      1680
ggtggaagta acgggggcct tctcattgct gtttgtatta ctcagagacc agacctgttc     1740
ggttgcgccg agccaaactg tggtcctatg gacatgattc gatttcatca ttttacacaa     1800
ggttatgtgg tgatgtcgga atatggttcc cccgacaaag aggaagagtt caactggctt    1860
atcaagtact caccgctaca taacgtgagg agaccatggg aacagccagg tcatgaacag    1920
acgcaatacc ccgcaactat gataataacg gctgatcatg atgatcgcgt ggtgccattt    1980
cattcgtata aaatgatagc tactatgcag catgttctgt gcacaagctt agaaaacagc    2040
ccgcagaaat ttccaataat ttgtcggatt cagcgcaacg cttcacatta tggacgtgcc    2100
acaatggttc agatcgctga agtagcagat cggtatggct ttatggcaaa ggcgctgaac    2160
gccacttgga cagac                                                                         2175
```

```
<210> SEQ ID NO 26
<211> LENGTH: 725
<212> TYPE: PRT
<213> ORGANISM: Dianthus superbus

<400> SEQUENCE: 26

Met Ala Val Ser Cys Gly Phe Thr Lys Thr Leu His Tyr Pro Pro Val
1               5                   10                  15

Arg Arg Asp Glu Thr Val Val Asp Asp Tyr Phe Gly Leu Lys Ile Ala
            20                  25                  30

Asp Pro Tyr Arg Trp Leu Glu Asp Leu Asn Ser Glu Glu Thr Lys Lys
        35                  40                  45

Phe Val Asp Asp Gln Val Lys Phe Thr Glu Ser Val Leu Glu Glu Cys
    50                  55                  60

Glu Leu Ile Gly Lys Val Lys Gln Lys Ile Ile Asp Tyr Val Ser Phe
65                  70                  75                  80

Pro Arg Trp Ser Val Pro Leu Arg Arg Ala Asn Lys Tyr Phe His Phe
                85                  90                  95

Tyr Asn Ser Gly Leu Gln Ser Gln Asn Val Tyr Arg Met Gln Asp Gly
            100                 105                 110

Leu Asp Gly Lys Pro Glu Val Val Tyr Asp Pro Asn Leu Arg Glu Gly
        115                 120                 125

Gly Arg Thr Gly Leu Thr Leu Tyr Ser Val Ser Glu Asp Ala Asn Tyr
    130                 135                 140

Phe Ala Phe Gly Ile Ala Glu Gly Phe Thr Glu Trp Leu Thr Ile Arg
145                 150                 155                 160

Val Met Arg Ile Glu Asp Arg Ser Met Leu Pro Asp Cys Ile Thr Gly
                165                 170                 175

Val Lys His Ser Gly Ile His Trp Thr His Asp Asn Lys Gly Phe Phe
            180                 185                 190

Tyr Cys Pro Tyr Pro Leu Glu Glu Gly Gln Asp Leu Met Ile His
        195                 200                 205

Pro Ser Met Ser Gln Glu Val Arg Tyr His Phe Ile Gly Thr Asp Gln
    210                 215                 220

Ser Glu Asp Ile Leu Cys Trp Lys Asp Thr Val Asn Pro Thr His His
225                 230                 235                 240

Leu Lys Ser Tyr Phe Thr Asp Asp Gly Lys Tyr Phe Val Leu Tyr Ile
                245                 250                 255
```

-continued

Leu Glu Gly Cys Asn Asn Met Asn Lys Val Tyr Cys Leu Asp Leu Thr
            260                 265                 270

Glu Leu Pro Asn Gly Pro Glu Ser Leu Arg Gly Arg Glu Gly Ser Ala
            275                 280                 285

Pro Phe Ile Lys Leu Val Asp Ser Phe Asp Ala Leu Tyr Thr Ala Ile
290                 295                 300

Ala Asn Asp Gly Ser Val Phe Thr Phe Leu Thr Asp Lys Asp Ala Thr
305                 310                 315                 320

Arg Arg Lys Leu Val Arg Val Asp Leu Asn Asn Pro Ser Val Trp Thr
            325                 330                 335

Asp Val Leu Pro Glu Ser Lys Asp Leu Leu Glu Ser Ala His Ala Val
            340                 345                 350

Asn Gly Asn Gln Leu Leu Ile Arg Tyr Leu Ser Asp Val Lys His Ile
            355                 360                 365

Leu Glu Leu Arg Asp Leu Glu Ser Gly Ser Leu Leu His Arg Ile Pro
            370                 375                 380

Ile Asp Ile Gly Ala Val Asp Gly Thr Ile Asn Ala Arg Arg Gly Asp
385                 390                 395                 400

Ser Val Val Phe Phe Lys Phe Thr Ser Ile Leu Thr Pro Ser Ile Ile
            405                 410                 415

Tyr Gln Cys Asp Leu Lys Asn Asp Pro Pro Gln Leu Lys Ile Phe Arg
            420                 425                 430

Glu Ser Val Val Pro Gly Phe Asp Arg Ser Glu Phe Glu Val Lys Gln
            435                 440                 445

Leu Phe Ala Pro Ser Lys Asp Gly Thr Met Ile Pro Thr Phe Val Ala
            450                 455                 460

Ala Arg Lys Gly Ile Ser Leu Asp Gly Ser His Pro Cys Glu Met His
465                 470                 475                 480

Gly Tyr Gly Ala Tyr Gly Gln Cys Met Met Pro Thr Phe Ser Ala Ser
            485                 490                 495

Arg Leu Val Phe Leu Lys His Leu Gly Gly Val Phe Cys Leu Ala Asn
            500                 505                 510

Ile Arg Gly Gly Gly Glu Tyr Gly Val Glu Trp His Lys Ala Gly Ala
            515                 520                 525

Arg Glu Asn Lys Gln Asn Ser Tyr Asp Asp Phe Ile Ala Ser Ala Glu
            530                 535                 540

Phe Leu Val Ser Ser Gly Tyr Thr Ala Pro Lys Lys Ile Cys Ile Glu
545                 550                 555                 560

Gly Gly Ser Asn Gly Gly Leu Leu Ile Ala Val Cys Ile Thr Gln Arg
            565                 570                 575

Pro Asp Leu Phe Gly Cys Ala Glu Pro Asn Cys Gly Pro Met Asp Met
            580                 585                 590

Ile Arg Phe His His Phe Thr Gln Gly Tyr Val Val Met Ser Glu Tyr
            595                 600                 605

Gly Ser Pro Asp Lys Glu Glu Glu Phe Asn Trp Leu Ile Lys Tyr Ser
            610                 615                 620

Pro Leu His Asn Val Arg Arg Pro Trp Glu Gln Pro Gly His Glu Gln
625                 630                 635                 640

Thr Gln Tyr Pro Ala Thr Met Ile Ile Thr Ala Asp His Asp Asp Arg
            645                 650                 655

Val Val Pro Phe His Ser Tyr Lys Met Ile Ala Thr Met Gln His Val
            660                 665                 670

```
Leu Cys Thr Ser Leu Glu Asn Ser Pro Gln Lys Phe Pro Ile Ile Cys
        675                 680                 685

Arg Ile Gln Arg Asn Ala Ser His Tyr Gly Arg Ala Thr Met Val Gln
        690                 695                 700

Ile Ala Glu Val Ala Asp Arg Tyr Gly Phe Met Ala Lys Ala Leu Asn
705                 710                 715                 720

Ala Thr Trp Thr Asp
                725

<210> SEQ ID NO 27
<211> LENGTH: 6
<212> TYPE: PRT
<213> ORGANISM: Artificial Sequence
<220> FEATURE:
<223> OTHER INFORMATION: Segetalin A variant aa1 = alanine
<220> FEATURE:
<221> NAME/KEY: MISC_FEATURE
<222> LOCATION: (1)..(6)
<223> OTHER INFORMATION: Cyclic peptide

<400> SEQUENCE: 27

Ala Val Pro Val Trp Ala
1               5

<210> SEQ ID NO 28
<211> LENGTH: 6
<212> TYPE: PRT
<213> ORGANISM: Artificial Sequence
<220> FEATURE:
<223> OTHER INFORMATION: Segetalin A variant aa2 = alanine
<220> FEATURE:
<221> NAME/KEY: MISC_FEATURE
<222> LOCATION: (1)..(6)
<223> OTHER INFORMATION: Cyclic peptide

<400> SEQUENCE: 28

Gly Ala Pro Val Trp Ala
1               5

<210> SEQ ID NO 29
<211> LENGTH: 6
<212> TYPE: PRT
<213> ORGANISM: Artificial Sequence
<220> FEATURE:
<223> OTHER INFORMATION: Segetalin A variant aa3 = alanine
<220> FEATURE:
<221> NAME/KEY: MISC_FEATURE
<222> LOCATION: (1)..(6)
<223> OTHER INFORMATION: Cyclic peptide

<400> SEQUENCE: 29

Gly Val Ala Val Trp Ala
1               5

<210> SEQ ID NO 30
<211> LENGTH: 6
<212> TYPE: PRT
<213> ORGANISM: Artificial Sequence
<220> FEATURE:
<223> OTHER INFORMATION: Segetalin A variant aa4 = alanine
<220> FEATURE:
<221> NAME/KEY: MISC_FEATURE
<222> LOCATION: (1)..(6)
<223> OTHER INFORMATION: Cyclic peptide

<400> SEQUENCE: 30

Gly Val Pro Ala Trp Ala
1               5
```

<210> SEQ ID NO 31
<211> LENGTH: 6
<212> TYPE: PRT
<213> ORGANISM: Artificial Sequence
<220> FEATURE:
<223> OTHER INFORMATION: Segetalin A variant aa5 = alanine
<220> FEATURE:
<221> NAME/KEY: MISC_FEATURE
<222> LOCATION: (1)..(6)
<223> OTHER INFORMATION: Cyclic peptide

<400> SEQUENCE: 31

Gly Val Pro Val Ala Ala
1               5

<210> SEQ ID NO 32
<211> LENGTH: 19
<212> TYPE: PRT
<213> ORGANISM: Artificial Sequence
<220> FEATURE:
<223> OTHER INFORMATION: Presegetalin A1[14,32] variant aa14 = alanine

<400> SEQUENCE: 32

Ala Val Pro Val Trp Ala Phe Gln Ala Lys Asp Val Glu Asn Ala Ser
1               5                   10                  15

Ala Pro Val

<210> SEQ ID NO 33
<211> LENGTH: 19
<212> TYPE: PRT
<213> ORGANISM: Artificial Sequence
<220> FEATURE:
<223> OTHER INFORMATION: Presegetalin A1[14,32] variant aa15 = alanine

<400> SEQUENCE: 33

Gly Ala Pro Val Trp Ala Phe Gln Ala Lys Asp Val Glu Asn Ala Ser
1               5                   10                  15

Ala Pro Val

<210> SEQ ID NO 34
<211> LENGTH: 19
<212> TYPE: PRT
<213> ORGANISM: Artificial Sequence
<220> FEATURE:
<223> OTHER INFORMATION: Presegetalin A1[14,32] variant aa16 = alanine

<400> SEQUENCE: 34

Gly Val Ala Val Trp Ala Phe Gln Ala Lys Asp Val Glu Asn Ala Ser
1               5                   10                  15

Ala Pro Val

<210> SEQ ID NO 35
<211> LENGTH: 19
<212> TYPE: PRT
<213> ORGANISM: Artificial Sequence
<220> FEATURE:
<223> OTHER INFORMATION: Presegetalin A1[14,32] variant aa17 = alanine

<400> SEQUENCE: 35

Gly Val Pro Ala Trp Ala Phe Gln Ala Lys Asp Val Glu Asn Ala Ser
1               5                   10                  15

Ala Pro Val

```
<210> SEQ ID NO 36
<211> LENGTH: 19
<212> TYPE: PRT
<213> ORGANISM: Artificial Sequence
<220> FEATURE:
<223> OTHER INFORMATION: Presegetalin A1[14,32] variant aa18 = alanine

<400> SEQUENCE: 36

Gly Val Pro Val Ala Ala Phe Gln Ala Lys Asp Val Glu Asn Ala Ser
1               5                   10                  15

Ala Pro Val

<210> SEQ ID NO 37
<211> LENGTH: 19
<212> TYPE: PRT
<213> ORGANISM: Artificial Sequence
<220> FEATURE:
<223> OTHER INFORMATION: Presegetalin A1[14,32] variant aa19 = valine

<400> SEQUENCE: 37

Gly Val Pro Val Trp Val Phe Gln Ala Lys Asp Val Glu Asn Ala Ser
1               5                   10                  15

Ala Pro Val

<210> SEQ ID NO 38
<211> LENGTH: 17
<212> TYPE: PRT
<213> ORGANISM: Artificial Sequence
<220> FEATURE:
<223> OTHER INFORMATION: Presegetalin A1[14,30]

<400> SEQUENCE: 38

Gly Val Pro Val Trp Ala Phe Gln Ala Lys Asp Val Glu Asn Ala Pro
1               5                   10                  15

Val

<210> SEQ ID NO 39
<211> LENGTH: 15
<212> TYPE: PRT
<213> ORGANISM: Artificial Sequence
<220> FEATURE:
<223> OTHER INFORMATION: Presegetalin A1[14,28]

<400> SEQUENCE: 39

Gly Val Pro Val Trp Ala Phe Gln Ala Lys Asp Val Glu Asn Ala
1               5                   10                  15

<210> SEQ ID NO 40
<211> LENGTH: 11
<212> TYPE: PRT
<213> ORGANISM: Artificial Sequence
<220> FEATURE:
<223> OTHER INFORMATION: Presegetalin A1[14,24]

<400> SEQUENCE: 40

Gly Val Pro Val Trp Ala Phe Gln Ala Lys Asp
1               5                   10

<210> SEQ ID NO 41
<211> LENGTH: 7
<212> TYPE: PRT
<213> ORGANISM: Artificial Sequence
<220> FEATURE:
<223> OTHER INFORMATION: Presegetalin A1[14,20]

<400> SEQUENCE: 41
```

```
Gly Val Pro Val Trp Ala Phe
1               5

<210> SEQ ID NO 42
<211> LENGTH: 6
<212> TYPE: PRT
<213> ORGANISM: Artificial Sequence
<220> FEATURE:
<223> OTHER INFORMATION: Presegetalin A1[14,19]

<400> SEQUENCE: 42

Gly Val Pro Val Trp Ala
1               5

<210> SEQ ID NO 43
<211> LENGTH: 19
<212> TYPE: PRT
<213> ORGANISM: Artificial Sequence
<220> FEATURE:
<223> OTHER INFORMATION: Presegetalin A1[14,32] F20A

<400> SEQUENCE: 43

Gly Val Pro Val Trp Ala Ala Gln Ala Lys Asp Val Glu Asn Ala Ser
1               5                   10                  15

Ala Pro Val

<210> SEQ ID NO 44
<211> LENGTH: 19
<212> TYPE: PRT
<213> ORGANISM: Artificial Sequence
<220> FEATURE:
<223> OTHER INFORMATION: Presegetalin A1[14,32] Q21A

<400> SEQUENCE: 44

Gly Val Pro Val Trp Ala Phe Ala Ala Lys Asp Val Glu Asn Ala Ser
1               5                   10                  15

Ala Pro Val

<210> SEQ ID NO 45
<211> LENGTH: 19
<212> TYPE: PRT
<213> ORGANISM: Artificial Sequence
<220> FEATURE:
<223> OTHER INFORMATION: Presegetalin A1[14,32] A22V

<400> SEQUENCE: 45

Gly Val Pro Val Trp Ala Phe Gln Val Lys Asp Val Glu Asn Ala Ser
1               5                   10                  15

Ala Pro Val

<210> SEQ ID NO 46
<211> LENGTH: 19
<212> TYPE: PRT
<213> ORGANISM: Artificial Sequence
<220> FEATURE:
<223> OTHER INFORMATION: Presegetalin A1[14,32] K23A

<400> SEQUENCE: 46

Gly Val Pro Val Trp Ala Phe Gln Ala Ala Asp Val Glu Asn Ala Ser
1               5                   10                  15

Ala Pro Val

<210> SEQ ID NO 47
```

```
<211> LENGTH: 19
<212> TYPE: PRT
<213> ORGANISM: Artificial Sequence
<220> FEATURE:
<223> OTHER INFORMATION: Presegetalin A1[14,32] D24A

<400> SEQUENCE: 47

Gly Val Pro Val Trp Ala Phe Gln Ala Lys Ala Val Glu Asn Ala Ser
1               5                   10                  15

Ala Pro Val

<210> SEQ ID NO 48
<211> LENGTH: 19
<212> TYPE: PRT
<213> ORGANISM: Artificial Sequence
<220> FEATURE:
<223> OTHER INFORMATION: Presegetalin A1[14,32] V25A

<400> SEQUENCE: 48

Gly Val Pro Val Trp Ala Phe Gln Ala Lys Asp Ala Glu Asn Ala Ser
1               5                   10                  15

Ala Pro Val

<210> SEQ ID NO 49
<211> LENGTH: 19
<212> TYPE: PRT
<213> ORGANISM: Artificial Sequence
<220> FEATURE:
<223> OTHER INFORMATION: Presegetalin A1[14,32] E26A

<400> SEQUENCE: 49

Gly Val Pro Val Trp Ala Phe Gln Ala Lys Asp Val Ala Asn Ala Ser
1               5                   10                  15

Ala Pro Val

<210> SEQ ID NO 50
<211> LENGTH: 19
<212> TYPE: PRT
<213> ORGANISM: Artificial Sequence
<220> FEATURE:
<223> OTHER INFORMATION: Presegetalin A1[14,32] N27A

<400> SEQUENCE: 50

Gly Val Pro Val Trp Ala Phe Gln Ala Lys Asp Val Glu Ala Ala Ser
1               5                   10                  15

Ala Pro Val

<210> SEQ ID NO 51
<211> LENGTH: 19
<212> TYPE: PRT
<213> ORGANISM: Artificial Sequence
<220> FEATURE:
<223> OTHER INFORMATION: Presegetalin A1[14,32] A28V

<400> SEQUENCE: 51

Gly Val Pro Val Trp Ala Phe Gln Ala Lys Asp Val Glu Asn Val Ser
1               5                   10                  15

Ala Pro Val

<210> SEQ ID NO 52
<211> LENGTH: 19
<212> TYPE: PRT
<213> ORGANISM: Artificial Sequence
<220> FEATURE:
```

```
<223> OTHER INFORMATION: Presegetalin A1[14,32] S29A

<400> SEQUENCE: 52

Gly Val Pro Val Trp Ala Phe Gln Ala Lys Asp Val Glu Asn Ala Ala
1               5                   10                  15

Ala Pro Val

<210> SEQ ID NO 53
<211> LENGTH: 19
<212> TYPE: PRT
<213> ORGANISM: Artificial Sequence
<220> FEATURE:
<223> OTHER INFORMATION: Presegetalin A1[14,32] A30V

<400> SEQUENCE: 53

Gly Val Pro Val Trp Ala Phe Gln Ala Lys Asp Val Glu Asn Ala Ser
1               5                   10                  15

Val Pro Val

<210> SEQ ID NO 54
<211> LENGTH: 19
<212> TYPE: PRT
<213> ORGANISM: Artificial Sequence
<220> FEATURE:
<223> OTHER INFORMATION: Presegetalin A1[14,32] P31A

<400> SEQUENCE: 54

Gly Val Pro Val Trp Ala Phe Gln Ala Lys Asp Val Glu Asn Ala Ser
1               5                   10                  15

Ala Ala Val

<210> SEQ ID NO 55
<211> LENGTH: 19
<212> TYPE: PRT
<213> ORGANISM: Artificial Sequence
<220> FEATURE:
<223> OTHER INFORMATION: Presegetalin A1[14,32] V32A

<400> SEQUENCE: 55

Gly Val Pro Val Trp Ala Phe Gln Ala Lys Asp Val Glu Asn Ala Ser
1               5                   10                  15

Ala Pro Ala

<210> SEQ ID NO 56
<211> LENGTH: 19
<212> TYPE: PRT
<213> ORGANISM: Artificial Sequence
<220> FEATURE:
<223> OTHER INFORMATION: Presegetalin A1[14,32] V15v
<220> FEATURE:
<221> NAME/KEY: MISC_FEATURE
<222> LOCATION: (2)..(2)
<223> OTHER INFORMATION: D-valine

<400> SEQUENCE: 56

Gly Val Pro Val Trp Ala Phe Gln Ala Lys Asp Val Glu Asn Ala Ser
1               5                   10                  15

Ala Pro Val

<210> SEQ ID NO 57
<211> LENGTH: 19
<212> TYPE: PRT
<213> ORGANISM: Artificial Sequence
<220> FEATURE:
```

<223> OTHER INFORMATION: Presegetalin A1[14,32] P16p
<220> FEATURE:
<221> NAME/KEY: MISC_FEATURE
<222> LOCATION: (3)..(3)
<223> OTHER INFORMATION: D-proline

<400> SEQUENCE: 57

Gly Val Pro Val Trp Ala Phe Gln Ala Lys Asp Val Glu Asn Ala Ser
1               5                   10                  15

Ala Pro Val

<210> SEQ ID NO 58
<211> LENGTH: 19
<212> TYPE: PRT
<213> ORGANISM: Artificial Sequence
<220> FEATURE:
<223> OTHER INFORMATION: Presegetalin A1[14,32] V17v
<220> FEATURE:
<221> NAME/KEY: MISC_FEATURE
<222> LOCATION: (4)..(4)
<223> OTHER INFORMATION: D-valine

<400> SEQUENCE: 58

Gly Val Pro Val Trp Ala Phe Gln Ala Lys Asp Val Glu Asn Ala Ser
1               5                   10                  15

Ala Pro Val

<210> SEQ ID NO 59
<211> LENGTH: 19
<212> TYPE: PRT
<213> ORGANISM: Artificial Sequence
<220> FEATURE:
<223> OTHER INFORMATION: Presegetalin A1[14,32] W18w
<220> FEATURE:
<221> NAME/KEY: MISC_FEATURE
<222> LOCATION: (5)..(5)
<223> OTHER INFORMATION: D-tryptophan

<400> SEQUENCE: 59

Gly Val Pro Val Trp Ala Phe Gln Ala Lys Asp Val Glu Asn Ala Ser
1               5                   10                  15

Ala Pro Val

<210> SEQ ID NO 60
<211> LENGTH: 19
<212> TYPE: PRT
<213> ORGANISM: Artificial Sequence
<220> FEATURE:
<223> OTHER INFORMATION: Presegetalin A1[14,32] A19a
<220> FEATURE:
<221> NAME/KEY: MISC_FEATURE
<222> LOCATION: (6)..(6)
<223> OTHER INFORMATION: D-alanine

<400> SEQUENCE: 60

Gly Val Pro Val Trp Ala Phe Gln Ala Lys Asp Val Glu Asn Ala Ser
1               5                   10                  15

Ala Pro Val

<210> SEQ ID NO 61
<211> LENGTH: 19
<212> TYPE: PRT
<213> ORGANISM: Artificial Sequence
<220> FEATURE:
<223> OTHER INFORMATION: Presegetalin A1[14,32] P16p W18A
<220> FEATURE:
<221> NAME/KEY: MISC_FEATURE
<222> LOCATION: (3)..(3)
<223> OTHER INFORMATION: D-proline

<400> SEQUENCE: 61

Gly Val Pro Val Ala Ala Phe Gln Ala Lys Asp Val Glu Asn Ala Ser
1               5                   10                  15

Ala Pro Val

<210> SEQ ID NO 62
<211> LENGTH: 19
<212> TYPE: PRT
<213> ORGANISM: Artificial Sequence
<220> FEATURE:
<223> OTHER INFORMATION: Presegetalin A1[14,32] P16p W18a
<220> FEATURE:
<221> NAME/KEY: MISC_FEATURE
<222> LOCATION: (3)..(3)
<223> OTHER INFORMATION: D-proline
<220> FEATURE:
<221> NAME/KEY: MISC_FEATURE
<222> LOCATION: (5)..(5)
<223> OTHER INFORMATION: D-alanine

<400> SEQUENCE: 62

Gly Val Pro Val Ala Ala Phe Gln Ala Lys Asp Val Glu Asn Ala Ser
1               5                   10                  15

Ala Pro Val

<210> SEQ ID NO 63
<211> LENGTH: 20
<212> TYPE: PRT
<213> ORGANISM: Artificial Sequence
<220> FEATURE:
<223> OTHER INFORMATION: Presegetalin A1[14,32] ins 16A17

<400> SEQUENCE: 63

Gly Val Pro Ala Val Trp Ala Phe Gln Ala Lys Asp Val Glu Asn Ala
1               5                   10                  15

Ser Ala Pro Val
            20

<210> SEQ ID NO 64
<211> LENGTH: 22
<212> TYPE: PRT
<213> ORGANISM: Artificial Sequence
<220> FEATURE:
<223> OTHER INFORMATION: Presegetalin A1[14,32] ins 16AAA17

<400> SEQUENCE: 64

Gly Val Pro Ala Ala Ala Val Trp Ala Phe Gln Ala Lys Asp Val Glu
1               5                   10                  15

Asn Ala Ser Ala Pro Val
            20

<210> SEQ ID NO 65
<211> LENGTH: 18
<212> TYPE: PRT
<213> ORGANISM: Artificial Sequence
<220> FEATURE:
<223> OTHER INFORMATION: Presegetalin B1[14,31]

<400> SEQUENCE: 65

Gly Val Ala Trp Ala Phe Gln Ala Lys Asp Val Glu Asn Ala Ser Ala
1               5                   10                  15

Pro Val

<210> SEQ ID NO 66
<211> LENGTH: 18
<212> TYPE: PRT
<213> ORGANISM: Artificial Sequence
<220> FEATURE:
<223> OTHER INFORMATION: Presegetalin D1[14,31]

<400> SEQUENCE: 66

Gly Leu Ser Phe Ala Phe Pro Ala Lys Asp Ala Glu Asn Ala Ser Ser
1               5                   10                  15

Pro Val

<210> SEQ ID NO 67
<211> LENGTH: 18
<212> TYPE: PRT
<213> ORGANISM: Artificial Sequence
<220> FEATURE:
<223> OTHER INFORMATION: Presegetalin D1[14,31] P20Q

<400> SEQUENCE: 67

Gly Leu Ser Phe Ala Phe Gln Ala Lys Asp Ala Glu Asn Ala Ser Ser
1               5                   10                  15

Pro Val

<210> SEQ ID NO 68
<211> LENGTH: 18
<212> TYPE: PRT
<213> ORGANISM: Artificial Sequence
<220> FEATURE:
<223> OTHER INFORMATION: Presegetalin G1[14,31]

<400> SEQUENCE: 68

Gly Val Lys Tyr Ala Phe Gln Pro Lys Asp Ser Glu Asn Ala Ser Ala
1               5                   10                  15

Pro Val

<210> SEQ ID NO 69
<211> LENGTH: 18
<212> TYPE: PRT
<213> ORGANISM: Artificial Sequence
<220> FEATURE:
<223> OTHER INFORMATION: Presegetalin H1[14,31]

<400> SEQUENCE: 69

Gly Tyr Arg Phe Ser Phe Gln Ala Lys Asp Ala Glu Asn Ala Ser Ala
1               5                   10                  15

Pro Val

<210> SEQ ID NO 70
<211> LENGTH: 19
<212> TYPE: PRT
<213> ORGANISM: Artificial Sequence
<220> FEATURE:
<223> OTHER INFORMATION: Presegetalin L1[14,32]

<400> SEQUENCE: 70

Gly Leu Pro Gly Trp Pro Phe Gln Ala Lys Asp Val Glu Asn Ala Ser
1               5                   10                  15

Ala Pro Val

<210> SEQ ID NO 71
<211> LENGTH: 25

```
<212> TYPE: PRT
<213> ORGANISM: Artificial Sequence
<220> FEATURE:
<223> OTHER INFORMATION: Presegetalin F1[14,38]

<400> SEQUENCE: 71

Phe Ser Ala Ser Tyr Ser Ser Lys Pro Ile Gln Thr Gln Val Ser Asn
1               5                   10                  15

Gly Met Asp Asn Ala Ser Ala Pro Val
            20                  25

<210> SEQ ID NO 72
<211> LENGTH: 23
<212> TYPE: PRT
<213> ORGANISM: Artificial Sequence
<220> FEATURE:
<223> OTHER INFORMATION: Presegetalin J1[14,36]

<400> SEQUENCE: 72

Phe Gly Thr His Gly Leu Pro Ala Pro Ile Gln Val Pro Asn Gly Met
1               5                   10                  15

Asp Asp Ala Cys Ala Pro Met
            20

<210> SEQ ID NO 73
<211> LENGTH: 20
<212> TYPE: PRT
<213> ORGANISM: Artificial Sequence
<220> FEATURE:
<223> OTHER INFORMATION: - Dianthus Precursor A[14,33]

<400> SEQUENCE: 73

Gly Pro Ile Pro Phe Tyr Gly Phe Gln Ala Lys Asp Ala Glu Asn Ala
1               5                   10                  15

Ser Val Pro Val
            20

<210> SEQ ID NO 74
<211> LENGTH: 19
<212> TYPE: PRT
<213> ORGANISM: Artificial Sequence
<220> FEATURE:
<223> OTHER INFORMATION: Dianthus Precursor B[14,33]

<400> SEQUENCE: 74

Gly Tyr Lys Asp Cys Cys Val Gln Ala Lys Asp Leu Glu Asn Ala Ala
1               5                   10                  15

Val Pro Val

<210> SEQ ID NO 75
<211> LENGTH: 11
<212> TYPE: PRT
<213> ORGANISM: Artificial Sequence
<220> FEATURE:
<223> OTHER INFORMATION: Stelladein A
<220> FEATURE:
<221> NAME/KEY: MISC_FEATURE
<222> LOCATION: (1)..(11)
<223> OTHER INFORMATION: Cyclic peptide

<400> SEQUENCE: 75

Pro Pro Pro Leu Leu Gly Pro Pro Tyr Tyr Gly
1               5                   10

<210> SEQ ID NO 76
```

```
<211> LENGTH: 7
<212> TYPE: PRT
<213> ORGANISM: Artificial Sequence
<220> FEATURE:
<223> OTHER INFORMATION: Segetalin A ins 3A4
<220> FEATURE:
<221> NAME/KEY: MISC_FEATURE
<222> LOCATION: (1)..(7)
<223> OTHER INFORMATION: Cyclic peptide

<400> SEQUENCE: 76

Gly Val Pro Ala Val Trp Ala
1               5

<210> SEQ ID NO 77
<211> LENGTH: 5
<212> TYPE: PRT
<213> ORGANISM: Artificial Sequence
<220> FEATURE:
<223> OTHER INFORMATION: Cyclization product of presegetalin D1[14,31]
<220> FEATURE:
<221> NAME/KEY: MISC_FEATURE
<222> LOCATION: (1)..(5)
<223> OTHER INFORMATION: Cyclic peptide

<400> SEQUENCE: 77

Gly Leu Ser Phe Ala
1               5
```

CYCLIC PEPTIDE PRODUCTION

CROSS-REFERENCE TO RELATED APPLICATIONS

This application is a national entry of International Patent Application PCT/CA2012/001130 filed Dec. 7, 2012 and claims the benefit of U.S patent application Ser. No. 61/567,844 filed Dec. 7, 2011 and U.S. patent application Ser. No. 61/640,115 filed Apr. 30, 2012, the entire contents of all of which are herein incorporated by reference.

FIELD OF THE INVENTION

This invention is related to biochemistry, more specifically to polypeptides, nucleic acid molecules and processes for producing cyclic peptides.

BACKGROUND OF THE INVENTION

Cyclic peptides (CPs) have commercial value as drugs, antimicrobial compounds and antigens in vaccines, but they can be difficult and expensive to produce. Also, the ability to make cyclic peptides of any size and sequence is commercially desirable both for screening of thousands of CPs for biological activity and for the production of specific valuable cyclic peptides.

According to the present knowledge, the so-called homodetic cyclic peptides or homocylopetides, which have a ring composed of amino acids linked by peptide bonds, can be produced by: extraction from natural sources, especially plants, fungi and microbes (Pomilio 2006; Tan 2006; Craik 2007; Cascales 2010; Morita 2010); chemical synthesis (White 2011; Lambert 2001; Davies 2003); cyclization of linear peptide precursors using isolated enzymes (Bolscher 2011; Katoh 2011; Grunewald 2006) including *Staphylococcus aureus* sortase A (Wu 2011), the *Prochloron didemni* patG gene product (McIntosh 2010) and trypsin (Thongyoo 2008); and, genetic engineering of various organisms including bacteria and plants, using genes encoding split inteins (Young 2011) and other inteins variants (Katoh 2011; Camarero 2011; Austin 2009), proteases and their homologues and/or cyclic peptide precursors (Katoh 2011; Condie 2011; Donia 2008; Tang 2011; Covello 2010; Schmidt 2010; Schmidt 2007) and non-ribosomal peptide synthetases (Kohli 2001).

Particularly relevant is the production of cyclic peptides based on the process which occurs in plants of the Caryophyllaceae family. It has been shown that in this family, precursor peptides are encoded by DNA (Condie 2011). When a DNA fragment encoding precursors is experimentally expressed in genetically transformed roots of *Saponaria vaccaria*, for example, a corresponding cyclic peptide is produced in the roots. Similarly, when a chemically synthesized precursor peptide is incubated with extracts of *Saponaria vaccaria*, a corresponding cyclic peptide is produced.

Also relevant is the use of purified enzymes, especially from recombinant microbes, for in vitro peptide cyclization. Generally these involve the use of chemically synthesized linear peptides which are incubated with a purified enzyme, such as sortase A or the patG gene product, capable of catalyzing the formation of a cyclic peptide from part of the linear peptide.

Existing methods have one or more drawbacks. Extraction from natural sources, especially plants, fungi and microbes is limited by the natural variation and abundance of cyclic peptides from these sources. Depending on the size and composition of the desired CP product, chemical synthesis can be complicated and expensive. Peptide cyclization by sortase A is limited to CP products which include a sorting sequence and usually one or two glycine residues. Production of desired CP product using the split intein method varies widely depending on the sequence. Use of inteins variants usually requires the inclusion of a cysteine in the cyclic product. In vivo peptide cyclization by sortase A is limited to CP products which include a sorting sequence and usually one or two glycine residues. Use of non-ribosomal peptide synthetases generally requires a substrate with a C-terminal thioester moiety.

There remains a need for alternative methods of producing cyclic peptides that overcomes one or more of the drawbacks of the prior art.

SUMMARY OF THE INVENTION

In an embodiment, there is provided an isolated nucleic acid molecule comprising a nucleotide sequence having at least 80% sequence identity to the nucleotide sequence as set forth in SEQ ID NO: 1, a full length complement thereof or a codon degenerate nucleotide sequence thereof.

In an embodiment, there is provided an isolated polypeptide comprising: an amino acid sequence having at least 80% sequence identity to the amino acid sequence as set forth in SEQ ID NO: 2; or, a conservatively substituted amino acid sequence of the amino acid sequence as set forth in SEQ ID NO: 2.

Nucleic acid molecule and polypeptides of the present invention are preferably from Caryophyllaceae family of plants, or are artificial sequences created therefrom by mutation, for example. Genera in the Caryophyllaceae family include, for example, *Acanthophyllum, Achyronychia, Agrostemma, Allochrusa, Alsinidendron, Ankyropetalum, Arenaria, Bolanthus, Bolbosaponaria, Brachystemma, Bufonia, Cardionema, Cerastium, Cerdia, Colobanthus, Cometes, Corrigiola, Cucubalus, Cyathophylla, Dianthus, Diaphanoptera, Dicheranthus, Drymaria, Drypis, Eremogone, Geocarpon, Gymnocarpos, Gypsophila, Habrosia, Haya, Herniaria, Holosteum, Honckenya, Illecebrum, Kabulia, Krauseola, Kuhitangia, Lepyrodiclis, Lochia, Loeflingia, Lychnis, Melandrium, Mesostemma, Microphyes, Minuartia, Moehringia, Moenchia, Myosoton, Ochotonophila, Ortegia, Paronychia, Pentastemonodiscus, Petrocoptis, Petrorhagia, Philippiella, Phrynella, Pinosia, Pirinia, Pleioneura, Plettkia, Pollichia, Polycarpaea, Polycarpon, Polytepalum, Pseudostellaria, Pteranthus, Pycnophyllopsis, Pycnophyllum, Reicheella, Sagina, Sanctambrosia, Saponaria, Schiedea, Scleranthopsis, Scleranthus, Sclerocephalus, Scopulophila, Selleola, Silene, Spergula, Spergularia, Sphaerocoma, Stellaria, Stipulicida, Thurya, Thylacospermum, Uebelinia, Vaccaria, Velezia, Wilhelmsia* and *Xerotia*.

In an embodiment, there is provided a nucleic acid construct comprising a nucleic acid molecule of the present invention operatively linked to one or more nucleotide sequences for aiding in transformation or transfection of a cell with the construct. The embodiment also relates to a construct comprising an isolated nucleic acid molecule of the present invention operably linked to suitable regulatory sequences. The construct may be a chimeric gene construct.

In an embodiment, there is provided a host cell comprising a construct or an isolated nucleic acid molecule of the present invention. The host cell may be eukaryotic, such as a yeast or a plant cell, or prokaryotic, such as a bacterial cell. This embodiment also relates to a virus comprising a chimeric gene construct or an isolated nucleic acid molecule of the present invention.

In an embodiment, there is provided a process for producing a host cell comprising a construct or an isolated nucleic acid molecule of the present invention, the process comprising transforming or transfecting a compatible host cell with a chimeric gene construct or an isolated nucleic acid molecule of the present invention.

In an embodiment, there is provided a process of producing a cyclic peptide, the process comprising contacting a suitable linear peptide precursor of the cyclic peptide with an isolated polypeptide comprising an amino acid sequence having at least 75% sequence identity to the amino acid sequence as set forth in SEQ ID NO: 2 or a conservatively substituted amino acid sequence of the amino acid sequence as set forth in SEQ ID NO: 2 to produce the cyclic peptide from the linear peptide precursor. A suitable linear peptide precursor is a linear peptide that is capable as acting a substrate for the polypeptide of the present invention, where the action of the polypeptide on the linear peptide produces the cyclic peptide. The process may be performed in vitro, or in vivo in a host cell or organism transformed or transfected with a construct or nucleic acid molecule of the present invention. The linear peptide precursor may be produced chemically or through recombinant organisms.

The present invention permits production of a wide range of cyclic peptides which find use as drugs, antimicrobial compounds, vaccine antigens or nanotube related technologies. The present invention may also be used to generate large libraries of cyclic peptides for screening to identify cyclic peptides of commercial interest.

In another embodiment, there is provided a method of reducing cyclopeptide content in a host cell, tissue or plant comprising: reducing expression in the cell, tissue or plant of a nucleic acid molecule comprising a nucleotide sequence having at least 80% sequence identity to the nucleotide sequence as set forth in SEQ ID NO: 1, compared to expression of the nucleotide sequence in the cell, tissue or plant before expression was reduced.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which:

FIG. 1 depicts manual alignment of predicted amino acid sequences of cDNAs encoding putative presegetalins from *S. vaccaria*. Known mature segetalin (cyclic peptide) sequences are shown in reverse type; predicted segetalin sequences are in italics. Presegetalin names are shown at the right.

FIG. 4 depicts the nucleotide sequence of the open reading frame of Pcy1 of *S. vaccaria* without the stop codon.

FIG. 5 depicts the predicted amino acid sequence of PCY1 of *S. vaccaria.*

FIG. 6 depicts a time course of in vitro production of segetalin A by recombinant PCY1 from presegetalin A1[14, 32]. Enzyme assays were performed at pH 8.5 with recombinant PCY1 and analyzed by LC/MS. Total ion current chromatograms are shown for 0, 30, 60, and 90 min incubations. The bottom panel shows a chromatogram corresponding to 10 ng of segetalin A standard.

FIG. 7 depicts chromatograms showing activity of PCY1 enzymes from *S. vaccaria, D. superbus* and *S. vulgaris*. Recombinant PCY1 homologues from *S. vaccaria, D. superbus* (contig c250) and *S. vulgaris* (c150) were assayed with presegetalin A1[14,32]. Panels a, b and c show single ion monitoring LC-MS chromatograms for (a) segetalin A [(M+1) at m/z 610.5 and retention time (17.1 min)], (b) assay of recombinant PCY1 from *Saponaria vaccaria*, and (c) assay of recombinant PCY1 from *Dianthus superbus*. Insets in (a), (b) and (c) show MS/MS fragmentation of m/z=610.5. Panel d shows a total ion trap current chromatogram (monitoring m/z range 50 to 2200 atomic mass units) of an assay of recombinant PCY1 from *Silene vulgaris* with fragmentation (inset) similar to the segetalin A standard.

FIG. 8 depicts LC/MS chromatographs of assays of recombinant *Saponaria* vaccaria PCY1 (left) and *Dianthus superbus* c250 (right) showing single ion traces of alanine and valine substituted synthetic mutants of presegetalin A1[14, 32] in the aa14 position (a and g), aa15 position (b and h), aa16 position (c and i), aa17 position (d and j) and aa18 position (e and k) and a substitution of valine in the aa19 position (f and l). The lighter grey traces represent the diagnostic ions for the reaction substrate (multiple charged molecular ions, specifically the sum of $(M+2H)^{2+}$ and $(M+3H)^{3+}$). The darker black traces represent the identification of a peak containing the diagnostic ions for the expected cyclized peptide product (the sum of $(M+H)^{+}$ and $(M+Na)^{+}$). The various sequences are identified as follows: AVPVWAFQAKDVENASAPV (SEQ ID NO: 32), cyclo (AVPVWA) (SEQ ID NO: 27), GAPVWAFQAKDVENASAPV (SEQ ID NO: 33), cyclo(GAPVWA) (SEQ ID NO: 28), GVAVWAFQAKDVENASAPV (SEQ ID NO: 34), cyclo(GVAVWA) (SEQ ID NO: 29), GVPAWAFQAKDVENASAPV (SEQ ID NO: 35), cyclo(GVPAWA) (SEQ ID NO: 30), GVPVAAFQAKDVENASAPV (SEQ ID NO: 36), cyclo (GVPVAA) (SEQ ID NO: 31) and GVPVWVFQAKDVENASAPV (SEQ ID NO: 37).

FIG. 9 depicts a graph of segetalin A produced by *S. vaccaria* PCY1 from wild type (WT) and alanine scanning mutants of the C-terminal region of presegetalin A1[14,32] substrates.

FIG. 10 depicts a graph of linear segetalin A produced by PCY1 from wild type (WT) and mutant substrates. The empty bar line for presegetain A1[14,32] F20A does not indicate the absence of linear segetalin A, the presence of linear peptide was confirmed by MS/MS analysis but it is not possible to quantify it in LC/MS due to high noise level.

FIG. 11 depicts LC/MS analysis showing detection of D-amino acid variants of mature segetalin A in LC/MS. The L-form of amino acids is represented by upper case and D-form by lower case letters.

FIG. 12 depicts detection of a cyclic peptide with an alternating D- and L-amino acid arrangement (produced from No. 32 in Table 3) in LC/MS. The activity of *D. superbus* PCY1-c1141 (a) is higher than the activity of *S. vaccaria* PCY1 (b).

The cyclic peptide was identified by monitoring expected molecular ions (M+H)+ and (M+Na)+ and verified by MS/MS analysis.

DESCRIPTION OF PREFERRED EMBODIMENTS

Terms

Figure 2:
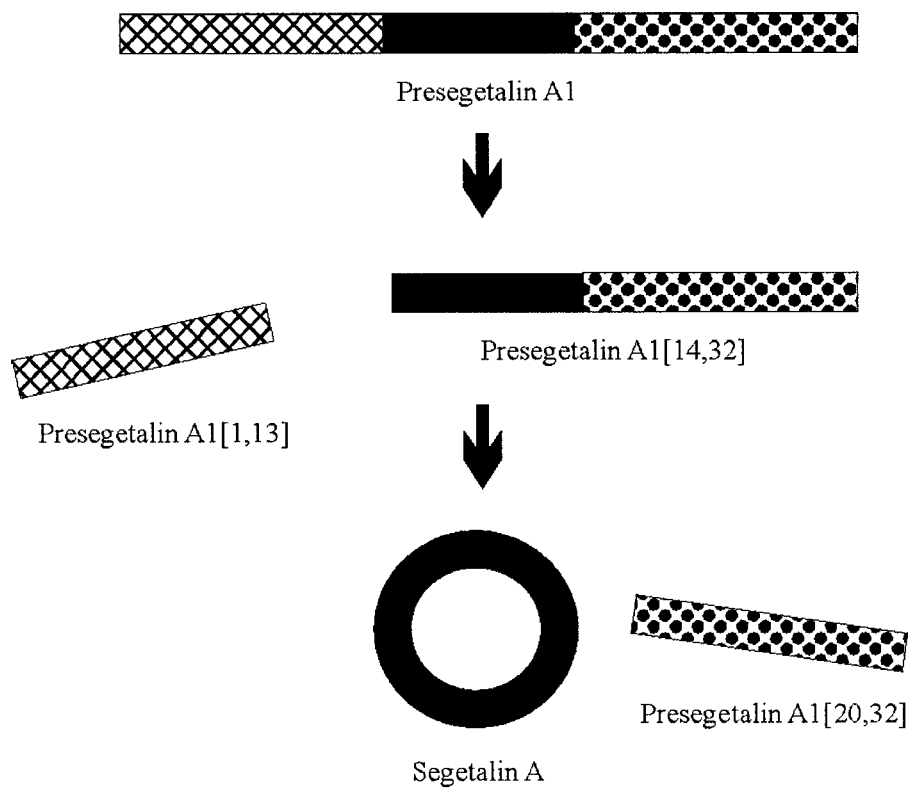
FIG. 2 depicts a proposed pathway to segetalin A from presegetalin A1 in *S. vaccaria*.

In order to facilitate review of the various embodiments of the disclosure, the following explanations of specific terms are provided:

Complementary nucleotide sequence: "Complementary nucleotide sequence" of a sequence is understood as meaning any DNA whose nucleotides are complementary to those of sequence of the disclosure, and whose orientation is reversed (antiparallel sequence).

Degree or percentage of sequence homology: The term "degree or percentage of sequence homology" refers to degree or percentage of sequence identity between two sequences after optimal alignment. Percentage of sequence identity (or degree or identity) is determined by comparing two optimally aligned sequences over a comparison window, where the portion of the peptide or polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity.

Isolated: As will be appreciated by one of skill in the art, "isolated" refers to polypeptides or nucleic acids that have been "isolated" from their native environment.

Nucleotide, polynucleotide, or nucleic acid sequence: "Nucleotide, polynucleotide, or nucleic acid sequence" will be understood as meaning both a double-stranded or single-stranded DNA in the monomeric and dimeric (so-called in tandem) forms and the transcription products of said DNAs.

Sequence identity: Two amino-acid or nucleotide sequences are said to be "identical" if the sequence of amino-acids or nucleotide residues in the two sequences is the same when aligned for maximum correspondence as described below. Sequence comparisons between two (or more) peptides or polynucleotides are typically performed by comparing sequences of two optimally aligned sequences over a segment or "comparison window" to identify and compare local regions of sequence similarity. Optimal alignment of sequences for comparison may be conducted by the local homology algorithm of Smith and Waterman (Smith 1981), by the homology alignment algorithm of Neddleman and Wunsch (Neddleman 1970), by the search for similarity method of Pearson and Lipman (Pearson 1988), by computerized implementation of these algorithms (GAP, BESTFIT, FASTA, and TFASTA in the Wisconsin Genetics Software Package, Genetics Computer Group (GCG), 575 Science Dr., Madison, Wis.), or by visual inspection. Isolated and/or purified sequences of the present invention or used in the present invention may have a percentage identity with the bases of a nucleotide sequence, or the amino acids of a polypeptide sequence, of at least about 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7%. When used in a process of producing a cyclic peptide, the sequences may have a percentage identity with the bases of a nucleotide sequence, or the amino acids of a polypeptide sequence, of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7%. These percentages are purely statistical, and it is possible to distribute the differences between two nucleotide or amino acid sequences at random and over the whole of their length.

It will be appreciated that this disclosure embraces the degeneracy of codon usage as would be understood by one of ordinary skill in the art and as illustrated in Table 1.

Furthermore, it will be understood by one skilled in the art that conservative substitutions may be made in the amino acid sequence of a polypeptide without disrupting the structure or function of the polypeptide. Conservative substitutions are accomplished by the skilled artisan by substituting amino acids with similar hydrophobicity, polarity, and R-chain length for one another. Additionally, by comparing aligned sequences of homologous proteins from different species, conservative substitutions may be identified by locating amino acid residues that have been mutated between species without altering the basic functions of the encoded proteins. Table 2 provides an exemplary list of conservative substitutions.

TABLE 1

Codon Degeneracies

| Amino Acid | Codons |
| --- | --- |
| Ala/A | GCT, GCC, GCA, GCG |
| Arg/R | CGT, CGC, CGA, CGG, AGA, AGG |
| Asn/N | AAT, AAC |
| Asp/D | GAT, GAC |
| Cys/C | TGT, UGC |
| Gln/Q | CAA, CAG |
| Glu/E | GAA, GAG |
| Gly/G | GGT, GGC, GGA, GGG |
| His/H | CAT, CAC |
| Ile/I | ATT, ATC, ATA |
| Leu/L | TTA, TTG, CTT, CTC, CTA, CTG |
| Lys/K | AAA, AAG |
| Met/M | ATG |
| Phe/F | TTT, TTC |
| Pro/P | CCT, CCC, CCA, CCG |
| Ser/S | TCT, TCC, TCA, TCG, AGT, AGC |
| Thr/T | ACT, ACC, ACA, ACG |
| Trp/W | TGG |
| Tyr/Y | TAT, TAC |
| Val/V | GTT, GTC, GTA, GTG |
| START | ATG |
| STOP | TAG, TGA, TAA |

TABLE 2

Conservative Substitutions

| Type of Amino Acid | Substitutable Amino Acids |
| --- | --- |
| Hydrophilic | Ala, Pro, Gly, Glu, Asp, Gln, Asn, Ser, Thr |
| Sulphydryl | Cys |
| Aliphatic | Val, Ile, Leu, Met |
| Basic | Lys, Arg, His |
| Aromatic | Phe, Tyr, Trp |

The definition of sequence identity given above is the definition that would be used by one of skill in the art. The definition by itself does not need the help of any algorithm, said algorithms being helpful only to achieve the optimal alignments of sequences, rather than the calculation of sequence identity. From the definition given above, it follows that there is a well defined and only one value for the sequence identity between two compared sequences which value corresponds to the value obtained for the best or optimal alignment. In the BLAST N or BLAST P "BLAST 2 sequence", software which is available in the web site http://www.ncbi.nlm.nih.gov/gorf/bl2.html, and habitually used by the inventors and in general by the skilled man for comparing and determining the identity between two sequences, gap cost which depends on the sequence length to be compared is directly selected by the software (i.e. 11.2 for substitution matrix BLOSUM-62 for length>85).

Expression

Nucleic acid molecules of the present invention can be expressed in alternate plant hosts to impart characteristics of improved agronomic performance via recombinant means. The methods to construct expression vectors and to transform and express foreign genes in plant and plant cells are well known in the art.

Such heterologous expression can also be conducted in microorganisms, such as in bacteria (e.g. *E. coli*), yeast (e.g. *S. cerevisiae*) and in fungi, which can this serve as host for the recombinant expression of the nucleic acid molecules and for the production and isolation of cyclopeptides produced therefrom.

Additionally, it is evident that the nucleic acid molecules can be used in the construction of expression vectors for heterologous expression in diverse host cells and organisms by conventional techniques. These methods, which can be used in the invention, have been described elsewhere (Potrykus 1991; Vasil 1994; Walden 1995; Songstad 1995), and are well known to persons skilled in the art. As known in the art, there are a number of ways by which genes and gene constructs can be introduced into plants and other organisms and a combination of transformation/transfection and tissue culture techniques have been successfully integrated into effective strategies for creating transgenic organisms. For example, one skilled in the art will certainly be aware that, in addition to *Agrobacterium*-mediated transformation of *Arabidopsis* by vacuum infiltration (Bechtold 1993) or wound inoculation (Katavic 1994), it is equally possible to transform other plant species, using *Agrobacterium* Ti-plasmid mediated transformation (e.g., hypocotyl (DeBlock 1989) or cotyledonary petiole (Moloney 1989) wound infection), particle bombardment/biolistic methods (Sanford 1987; Nehra 1994; Becker 1994) or polyethylene glycol-assisted, protoplast transformation (Rhodes 1988; Shimamoto 1989) methods.

As will also be apparent to persons skilled in the art, and as described elsewhere (Meyer 1995; Datla 1997), it is possible to utilize promoters to direct any intended regulation of transgene expression using constitutive promoters (e.g., those based on CaMV35S), or by using promoters which can target gene expression to particular cells, tissues (e.g., napin promoter for expression of transgenes in developing seed cotyledons), organs (e.g., roots), to a particular developmental stage, or in response to a particular external stimulus (e.g., heat shock). Promoters for use herein may be inducible, constitutive, or tissue-specific or cell specific or have various combinations of such characteristics. Useful promoters include, but are not limited to constitutive promoters such as carnation etched ring virus (CERV), cauliflower mosaic virus (CaMV) 35S promoter, or more particularly the double enhanced cauliflower mosaic virus promoter, comprising two CaMV 35S promoters in tandem (referred to as a "Double 35S" promoter). Meristem specific promoters include, for example, STM, BP, WUS, CLV gene promoters. Seed specific promoters include, for example, the napin promoter. Other cell and tissue specific promoters are well known in the art.

Promoter and termination regulatory regions that will be functional in the host cell may be heterologous (that is, not naturally occurring) or homologous (derived from the host species) to the cell and the gene. Suitable promoters which may be used are described above. The termination regulatory region may be derived from the 3' region of the gene from which the promoter was obtained or from another gene. Suitable termination regions which may be used are well known in the art and include *Agrobacterium tumefaciens* nopaline synthase terminator (Tnos), *A. tumefaciens* mannopine synthase terminator (Tmas) and the CaMV 35S terminator (T353). Particularly preferred termination regions for use herein include the pea ribulose bisphosphate carboxylase small subunit termination region (TrbcS) or the Tnos termination region. Such gene constructs may suitably be screened for activity by transformation/transfection into a host via *Agrobacterium* and screening for the desired activity using known techniques.

Preferably, a nucleic acid molecule construct for use herein is comprised within a vector, most suitably an expression vector adapted for expression in an appropriate cell. It will be appreciated that any vector which is capable of producing an organism comprising the introduced nucleic acid sequence will be sufficient. Suitable vectors are well known to those skilled in the art and are described in general technical references. Particularly suitable vectors include the Ti plasmid vectors. After transformation/transfection of the cells or organism, those cells or organisms into which the desired nucleic acid molecule has been incorporated may be selected by such methods as antibiotic resistance, herbicide resistance, tolerance to amino-acid analogues or using phenotypic markers. Various assays may be used to determine whether the cell shows an increase in gene expression, for example, Northern blotting or quantitative reverse transcriptase PCR (RT-PCR). Whole transgenic organisms may be regenerated from the transformed/transfected cell by conventional methods. When the organism is a plant, such plants produce seeds containing the genes for the introduced trait and can be grown to produce plants that will produce the selected phenotype.

Silencing

Silencing may be accomplished in a number of ways generally known in the art, for example, RNA interference (RNAi) techniques, artificial microRNA techniques, virus-induced gene silencing (VIGS) techniques, antisense techniques, sense co-suppression techniques and targeted mutagenesis techniques.

RNAi techniques involve stable transformation using RNA interference (RNAi) plasmid constructs (Helliwell 2005). Such plasmids are composed of a fragment of the target gene to be silenced in an inverted repeat structure. The inverted repeats are separated by a spacer, often an intron. The RNAi construct driven by a suitable promoter, for example, the Cauliflower mosaic virus (CaMV) 35S promoter, is integrated into the plant genome and subsequent transcription of the transgene leads to an RNA molecule that folds back on itself to form a double-stranded hairpin RNA. This double-stranded RNA structure is recognized by the plant and cut into small RNAs (about 21 nucleotides long) called small interfering RNAs (siRNAs). siRNAs associate with a protein complex (RISC) which goes on to direct degradation of the mRNA for the target gene.

Artificial microRNA (amiRNA) techniques exploit the microRNA (miRNA) pathway that functions to silence endogenous genes in plants and other eukaryotes (Schwab 2006; Alvarez 2006). In this method, 21 nucleotide long fragments of the gene to be silenced are introduced into a pre-miRNA gene to form a pre-amiRNA construct. The pre-miRNA construct is transferred into the plant genome using transformation methods apparent to one skilled in the art. After transcription of the pre-amiRNA, processing yields amiRNAs that target genes which share nucleotide identity with the 21 nucleotide amiRNA sequence.

In RNAi silencing techniques, two factors can influence the choice of length of the fragment. The shorter the fragment the less frequently effective silencing will be achieved, but very long hairpins increase the chance of recombination in bacterial host strains. The effectiveness of silencing also appears to be gene dependent and could reflect accessibility of target mRNA or the relative abundances of the target mRNA and the hpRNA in cells in which the gene is active. A fragment length of between 100 and 800 bp, preferably between 300 and 600 bp, is generally suitable to maximize the efficiency of silencing obtained. The other consideration is the part of the gene to be targeted. 5' UTR, coding region, and 3' UTR fragments can be used with equally good results. As the mechanism of silencing depends on sequence homology there is potential for cross-silencing of related mRNA sequences. Where this is not desirable a region with low sequence similarity to other sequences, such as a 5' or 3' UTR, should be chosen. The rule for avoiding cross-homology silencing appears to be to use sequences that do not have blocks of sequence identity of over 20 bases between the construct and the non-target gene sequences. Many of these same principles apply to selection of target regions for designing amiRNAs.

Virus-induced gene silencing (VIGS) techniques are a variation of RNAi techniques that exploits the endogenous antiviral defenses of plants. Infection of plants with recombinant VIGS viruses containing fragments of host DNA leads to post-transcriptional gene silencing for the target gene. In one embodiment, a tobacco rattle virus (TRV) based VIGS system can be used.

Antisense techniques involve introducing into a plant an antisense oligonucleotide that will bind to the messenger RNA (mRNA) produced by the gene of interest. The "antisense" oligonucleotide has a base sequence complementary to the gene's messenger RNA (mRNA), which is called the "sense" sequence. Activity of the sense segment of the mRNA is blocked by the anti-sense mRNA segment, thereby effectively inactivating gene expression. Application of antisense to gene silencing in plants is described in more detail by Stam 2000.

Sense co-suppression techniques involve introducing a highly expressed sense transgene into a plant resulting in reduced expression of both the transgene and the endogenous gene (Depicker 1997). The effect depends on sequence identity between transgene and endogenous gene.

Targeted mutagenesis techniques, for example TILLING (Targeting Induced Local Lesions IN Genomes) and "delete-a-gene" using fast-neutron bombardment, may be used to knockout gene function in a plant (Henikoff 2004; Li 2001). TILLING involves treating seeds or individual cells with a mutagen to cause point mutations that are then discovered in genes of interest using a sensitive method for single-nucleotide mutation detection. Detection of desired mutations (e.g. mutations resulting in the inactivation of the gene product of interest) may be accomplished, for example, by PCR methods. For example, oligonucleotide primers derived from the gene of interest may be prepared and PCR may be used to amplify regions of the gene of interest from plants in the mutagenized population. Amplified mutant genes may be annealed to wild-type genes to find mismatches between the mutant genes and wild-type genes. Detected differences may be traced back to the plants which had the mutant gene thereby revealing which mutagenized plants will have the desired expression (e.g. silencing of the gene of interest). These plants may then be selectively bred to produce a population having the desired expression. TILLING can provide an allelic series that includes missense and knockout mutations, which exhibit reduced expression of the targeted gene. TILLING is touted as a possible approach to gene knockout that does not involve introduction of transgenes, and therefore may be more acceptable to consumers. Fast-neutron bombardment induces mutations, i.e. deletions, in plant genomes that can also be detected using PCR in a manner similar to TILLING.

Silencing of genes that encode the enzymes of the present invention may be useful to reduce levels of undesirable cyclopeptides in plants, and to facilitate production of a single cyclopeptide so as to simplify extraction/purification.

EXAMPLES

Previously it was shown that in the Caryophyllaceae family, cyclic peptides are produced from linear peptides which are DNA-encoded. FIG. 1 shows examples of such DNA-encoded precursor sequences. For example, segetalin A or cyclo(GVPVWA) (SEQ ID NO: 14) is derived from the first precursor presegetalin A1 (labeled A1 (SEQ ID NO: 3) in FIG. 1). This was shown by arranging for the expression of a gene encoding presegetalin A1 in transformed root cultures of S. vaccaria. Similarly, when extracts of S. vaccaria developing seeds were incubated with chemically synthesized presegetalin A1, segetalin A was produced. These results were published previously (Condie 2011; Covello 2010).

However, why cyclic peptides are produced from such linear precursor peptides remained unknown. In the present invention, it has now been shown that the production of cyclic peptides from such linear precursors is accomplished enzymatically. As a result of the present invention, it can now be hypothesized that the pathway from presegetalin A1 to segetalin A involves initial cleavage of presegetalin A1 after position 13, giving rise to hitherto unknown intermediate linear precursors presegetalin A1[1,13] (SEQ ID NO: 16) and presegetalin A1[14,32] (SEQ ID NO: 15), as shown in FIG. 2. The intermediate linear precursor presegetalin A1[14,32] then gives rise to the cyclic peptide segetalin A. Thus, in one embodiment, the polypeptide of the present invention is an enzyme that catalyzes the conversion of presegetalin A1[14,32] to segetalin A. Thus, presegetalin A1[14,32] is the immediate linear peptide precursor to segetalin A in the biosynthesis of segetalin A, and presegetalin A1 is a linear peptide precursor farther removed from segetalin A in the biosynthetic pathway leading to segetalin A. It is expected that the enzyme would be useful in the production of a variety of cyclic peptides in a similar manner.

In general, for the enzymatic production of cyclic peptides using an enzyme of the present invention, suitable immediate linear peptide precursors comprise the amino acid sequence that will form the cyclic peptide at one terminus of the linear peptide precursor, preferably the N-terminus, and a flanking region that is cleaved away from the cyclic peptide-forming amino acid sequence during formation of the cyclic peptide.

Example 1

Materials and Methods for Determining Biosynthetic Pathway of Segetalins in *Saponaria vaccaria*

Chemicals

Presegetalin A1 (SEQ ID NO: 3, $M_r$=3400.30; purity≥75%) and presegetalin A1[14,32] (SEQ ID NO: 15, $M_r$=1984.05; purity>75%) were chemically synthesized at the Sheldon Biotechnology Centre, McGill University. The presegetalin A1 was further purified by a standard peptide HPLC fractionation on a C18 column using a water to acetonitrile gradient (with TFA as modifier). Segetalin A (SEQ ID NO: 14) was isolated from *S. vaccaria* seed by the method of Morita (Morita 1994).

Plant Material

*Saponaria vaccaria* 'White Beauty' seeds were obtained from CN Seeds Ltd (United Kingdom). Plants were grown under a daily regime of 16 h light (150 µEinstein $m^{-2}$ $s^{-1}$) at 24° C. and 8 h dark at 20° C. Stage 2 developing seeds were harvested according to the following scheme: Stage 1, seed white, pod green; Stage 2, seed tan; Stage 3, seed copper, pod partially dessicated; Stage 4, seed dark brown, pod dessicated.

In Vitro Processing of Presegetalin A1

Stage 2 developing seeds from *S. vaccaria* (var. White Beauty) were homogenized manually with a plastic pestle in 1.5 mL low protein binding microcentrifuge tubes. One gram of seeds was ground for 2 min in 4×250 µL 20 mM Tris buffer (pH 8) on ice followed by centrifugation at 13,000×g for 5 min. The supernatant was removed and another 250 µL buffer was added and the grinding and centrifugation was repeated. The supernatant fractions were pooled and this crude extract was used for enzyme assays. The crude extract protein was measured using Bradford reagent with BSA as a calibration standard (BioRad). The in vitro assay contained 20 mM Tris, 100 mM NaCl, 2 mM DTT, 0.2 mg BSA and 25 µg/mL presegetalin A1 and was initiated by the addition of crude extract, equivalent to 4.0 µg protein, in a total reaction volume of 100 µL. Unless otherwise stated, the assay was performed at pH 8.5. The assays were incubated at 30° C. for up to 5 h and stopped by placing reactions in dry ice. The assays were lyophilized, re-suspended in methanol, evaporated and re-suspended in 50:50 v/v methanol/water for LC/MS analysis.

Ion trap ESI+ LC/MS analysis was used to detect production of segetalin A using an Agilent 6320 Ion Trap LC/MS system under default Smart Parameter settings. The analyzer and ion optics were adjusted to achieve proper resolution (Agilent Installation Guide #G2440-90105) using the ESI Tuning Mix (Agilent #G2431A). The mass spectrometer scanned in the m/z range of 50 to 2200 at 8100 mass units/s with an expected peak width of ≤0.35 mass units. For automated MS/MS, the trap isolation width was 4 atomic mass units. The associated Agilent 1200 LC was fitted with a Zorbax™ 300 EXTEND-C18 column (150×2.1 mm, 3.5 µm particle size) maintained at 35° C. The binary solvent system consisted of 90:10 v/v water/acetonitrile containing 0.1% formic acid and 0.1% ammonium formate (solvent A) and 10:90 v/v water/acetonitrile containing 0.1% formic acid and 0.1% ammonium formate (solvent B). The separation gradient was 90:10 A/B to 50:50 A/B in 3 mL over 20 min. The detection of segetalin A in assay samples is described previously (Condie 2011).

Fractionation of *S. vaccaria* Developing Seed Extracts

In an effort to elucidate the enzymes and possible peptide intermediates which could be involved in peptide cyclization in developing seeds of *Saponaria vaccaria*, extracts of the seeds were subjected to fractionation by liquid chromatography and subsequent biochemical analysis. Two mg of total soluble protein from stage 2 developing seed (var. White Beauty) was fractionated (1 mL fraction volume) on a MonoQ 5/50 GL ion exchange column (GE Healthcare, Life Sciences, Mississauga, Canada) with 20 mM Tris pH 8.0 as the buffer and a gradient of 0 to 0.8 M NaCl over a volume of 10 mL using an Agilent 1100 HPLC equipped with an auto injector, diode array detector and fraction collector. These fractions were assayed for loss of substrate and the production of segetalin A and other possible products, using presegetalin A1 as a substrate (see above). HPLC analysis of fractions showed significant loss of presegetalin A1 in fractions 4 through 9 (peaking in fractions 5 and 6) and production of segetalin A in fraction 4.

In an effort to identify intermediates formed during precursor processing, assay samples were analyzed by MALDI-TOF MS. Samples were purified by adsorption onto and elution from C18 Empore™ High Performance Disk material (3M, Minneapolis, Minn., USA) using the "Stage tip" method (Rappsilber 2003). Stage tips were prepared by removing the beveled tip from a 20 gauge syringe needle with a tubing cutter. Empore™ disk material was then cut, cookie cutter style, with this needle and packed into the tip of a 10 µL pipette tip with a piece of fused silica tubing. Methanol (10 µL) was applied to the tip and expelled slowly with a 1.25 mL syringe. Aqueous trifluoroacetic acid (TFA; 0.1%) was then passed through the tip, followed by assay sample (20 µL). The disk material was washed with 20 µl 0.1% TFA and peptides were then eluted with 20 µL acetonitrile:aqueous 0.1% TFA.

Analysis of the peptides was carried out using an AB Sciex™ 4800 Plus MALDI TOF-TOF™ Analyzer. The mass spectrometer was operated in positive ion reflectron mode scanning from m/z values of 500 to 4000. The default calibration was updated with a standard mixture of peptides containing des-Arg[1] bradykinin (m/z 904.468), Gu[1] fibrinopeptide B (m/z 1570.677), and three ACTH fragments corresponding to amino acids 1-17 (m/z 2093.087), 18-39 (m/z 2465.199), and 7-38 (m/z 3657.929). All samples and calibrants (0.5 µL) were mixed on the MALDI plate with the matrix α-cyano-4-hydroxycinnamic acid (0.5 µL). Data were collected and averaged from 800 laser desorption events. Monoisotopic mass lists were generated with Data Explorer™ (Applied Biosystems) and copied into the Biolynx™ program in Masslynx™ 4.0 (Waters). Matches to subsequences of presegetalin A1 were investigated using the Find Mass program with an allowed mass deviation of 0.5 Da. Masses within 0.2 Da were considered to be matching.

The MALDI-TOF MS analysis for fraction 8 showed prominent peaks corresponding to peptide masses of 1302.7, 1433.8 and 1984.0 which, in turn, correspond to linear peptides with the sequences MSPILAHDVVKPQ (SEQ ID NO: 16), SPILAHDVVKPQ (SEQ ID NO: 17) and GVPVWAFQAKDVENASAPV (SEQ ID NO: 15), respectively. This suggests that cleavage of the QG peptide bond is an important reaction in the biosynthesis of segetalin A. Taken together, the data are consistent with a peptide with the sequence GVPVWAFQAKDVENASAPV (SEQ ID NO: 15) being an intermediate in segetalin A biosynthesis. As well, the data are consistent with the presence of exopeptidase activity. Thus, the pathway from presegetalin A1 to segetalin A shown in FIG. 2 is hypothesized. Presegetalin A1 is suggested to be cleaved initially after position 13, giving rise to presegetalin A1[1,13] and presegetalin A1[14,32]. The latter is then processed, giving rise to segetalin A.

In Vitro Assay to Test PCY1 Activity

The gene corresponding to S. vaccaria PCY1 was cloned and expressed in E. coli with a His-tag. HisPur Cobalt Resin™ (Thermo Scientific) was used for purification of recombinant PCY1. The purified PCY1 was quantified using BCA method (Pierce; http://http://www.piercenet.com/) with BSA as a calibration standard. The in vitro assay contained 20 mM Tris buffer (pH 8.5), 100 mM NaCl, 5 mM DTT, 0.2 mg BSA, and 1.5 µg of substrates (wild type and mutant presegetalins, procured from Bio Basic Inc with >90% purity) and was initiated by the addition of 0.3 µg of PCY1, in a total reaction volume of 100 µl. The assay was incubated at 30° C. for up to 1 h and stopped by placing reactions in dry ice. The assays were lyophilized, re-suspended in methanol, evaporated and re-suspended in 50:50 v/v methanol/water for LC/MS analysis.

LC/MS Analysis of Assays

Ion trap ESI+ LC/MS/MS analysis was used to detect production of cyclic peptides using an Agilent 6320 Ion Trap LC/MS system under default Smart Parameter settings. The analyzer and ion optics were adjusted to achieve proper resolution (Agilent Installation Guide #G2440-90105) using the ESI Tuning Mix (Agilent #G2431A). The mass spectrometer scanned from 50 to 2200 mass units at 8100 mass units $sec^{-1}$ with an expected peak width of 0.35 atomic mass units. For auto MS/MS, the trap isolation width was 4 atomic mass units. The associated Agilent 1200 LC was fitted with a Zorbax 300 EXTEND-C18 column (150×2.1 mm, 3.5 µm particle size) maintained at 35° C. The binary solvent system consisted of 90:10 v/v water/acetonitrile containing 0.1% formic acid and 0.1% ammonium formate (solvent A) and 10:90 v/v water/acetonitrile containing 0.1% formic acid and 0.1% ammonium formate (solvent B). The separation gradient was 90:10 A/B to 50:50 A/B in 3 ml over 20 min.

Example 2

Cloning of PCY1 from Saponaria vaccaria

The scheme in FIG. 2 suggests the possibility of an enzyme that converts presegetalin[14,32] (SEQ ID NO: 15) to segetalin A (SEQ ID NO: 14). To test this, synthetic presegetalin A1[14,32] was obtained by chemical synthesis from the Sheldon Biotechnology Center (McGill University, Montreal, Canada). This was first used to confirm the identification of presegetalin A1[14,32] in the above enzyme assays by LC/MS (data not shown). Synthetic presegetalin A1[14,32] was then tested in assays and shown to give rise to circular segetalin A (data not shown).

With a view towards complete characterization of the enzyme, its purification from plant material was attempted. The enzyme was partially purified from the developing seed extracts using ion-exchange chromatography, hydrophobic interaction chromatography and size exclusion chromatography.

S. vaccaria Developing Seed Extract

All purification steps were performed on ice or at 4° C. Eight grams of frozen Stage 2 embryos were divided into twenty 1.5 mL Eppendorf™ tubes and ground with a small pestle in 500 µL aliquots of 20 mM Tris-HCl (pH 8.0). The resulting slurries were centrifuged twice to fully remove sediment and floating debris from supernatant for 10 min at 12,000 g, and the pooled supernatant of 17 mL was passed through a 25 mm cellulose acetate membrane syringe filter (0.2 µm pore size; VWR International, Mississauga, Canada) followed by three sequential chromatographic separations, as detailed below.

Chromatography

All chromatographic elution was monitored spectrophotometrically at 280 nm. Three separate applications of five mL each of the filtrate (see above) were applied to an anion exchange column (Mono Q 10/100, GE Healthcare Life Sciences, Mississauga, Canada) connected to an Agilent 1100 series HPLC. The column was held at 4° C. and pre-equilibrated with 20 mM Tris-HCl (pH 8.0). The column was eluted with 60 mL of a linear gradient of NaCl (0-1 M) in 20 mM Tris-HCl (pH 8.0) at a flow rate of 1 mL/min. One mL fractions were collected, desalted with Sephadex™ G-25 M PD-10 columns (GE Healthcare Life Sciences, Mississauga, Canada), concentrated in Amicon™ Ultra centrifugal filters (Ultracel™-30K cellulose 30 MWCO; Millipore, Bellerica, Mass., USA) and assayed for the production of segetalin A in the presence of presegetalin A1[14,32]. The active fractions were combined and applied to a hydrophobic interaction perfusion chromatography column with PerSeptive POROS™ 20 HP2 (Bio-Rad Laboratories (Canada) Ltd, Mississauga, Canada) pre-equilibrated with 3 M ammonium sulfate in 20 mM Tris-HCl (pH 8.0) which was eluted with a decreasing linear gradient (3-0 M) of 60 mL ammonium sulfate at a flow rate of 4 mL/min. One mL fractions were collected over 15 min and desalted and concentrated by ultracentrifugation with Amicon™ Ultra centrifugal filters (Ultracel™-30K cellulose 30 MWCO, Millipore, Bellerica, Mass., USA). The resulting fractions were assayed for enzyme activity (segetalin A production). Active fractions were combined and concentrated to 100 µL with Amicon™ Ultra centrifugal 30 MWCO filters. The resulting sample was then applied to a Superose™ 6 10/300 Gel Filtration column (GE Healthcare Life Sciences, Mississauga, Canada) which had been pre-equilibrated with 20 mM Tris-HCl (pH 8.0). Proteins were eluted with 20 mM Tris-HCl (pH 8.0) at a flow rate of 0.2 mL/min for 145 min. One mL fractions were collected, concentrated with Amicon™ Ultracel-10K membrane centrifugal filter units and assayed for enzyme activity. The retention times of standard proteins (thyroglobulin ($M_r$=669,000), ferritin ($M_r$=440,000), catalase ($M_r$=232,000), aldolase ($M_r$=158,000), BSA ($M_r$=67,000), ovalbumin ($M_r$=43,000), chymotrypsinogen ($M_r$=25,000) and ribonuclease A ($M_r$=14,000); GE Healthcare Life Sciences, Mississauga, Canada) were measured in a separate chromatography experiment under identical conditions. The size exclusion chromatography indicated that the relative molecular mass of the enzyme was approximately 90,000 (data not shown).

SDS Polyacrylamide Gel Electrophoresis

Figure 3:
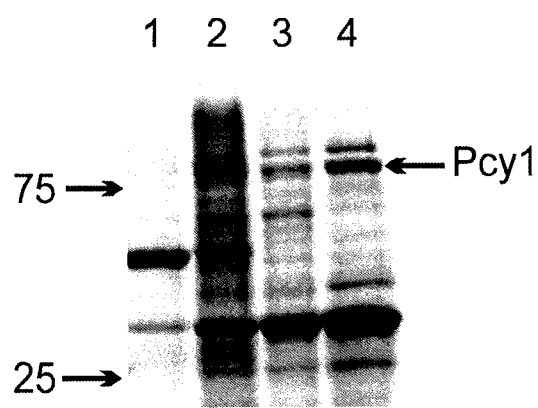
FIG. 3 depicts electrophoretic analysis of partially purified PCY1 from *S. vaccaria*. Lane 1, crude filtrate from *S. vaccaria* developing seed; lane 2, active fraction from anion exchange chromatography; lane 3, active fraction from hydrophobic interaction chromatography; lane 4, active fraction from gel filtration chromatography. The mobility of relative molecular mass standards of 25,000 and 75,000 are shown on the left. Pcy1 indicates a band corresponding to a major protein with $M_r$ of approximately 83,000, for which mass spectral analysis of tryptic peptides was performed.

Active fractions from the various stages of chromatography were mixed 1:1 with SDS PAGE Laemmli sample buffer (200 mM Tris-HCl, pH 6.8, 4% SDS, 0.2% bromophenol blue, 200 mM dithiothreitol, 40% glycerol) and heated at 99° C. for 5 min. The samples were subjected to SDS-PAGE under denaturing conditions in Electrophoresis Buffer (25 mM Tris-HCl, pH 7.5, 250 mM glycine, 0.1% SDS) for 4 h at 30 mA using a 10% Ready Gel™ pre-cast polyacrylamide mini-gel and a Mini-PROTEAN™ II (Bio-Rad Laboratories (Canada) Ltd, Mississauga Canada) apparatus. Precision Plus Protein™ molecular weight standards (Bio-Rad) were loaded on the same gel. The gel was stained with Oriole™ Fluorescent Gel Stain (Bio-Rad Laboratories (Canada) Ltd, Mississauga Canada) for 15 h. Protein bands were visualized by UV illumination (see FIG. 3) and the most prominent bands were excised from the gel and each placed in 1.5 mL Eppendorf™ tubes prior to processing for analysis by mass spectrometry.

Protein Analysis

Gel bands derived from the active fraction of the final chromatography step were subjected to proteolysis and LC/MS as described below. Iodoacetamide (IAA) and dithiothreitol (DTT) were purchased from Bio-Rad (Hercules, Calif., USA); trifluoroacetic acid, ammonium bicarbonate and HPLC grade acetonitrile were purchased from Fisher Scientific (Fair Lawn, N.J., USA). Formic acid was from Acros (New Jersey, USA). Distilled water was purified using a MilliQ™ Element water purification system (Millipore, Billerica, Mass. USA). Sequencing grade modified trypsin (Trypsin Gold) was purchased from Promega (Madison, Wis., USA).

In-Gel Digestion Procedure

Gel bands excised from SDS-PAGE gels were digested using the MassPrep II Proteomics Workstation (Micromass, UK) following a procedure described previously (Sheoran 2005). Briefly, protein gel bands were cut into about 1 mm$^3$ pieces and placed into 96-well plates. Gel bands are destained twice (for 10 min each) with 100 μL of 1:1 (v/v) ammonium bicarbonate:acetonitrile. Protein reduction was performed for 30 min at 37° C. with the addition of a solution containing 10 mM DTT and 0.1 M ammonium bicarbonate. Alkylation was achieved by the addition of 50 μL 55 mM iodoacetamide/0.1 M ammonium bicarbonate and incubation for 20 min at 37° C. Gel pieces were washed with 100 mM ammonium bicarbonate and dehydrated with acetonitrile followed by the addition of saturation with 25 μL of 6 ng/μL trypsin prepared in 50 mM ammonium bicarbonate. Digestion was carried out at 37° C. for 5 h. Peptides were extracted with 30 μL of a solution containing 0.1% trifluoroacetic acid and 3% acetonitrile for 30 min. This step was followed by two extractions with 24 μL of an aqueous solution containing 0.1% trifluoroacetic acid and 50% acetonitrile for 30 min. The combined extracts were lyophilized and reconstituted in 40 μL of a solution containing 0.2% formic acid and 3% acetonitrile prior to analysis by mass spectrometry.

Generation of an Expressed Sequence Tag Collection for *S. vaccaria*

A collection of *S. vaccaria* developing seed expressed sequence tags based on Roche 454 sequencing technology was developed as follows. Stage 1 developing seed embryos were collected and frozen at −80° C. from *S. vaccaria* plants grown under greenhouse conditions at the Plant Biotechnology Institute in Saskatoon, SK, Canada. The protocol of Gambino et al. (Gambino 2008) was modified for the total RNA isolation from *S. vaccaria* developing seeds. For the rapid CTAB-based procedure, 0.6 mL of extraction buffer containing 2% cetyltriethylammonium bromide (CTAB), 2.5% polyvinylpyrrolidone ($M_r$=40,000), 2 M NaCl, 100 mM Tris-HCl, pH 8.0, 25 mM EDTA and 2% of β-mercaptoethanol (added just before use) was heated at 65° C. in a microcentrifuge tube. One hundred and fifty milligrams of developing seeds were ground in liquid nitrogen and added to the extraction buffer and the tube was incubated at 65° C. for 10 min. The sample was extracted two times with chloroform isoamyl alcohol (24:1 v/v) and 0.25 volumes of 3 M LiCl was added. The mixture was kept on ice for 30 min and centrifuged at 20,000 g for 20 min at 4° C. The pellet was resuspended in 0.5 mL of SSTE buffer (10 mM Tris-HCl, pH 8.0, 1 mM EDTA, 1% SDS, 1 M NaCl) and extracted with 0.5 mL of chloroform/isoamyl alcohol (24:1, v/v). Cold isopropanol (0.7 volumes) was added and the sample was centrifuged at 20,000 g for 15 min at 4° C. The pellet was washed with 70% ethanol, dried and resuspended in diethylpyrocarbonate-treated water.

A collection of expressed sequence tags was generated from cDNA prepared from the isolated RNA using Roche (Indianapolis, Ind., USA) GS-FLX Titanium Technology at the McGill and Genome Quebec Innovation Centre (Montreal, Canada) according to the manufacturer's instructions. Within the MAGPIE software system (Gaasterland 1996), sequences were assembled using Mira (Chevreux 2004) and contigs were annotated based on BLASTX searches of Genbank. The EST collection provide the basis for matching mass spectrometry data from tryptic peptides from fractionated seed extracts with cDNA sequences as follows.

Liquid Chromatography/Mass Spectrometry

For LC-ESI-MS analysis, a Quadrupole Time-Of-Flight (Q-TOF) Global Ultima™ mass spectrometer (Micromass, Manchester, UK) equipped with a nano-electrospray (ESI) source and a nanoACQUITY™ UPLC solvent delivery system (Waters, Milford, Mass., USA) was used. The mobile phase was composed from a binary solvent system of A, 0.2% formic acid and 3% acetonitrile and B, 0.2% formic acid and 95% acetonitrile. Peptides were desalted with an in-line solid-phase trap column (180 μm×20 mm) packed with 5 μm resin (Symmetry™ C18, Waters) and separated on a capillary column (100 μm×100 mm, Waters) packed with BEH130 C18 resin (1.7 μm, Waters) using a column temperature of 35° C. An injection volume of 2 to 5 μL was introduced into the trap column at a flow rate of 15 μL/min for 3 min, using A:B 99:1 and flow was diverted to waste. After desalting, the flow was routed through the trap column to the analytical column with a linear gradient of 1-10% solvent B (400 mL/min, 16 min), followed by a linear gradient of 10-45% solvent B (400 mL/min, 30 min). Unless otherwise stated, Q-TOF parameter settings consisted of a capillary voltage of 3,850 V, a cone voltage of 120 V and a source temperature of 80° C.

Samples were analyzed using Data Dependant Acquisition (DDA), which consisted of the detection of multiply charged positive ions (z=2–4) from an MS survey scan. The scan range was from m/z values of 400 to 1900, with a scan time of 1 s. Up to three MS/MS scans were triggered (collision energy ranged from 20 to 80 eV, depending on charge state and precursor m/z) from each MS scan event with a peak detection window of 4 m/z units (signal intensity threshold was 16 counts/s). In MS/MS experiments, data was acquired in continuum mode with a scan time of 1.9 s and dynamic exclusion of previously detected precursors was set at 2 min. Peptide signals corresponding to trypsin and keratin were also excluded from MS/MS data collection. To obtain high mass accuracy, the reference compound leucine enkephalin (80 nM in 1:1 acetonitrile:0.1% aqueous formic acid, Environmental Resource Associates, Arvada, Colo., USA; m/z=556.2771) was continuously introduced to a second ESI source and used for the mass calibration.

Data was processed with ProteinLynx™ Global Server 2.4 (PLGS 2.4, Waters) using RAW files from LC-ESI-MS and LC-ESI-MS/MS. PKL files were generated using ProteinLynx™ Global Server 2.4 (PLGS 2.4, Waters), and subsequently submitted to Mascot™ (Matrix Science Ltd., London, UK) for peptide searches against the NCBI nr database hosted by National Research Council of Canada (NRC, Ottawa) and a local database containing the sequence information from the 454 sequencing of *S. vaccaria* developing seed cDNA. In the database search parameters, a maximum of 1 miscleavage was allowed for tryptic digestion. The tolerance for precursor peptide ions was ±50 ppm and for fragment ions it was ±0.4 Da. Carbamidomethylation of cysteine was selected as a fixed modification and oxidation of methionine was used as a variable modification.

LC-MS/MS data derived from analysis of a trypsinized densely stained protein band corresponding to $M_r$ of approximately 83,000 was used to search a database of *S. vaccaria* expressed sequence tags (EST). The search yielded a match to a set of contiguous cDNAs sequences obtained from 454 sequencing called c272 (from the SVASD1PC EST collection). The mass spectral data corresponded to 21 peptide sequences predicted from the c272 cDNA sequence corresponding to a coverage of 24%. The gene corresponding to c272 was named Pcy1.

Isolation of a Full-Length Pcy1 cDNA from *S. vaccaria*

A DNA plasmid clone of the full length open reading frame of Pcy1 was obtained as follows. First-strand cDNA was synthesized from *S. vaccaria* developing seed total RNA with the Omniscript™ Reverse Transcription Kit (Qiagen, Mississauga, Canada). The protocol for the reverse transcriptase polymerase chain reaction (RT-PCR) was performed according to the manufacturer's instructions using 50 ng/μL of total RNA, 1× Qiagen reaction buffer, 250 μM of each of four dNTPs, 1 μM oligo dT primer, 0.5 U/μL RNase inhibitor, and 0.2 U/μL Omniscript™ reverse transcriptase (Qiagen, Mississauga, Canada) in a final volume of 20 μL. The mixture was incubated for 60 min at 37° C. As recommended by Qiagen, 2 μL of this cDNA mix was used as template for the PCR amplification of full length Pcy1.

Molecular Cloning of Pcy1 cDNA

Gene specific forward (ATG GCG ACT TCA GGA TTC TCG (SEQ ID NO: 19)) and reverse (TCA GTC TAT CCA AGG AGC TTC AAG C (SEQ ID NO: 20)) primers were designed for polymerase chain reaction (PCR) amplification of Pcy1. PCR amplification was performed with a Mycycler™ thermal cycler (Bio-Rad) using the following thermal cycling conditions: Denaturation at 95° C. for 4 min, 35 cycles of 95° C. for 20 s annealing at 54° C. for 30 s, extension at 72° C. for 2.3 min, followed by 10 min at 72° C. The reaction consisted of 0.2 μM forward primer, 0.2 μM reverse primer, 0.2 mM dNTPs, 60 mM Tris-SO$_4$ (pH 8.9), 18 mM ammonium sulfate, 2 mM MgSO$_4$, 0.01 units/μL Platinum™ Taq DNA Polymerase High Fidelity (Invitrogen, Life Technologies, Mississauga, Canada), 2 μL *S. vaccaria* cDNA in a total volume of 50 μL. The PCR products were separated by gel electrophoresis using a 0.8% Ultra™ Pure agarose gel (Invitrogen, Life Technologies, Mississauga, Canada). The PCR reaction produced a single DNA band of approximately 2.2 kb. The PCR product corresponding to this band was purified with the QIAquick™ PCR Purification Kit (Qiagen, Mississauga, Canada). Two μL of the purified PCR product was recombined with pCRB/GW/TOPO™ using a TA Cloning™ Kit (Invitrogen, Life Technologies, Mississauga, Canada) according to the manufacturer's instructions. The resulting plasmid was used to transform ONE SHOT™ TOP 10 competent *E. coli* cells (Invitrogen, Life Technologies, Mississauga, Canada) which were then grown overnight on Luria broth (LB) agar plates containing 100 μg/mL spectinomycin. Colony PCR, using the gene-specific open reading frame primers was used to screen for positive clones, which were then sequenced with T7 forward and reverse primers to verify the insert direction and sequence identity with respect to the c727 contig identified as putative Pcy1. Sequencing confirmed that the clone pCB006 contains a full length Pcy1 ORF (see FIG. 4 (SEQ ID NO: 1)) which is 2175 bp long and encodes a 725-amino acid protein PCY1 (see FIG. 5 (SEQ ID NO: 2)) with a predicted relative molecular mass of 82,400. A BLASTP search of Genbank with the predicted amino acid protein sequence of Pcy1 revealed greatest sequence identity with members of the enterase lipase superfamily (COG1505). In particular, PCY1 shows highest amino acid sequence identity to predicted gene products from *Vitis vinifera* (Genbank accession number CAN70125; 64% sequence identity) and *Populus trichocarpa* (Genbank accession number XP_002890385; 62% sequence identity). Further sequence analysis strongly suggests placement of PCY1 within the S9A family of serine peptidases.

Example 3

*E. coli* Expression and Purification of PCY1

In pCB008, which is derived from pCB006, the Pcy1 ORF is arranged in-frame with an N-terminal His$_6$-tag sequence. Overnight 1 mL LB cultures of *E. coli* BL21-AI™ cells containing 100 μg/mL ampicillin were used to inoculate 100 mL of Overnight Autoinduction Medium (Studier 2005) containing 100 μg/mL ampicillin which was incubated at 37° C. with shaking until an OD$_{600}$ of 0.4 was reached. Arabinose was then added at a concentration of 0.2% and culture growth was continued at 16° C. with agitation overnight. The cultures were centrifuged in 10 mL aliquots in 15 mL polypropylene tubes at 2,000×g at 4° C. for 10 min and the resulting cell pellets were frozen at −20° C. The pellets were resuspended in chilled 500 μL of B-Per™ Bacterial Protein Extraction Reagent (Pierce Biotechnology, Rockford, Ill., USA), then transferred to two 1.5 mL Eppendorf™ tubes for cell lysis at room temperature for 20 min. Lysis was promoted with 3 sonications for 2 min. The lysed pellet was then centrifuged (12,000 g, 4° C., 8 min) and the supernatant (soluble fraction) was mixed with an equal volume of Equilibration/Wash Buffer (50 mM sodium phosphate, 300 mM NaCl, 10 mM imidazole, pH 7.4) and added to 250 μL HisPur™ Cobalt Resin (Peirce Biotechnology, Rockford, Ill., USA) for a batch style immobilized metal affinity purification of PCY1. The Eppendorf™ tubes with the supernant and agarose resin were incubated for 30 min at 4° C. on a rotator to bind the PCY1 protein. The tubes were centrifuged at 700 g and 5 washes were performed with Equilibration/Wash Buffer which was monitored for decreasing OD$_{280}$. The bound PCY1 was eluted with Equilibration buffer with imidazole concentrations of 150 mM and 300 mM in a stepwise fashion. Each eluate was concentrated to 150 μL and desalted by spin dialysis (Amicon Ultra-15 devices; Millipore, Bellerica, Mass.) following the manufacturer's protocol. Concentrated fractions were assayed for enzyme activity (production of segetalin A) and separated by SDS PAGE. The resulting gels were stained with Oriole™(Bio-Rad). The recombinant PCY1 was eluted with 150 mM imidazole and appeared to be about 90% pure.

Use of Recombinant PCY1 to Produce Cyclic Peptide

Figure 6:
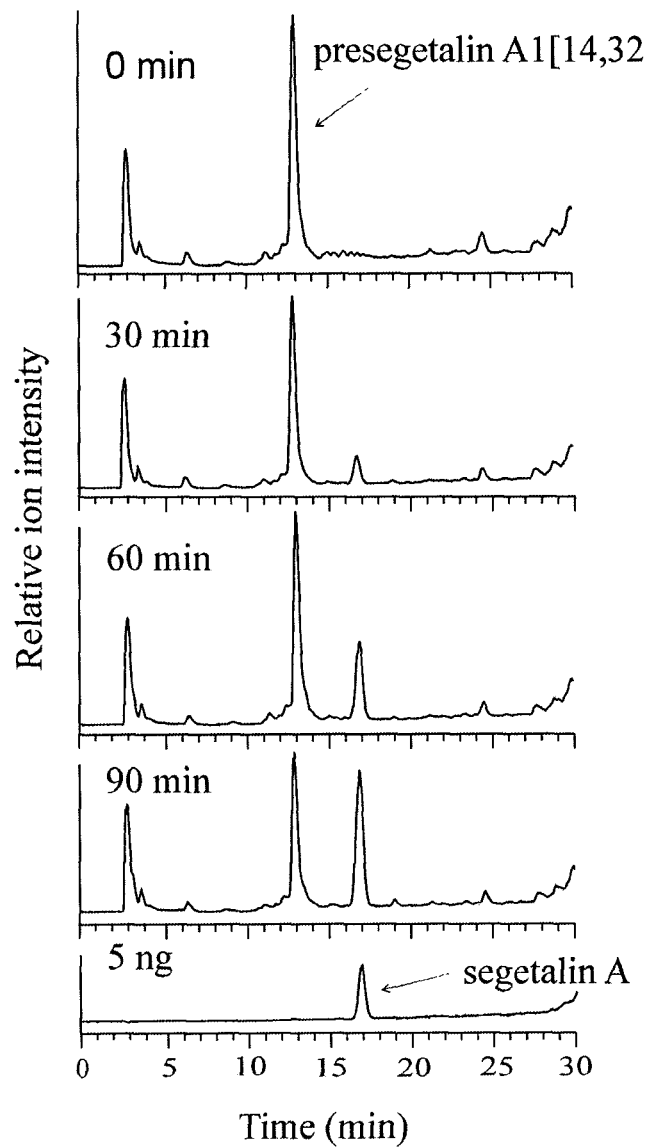

For functional characterization of PCY1, the recombinant enzyme was purified using immobilized metal affinity chromatography (IMAC) from *E. coli* cells harbouring the plasmid pCB008, which comprises Pcy1 in a pDEST™ 17 vector (Invitrogen-Life Technologies, Carlsbad, Calif., USA). The IMAC-purified PCY1 protein was assayed with presegetalin [14,32] followed by LC/MS analysis. Similar to plant extracts, purified PCY1 showed the formation of segetalin A and linear segetalin A in the presence of presegetalin A1[14, 32] (FIG. 6). Control assays without PCY1 enzyme preparation (not shown) and in the absence of presegetalin A1[14,32] did not support the production of segetalin A. The pH optimum of PCY1 was determined to be pH 8.5.

Example 4

*Silene vulgaris* and *Dianthus superbus* Homologues of PCY1

*Silene vulgaris* 454 EST dataset consists of a few hundred thousand short extended sequence tags (ESTs). These were released on Feb. 7, 2011 to the "Short Read Archive" 454: public (SRP005489). A *Silene vulgaris* clone (SEQ ID NO: 21) corresponding to contig c150 has a predicted amino acid sequence (SEQ ID NO: 22), which is 78.5% identical to *S. vaccaria* PCY1. The Silene 454 dataset is also available through the BLAST portal of the PhytoMetaSyn webpage. Further, there are two other similar *S. vulgaris* EST datasets in the Short Read Archive (https://trace.ddbj.nig.ac.jp/DRASearch/query?organism=Silene%20vulgaris) and the University of Virginia has a BLAST portal to their *Silene vulgaris* dataset (http://silenegenomics.biology.virginia.edu/search.html) from which a contig sequence with 99% amino acid sequence identity to c150 can be found. To date, there has been no disclosure of the activity of the *S. vulgaris* c150 contig.

*Dianthus superbus* 454 EST dataset contains contigs c250 (SEQ ID NO: 23) and c1141 (SEQ ID NO: 25) having predicted amino acid sequences (SEQ ID NO: 24) and (SEQ ID NO: 26), respectively, which are 79% and 77.9% identical to *S. vaccaria* PCY1, respectively. The *Dianthus* 454 dataset is available through the BLAST portal of the PhytoMetaSyn webpage. There is also a *Dianthus superbus* 454 EST dataset from another institution in the "Short Read Archive", 454: public (ERP000371) (https://trace.ddbj.nig.ac.jp/DRASearch/query?organism=Dianthus+superbus&study_type=&center_name=&platform=&show=20&sort=Study). To date, there has been no disclosure of the activity of the *D. superbus* c250 and c1141 contigs.

Figure 7:
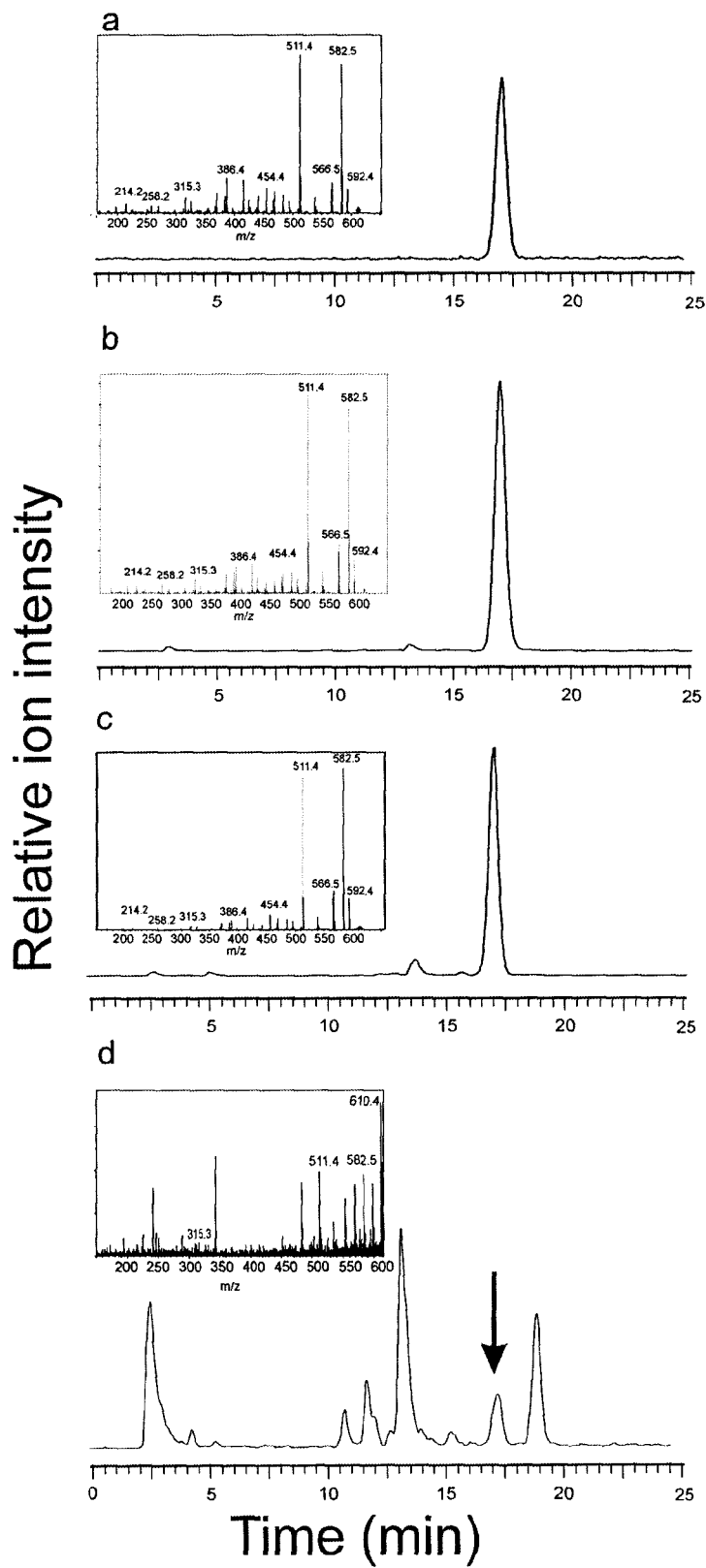
Figure 8:
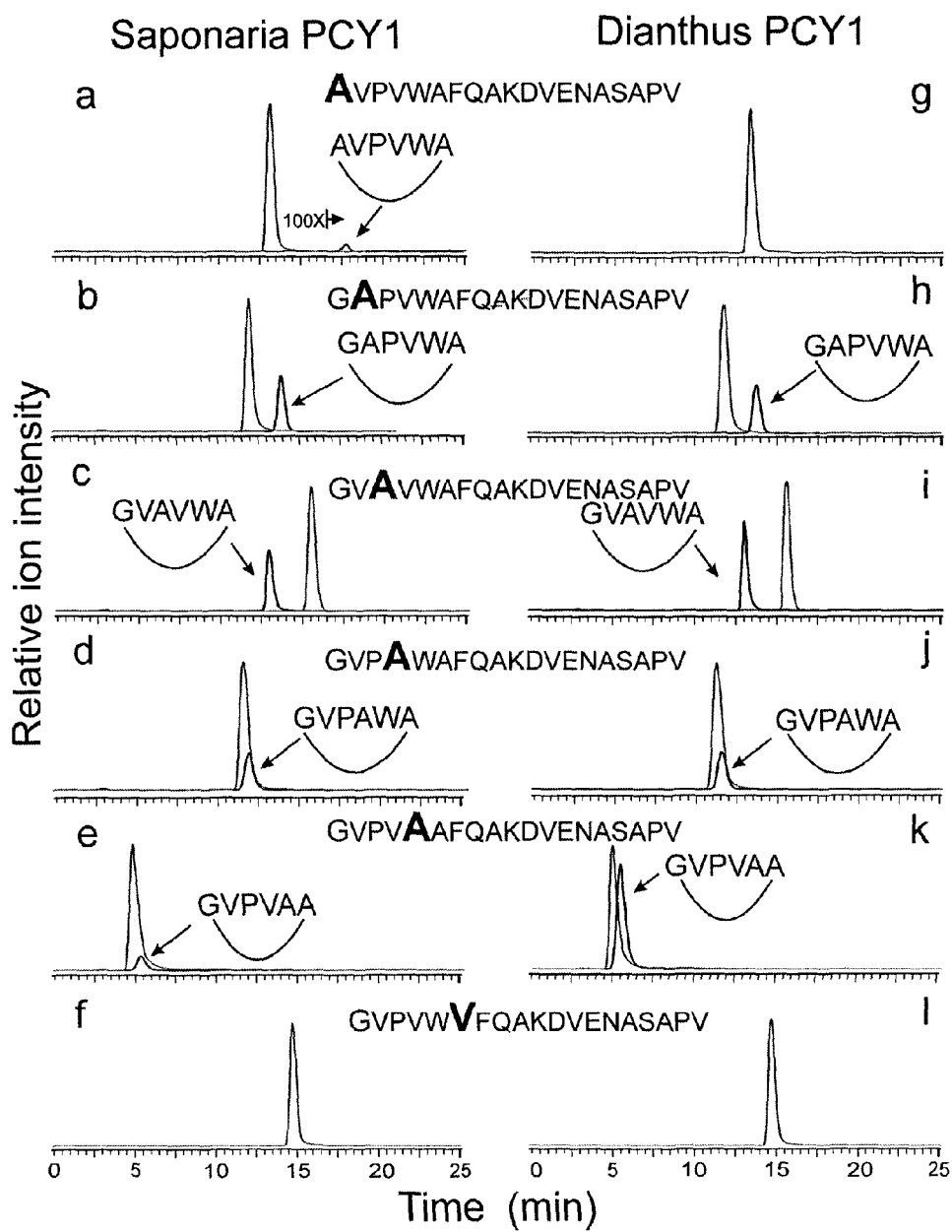
Figure 9:
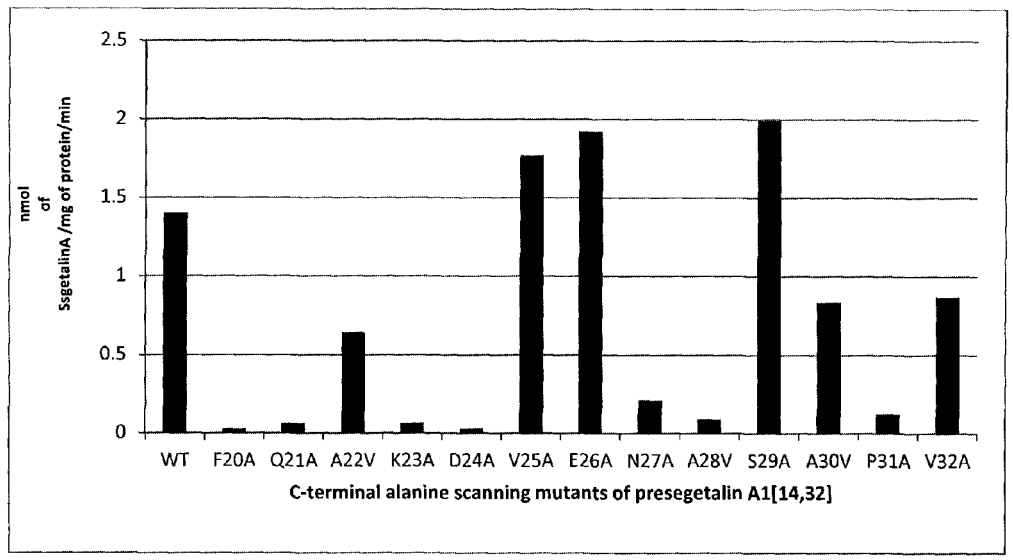
Figure 10:
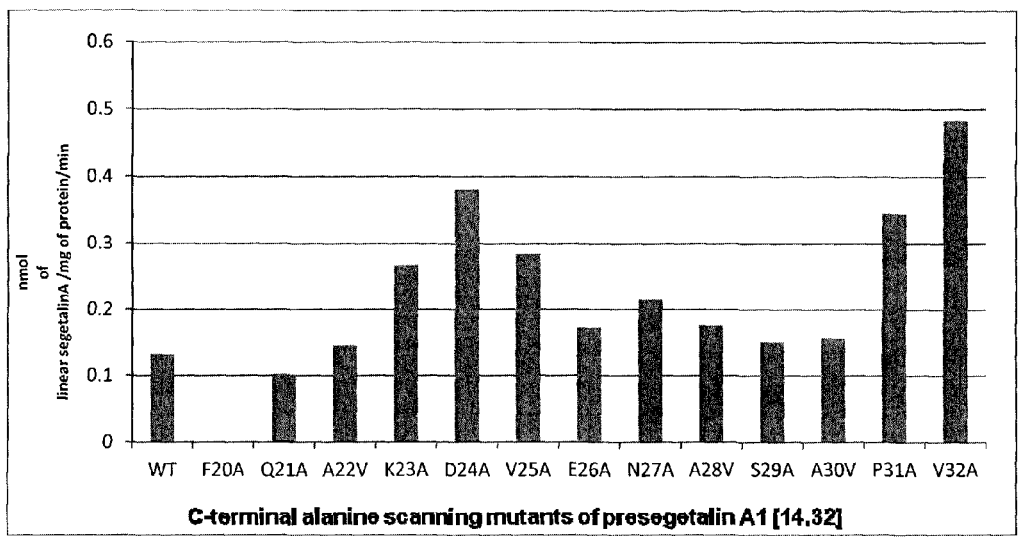
Figure 11:
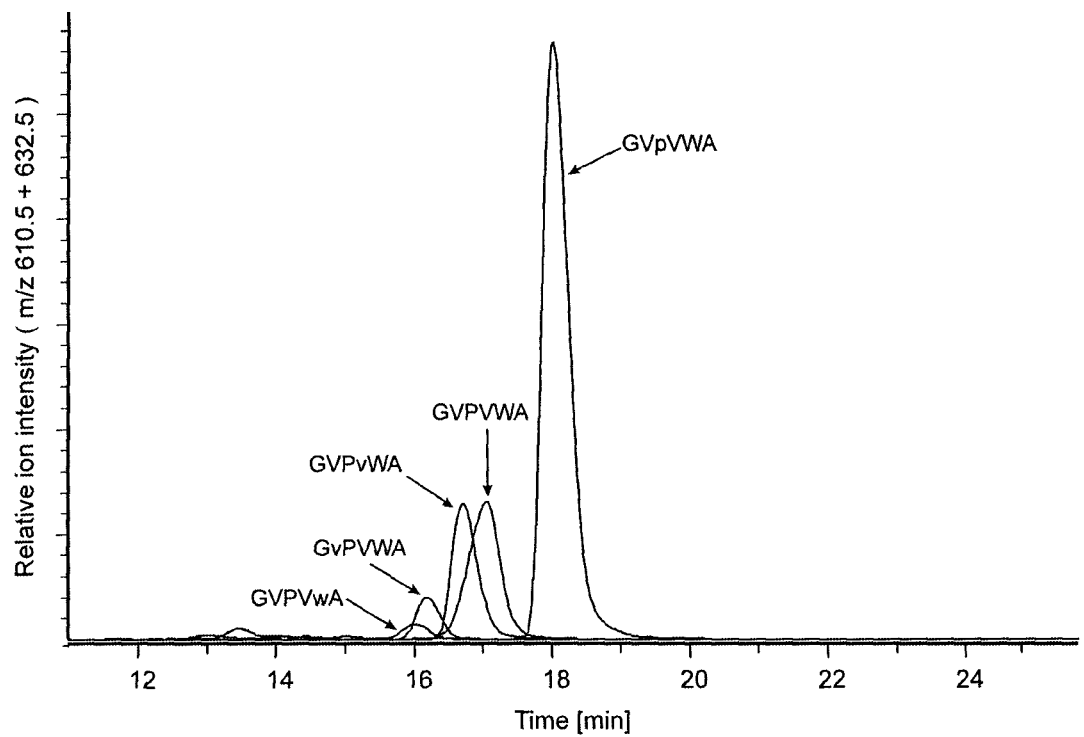
Figure 12:
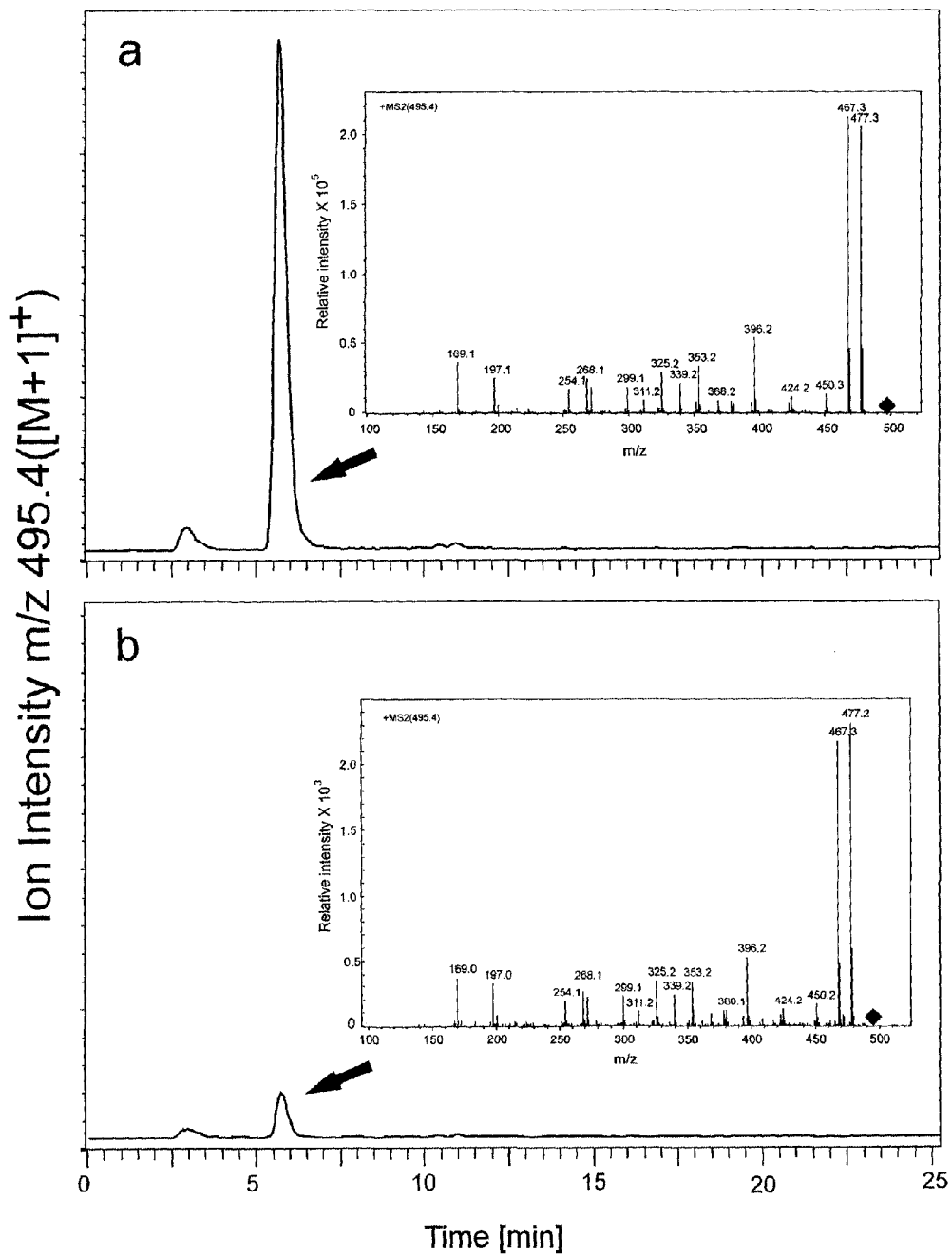

To test for activity of the homologues of *S. vaccaria* PCY1, two cDNAs encoding were cloned from *Dianthus superbus* (c250 and c1141 contigs) and one from *Silene vulgaris* (c150 contig) essentially as described for *Saponaria vaccaria* PCY1 in Example 2. These were named *Dianthus superbus* Pcy1-c250, *Dianthus superbus* Pcy1-c1141 and *Silene vulgaris* Pcy1-c150, Briefly, gene specific forward and reverse primers were used to PCR amplify the aforementioned contigs based on homologue identification in EST collections from *Dianthus* leaves and Silene roots. The *Dianthus superbus* (c250 and c1141 contigs) and *Silene vulgaris* (c150 contig) PCY1 homologues were assayed with 15 µg/mL presegetalin A1[14,32] in vitro as previously described for semi-purified plant extracts to determine whether they can catalyze the production of segetalin A from presegetalin A1[14,32]. The assays were initiated by the addition of 120 ng (c250), or 138 ng (c1141) purified recombinant *Dianthus superbus* or 4 µg *Silene vulgaris* Pcy1 respectively, in a total reaction volume of 100 µL. As shown in FIG. 7d, it has now been found that the polypeptide encoded by *Silene vulgaris* c150 has the same enzymatic activity as that of *S. vaccaria* PCY1, (FIG. 7d) albeit weaker than that of *S. vaccaria* PCY1 for production of segetalin A (compare FIG. 7b), and that the two polypeptides encoded by *Dianthus superbus* c250 and c1141 clones respectively, show strong enzymatic activity (FIG. 7c and FIG. 8 *g-l* (c250) (not shown (c1141)) similar to that of *S. vaccaria* PCY1 (compare FIG. 7b and FIG. 8 *a-f*). *Dianthus superbus* (c1141) PCY1 also demonstrated the ability to cyclize alternating D- and L-amino acid polypeptide substrates (FIG. 12a) in a similar manner to *S. vaccaria* PCY1 (compare FIG. 12b). Thus, there are additional enzymes in the Caryophyllaceae family, which have the same enzymatic activity as *S. vaccaria* PCY1.

Example 5

Substrate Specificity of *Saponaria* and *Dianthus* PCY1

In order to characterize substrate specificity of PCY1 and understand the segetalin A biosynthetic mechanism, a total of 44 substrates (Table 3) were tested for the PCY1 activity and the results are briefly summarized in Table 3. The last two columns in Table 3 summarize product type detected by LC/MS after in vitro assays (CP is cyclic peptide and LP is linear peptide, +=presence, −=absence, NA=not applicable). The 44 substrates were classified as follows:

(A) Presegetalin A1 [14,32], a wild type (WT) precursor of segetalin A
(B) Truncated mutants of presegetalin A1[14,32]
(C) Alanine scanning mutants corresponding to variants of the mature segetalin A sequence
(D) Alanine scanning mutants of the C-terminal region of presegetalin A1[14,32]
(E) D-amino acid mutants corresponding to variants of the mature segetalin A sequence
(F) Insertion mutants corresponding to variants of the mature segetalin A sequence
(G) Other A-class and F-class presegetalins
(H) Putative cyclic peptide precursors from *Dianthus caryophyllus*

TABLE 3

| Substrates tested for cyclization by *S. vaccaria* PCY1 | | | | |
|---|---|---|---|---|
| No. | Peptide Name | Peptide sequence | CP | LP |
| (A) Presegetalin A1[14,32], a wild type (WT) precursor of segetalin A | | | | |
| 1 | Presegetalin A1[14,32] | GVPVWA-FQAKDVENASAPV (SEQ ID NO: 15) | + | + |
| (B) Truncated mutants of presegetalin A1 [14,32] | | | | |
| 2 | Presegetalin A1[14,30] | GVPVWA-FQAKDVENAPV (SEQ ID NO: 38) | − | + |
| 3 | Presegetalin A1[14,28] | GVPVWA-FQAKDVENA (SEQ ID NO: 39) | − | + |
| 4 | Presegetalin A1[14,24] | GVPVWA-FQAKD (SEQ ID NO: 40) | − | + |
| 5 | Presegetalin A1[14,20] | GVPVWA-F (SEQ ID NO: 41) | − | − |
| 6 | Presegetalin A1[14,19] | GVPVWA (SEQ ID NO: 42) | − | NA |

TABLE 3-continued

| Substrates tested for cyclization by *S. vaccaria* PCY1 | | | | |
|---|---|---|---|---|
| No. | Peptide Name | Peptide sequence | CP | LP |
| (C) Alanine scanning mutants corresponding to variants of the mature segetalin A sequence | | | | |
| 7 | Presegetalin A1[14,32]G14A | A-VPVWA-FQAKDVENASAPV (SEQ ID NO: 32) | + | + |
| 8 | Presegetalin A1[14,32]V15A | G-A-PVWA-FQAKDVENASAPV (SEQ ID NO: 33) | + | + |
| 9 | Presegetalin A1[14,32]P16A | GV-A-VWA-FQAKDVENASAPV (SEQ ID NO: 34) | + | + |
| 10 | Presegetalin A1[14,32]V17A | GVP-A-WA-FQAKDVENASAPV (SEQ ID NO: 35) | + | + |
| 11 | Presegetalin A1[14,32]W18A | GVPV-A-A-FQAKDVENASAPV (SEQ ID NO: 36) | + | − |
| 12 | Presegetalin A1[14,32]A19V | GVPVW-V-FQAKDVENASAPV (SEQ ID NO: 37) | − | − |
| (D) Alanine scanning mutants of the C-terminal region of presegetalin A1[14,32] | | | | |
| 13 | Presegetalin A1[14,32]F20A | GVPVWA-A-QAKDVENASAPV (SEQ ID NO: 43) | + | + |
| 14 | Presegetalin A1[14,32]Q21A | GVPVW-AF-A-AKDVENASAPV (SEQ ID NO: 44) | + | + |
| 15 | Presegetalin A1[14,32]A22V | GVPVWA-FQ-V-KDVENASAPV (SEQ ID NO: 45) | + | + |
| 16 | Presegetalin A1[14,32]K23A | GVPVWA-FQA-A-DVENASAPV (SEQ ID NO: 46) | + | + |
| 17 | Presegetalin A1[14,32]D24A | GVPVWA-FQAK-A-VENASAPV (SEQ ID NO: 47) | + | + |
| 18 | Presegetalin A1[14,32]V25A | GVPVWA-FQAKD-A-ENASAPV (SEQ ID NO: 48) | + | + |
| 19 | Presegetalin A1[14,32]E26A | GVPVWA-FQAKDV-A-NASAPV (SEQ ID NO: 49) | + | + |
| 20 | Presegetalin A1[14,32]N27A | GVPVWA-FQAKDVE-A-ASAPV (SEQ ID NO: 50) | + | + |
| 21 | Presegetalin A1[14,32]A28V | GVPVWA-FQAKDVEN-V-SAPV (SEQ ID NO: 51) | + | + |
| 22 | Presegetalin A1[14,32]S29A | GVPVWA-FQAKDVENA-A-APV (SEQ ID NO: 52) | + | + |
| 23 | Presegetalin A1[14,32]A30V | GVPVWA-FQAKDVENAS-V-PV (SEQ ID NO: 53) | + | + |
| 24 | Presegetalin A1[14,32]P31A | GVPVWA-FQAKDVENASA-A-V (SEQ ID NO: 54) | + | + |
| 25 | Presegetalin A1[14,32]V32A | GVPVWA-FQAKDVENASAP-A (SEQ ID NO: 55) | + | + |
| (E) D-amino acid mutants corresponding to variants of the mature segetalin A sequence | | | | |
| 26 | Presegetalin A1[14,32]V15v | G-v-PVWAFQAKDVENASAPV (SEQ ID NO: 56) | + | + |
| 27 | Presegetalin A1[14,32]P16p | GV-p-VWAFQAKDVENASAPV (SEQ ID NO: 57) | + | − |
| 28 | Presegetalin A1[14,32]V17v | GVP-v-WAFQAKDVENASAPV (SEQ ID NO: 58) | + | − |

TABLE 3-continued

Substrates tested for cyclization by S. vaccaria PCY1

| No. | Peptide Name | Peptide sequence | CP | LP |
|---|---|---|---|---|
| 29 | Presegetalin A1[14,32]W18w | GVPV-w-A-FQAKDVENASAPV (SEQ ID NO: 59) | + | + |
| 30 | Presegetalin A1[14,32]A19a | GVPVW-a-FQAKDVENASAPV (SEQ ID NO: 60) | − | − |
| 31 | Presegetalin A1[14,32] P16p W18A | G-V-p-VAA-FQAKDVENASAPV (SEQ ID NO: 61) | + | − |
| 32 | Presegetalin A1[14,32] P16p W18a | G-V-p-V-a-A-FQAKDVENASAPV (SEQ ID NO: 62) | + | − |
| (F) Insertion mutants corresponding to variants of the mature segetalin A sequence | | | | |
| 33 | Presegetalin A1[14,32] ins 16A17 | GVP-A-VW-AFQAKDVENASAPV (SEQ ID NO: 63) | + | + |
| 34 | Presegetalin A1[14,32] ins 16AAA17 | GVP-AAA-VW-AFQAKDVENASAPV (SEQ ID NO: 64) | + | + |
| (G) Other A-class and F-class presegetalins | | | | |
| 35 | Presegetalin B1[14,31] | GVAWA-FQAKDVENASAPV (SEQ ID NO: 65) | + | − |
| 36 | Presegetalin D1[14,31] | GLSFAFP-AKDAENASSPV (SEQ ID NO: 66) | + | + |
| 37 | Presegetalin D1[14,31]P20Q | GLSFA-F-Q-AKDAENASSPV (SEQ ID NO: 67) | + | − |
| 38 | Presegetalin G1[14,31] | GVKYA-FQPKDSENASAPV (SEQ ID NO: 68) | + | − |
| 39 | Presegetalin H1[14,31] | GYRFS-FQAKDAENASAPV (SEQ ID NO: 66) | + | − |
| 40 | Presegetalin L1[14,32] | GLPGWP-FQAKDVENASAPV (SEQ ID NO: 70) | + | − |
| 41 | Presegetalin F1[14,38] | FSASYSSKP-IQTQVSNGMDNASAPV (SEQ ID NO: 71) | + | − |
| 42 | Presegetalin J1[14,36] | FGTHGLPAP-IQVPNGMDDACAPM (SEQ ID NO: 72) | + | − |
| (H) Putative cyclic peptide precursors from Dianthus caryophyllus | | | | |
| 43 | Dianthus Precursor A[14,33] | GPIPFYG-FQAKDAENASVPV (SEQ ID NO: 73) | + | − |
| 44 | Dianthus Precursor B[14,32] | GYKDCC-VQAKDLENAAVPV (SEQ ID NO: 74) | − | − |

Presegetalin A1[14,32], a Wild Type (WT) Precursor of Segetalin A

No. 1 in Table 3, presegetalin A1[14,32] is the 19 amino acid WT precursor for S. vaccaria PCY1. The initial 6 amino acids correspond to the mature cyclic peptide, segetalin A. When the PCY1 was tested with its WT precursor, segetalin A and the linear form (linear peptide) of segetalin A were produced. In LC/MS, the cyclic peptide was detected as diagnostic ions m/z 610.5 $(M+H)^+$, 632.5 $(M+Na)^+$ and 648.5 $(M+K)^+$, while the linear peptide was detected as m/z 628.5 $(M+H)^+$ and 650.5 $(M+Na)^+$ diagnostic ions. Furthermore, their presence was confirmed by MS/MS. As the cyclic peptide is the product of interest, the PCY1 activity was defined on the basis of total amount of segetalin A produced. The PCY1 activity under optimized assay condition was measured as 3 nmol/mg of protein/min.

Truncated Peptide Mutants of Presegetalin A1[14,32]

Five truncated peptide mutants were synthesized by removing various sets of amino acids from the C-terminal end of presegetalin A1[14,32] (No. 2 to 6, Table 3) to explore the importance of the C-terminal region of the substrate in the cyclization reaction. Notably, none of the truncated peptide mutants were converted into cyclic peptide by PCY1. However, No. 2, 3 and 4 showed linear peptide formation almost equivalent to the linear peptide formed from the WT substrate (No. 1). The presence of linear peptide was confirmed by MS/MS analysis. These in vitro assay results with truncated peptide mutants helped to build a hypothesis that the last two amino acids (PV) located at the C-terminal end of presegetalin A1[14,32] play an important role in the cyclization reaction.

Figure 13:
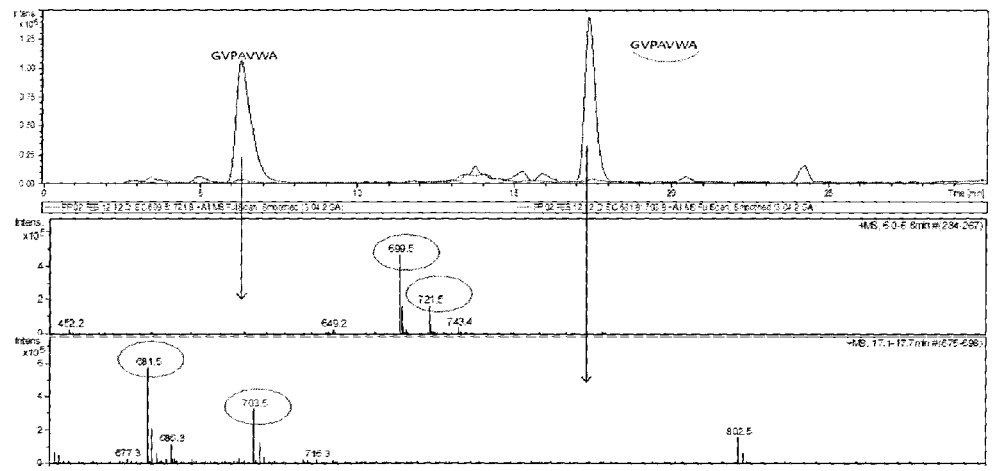
FIG. 13 depicts detection of diagnostic ions in LC/MS for the cyclic peptide and linear peptide products of presegetalin A1[14,32] ins 16A17 (No. 33 in Table 3).
Figure 14:
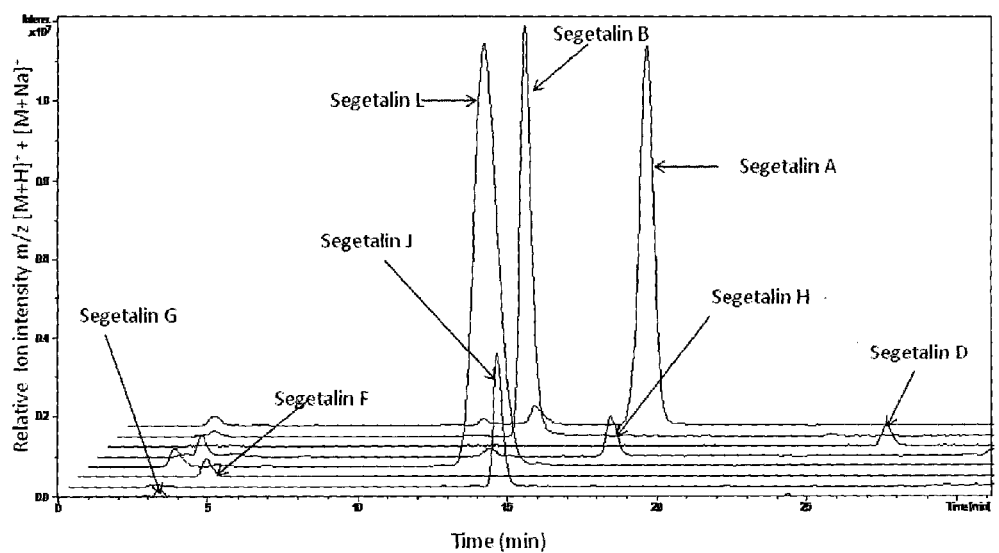
FIG. 14 depicts detection of A- and F-class of segetalins in LC/MS.

Alanine Scanning Mutants Corresponding to Variants of the Mature Segetalin A Sequence Mutants of the part of presegetalin A1[14,32] corresponding to mature segetalin A sequence of segetalin A (No. 7 to 12) were synthesized to determine the importance of each amino acid at particular positions. Each amino acid in segetalin A was replaced with alanine consecutively, and the alanine in the segetalin A sequence was replaced with valine. In vitro assays with these mutant peptides revealed that the PCY1 from *S. vaccaria* was able to make cyclic peptides from No. 7 to No. 11, however neither cyclic peptide nor linear peptide was detected when alanine was replaced with valine at the extreme C-terminal end of mature cyclic peptide (No. 12; FIG. 8). Due to unavailability of standards for each of the newly formed cyclic peptides, quantification of these cyclic peptides was not possible. Relative intensities of the product (cyclic peptides) in LC/MS suggest that *S. vaccaria* PCY1 makes less product (cyclic peptide) with the substitution of glycine to alanine at the first position in segetalin A (No. 7) than with No. 8 to 11. At the same time, the highest amount of linear peptide product was detected with No. 7.

*Dianthus superbus* PCY1-c250 was also assayed with the alanine scan mutants and the activities were compared with those of *S. vaccaria* PCY1. *D. superbus* PCY1-c250 activity was comparable to that of *S. vaccaria* PCY1 with two notable differences. Firstly, there was no detectable cyclic peptide made from No. 7 by *D. superbus* PCY1-c250, although similar to *S. vaccaria* PCY-1 a large amount of linear peptide was detected. Secondly, *D. superbus* PCY1-c250 appeared to produce relatively more cyclic peptide than did *S. vaccaria* PCY1 from No. 11.

Alanine Scanning Mutants of the C-Terminal Region of Presegetalin A1[14,32]

In vitro assays with truncated mutants suggested the importance of the C-terminal region of presegetalin A1[14,32] in the cyclization of segetalin A. Considering this observation, 13 mutant peptides were designed (No. 13 to 25) by substitution of each amino acid with alanine in the last 13 amino acids of the presegetalin A1[14,32] sequence. When alanine was present in the sequence, it was substituted with valine. All mutant peptides were assayed with *S. vaccaria* PCY1 in optimized assay conditions. In the LC/MS analysis, the cyclic peptide was detected as diagnostic ions m/z 610.5 $(M+H)^+$, 632.5 $(M+Na)^+$ and 648.5 $(M+K)^+$, while linear peptide was detected as m/z 628.5 $(M+H)^+$ and 650.5 $(M+Na)^+$ diagnostic ions. The cyclic peptide and linear peptide products were quantified with a standard curve plotted with known amounts of standards for cyclic peptide and linear peptide, respectively.

The experimental results (FIG. 9) suggest that PCY1 produces segetalin A and its linear form linear peptide from all mutant peptides. However, a comparison of the amount of segetalin A produced from WT substrate with the mutants, 7 positions were found to be sensitive to substitution from a total of 13 tested. Those "sensitive" positions were at the position 20, 21, 23, 24, 27, 28 and 31 in presegetalin A1[14,32] (No. 13, 14, 16, 17, 20, 21 and 24 in Table 3). Furthermore, the two most sensitive positions were 20 (F20A, No. 13) and 24 (D24A, No. 17) for which segetalin A production was found to be ≥42 times lower than the WT substrate (FIG. 9).

Above it was observed that the removal of last two amino acids (PV) from presegetalin A1[14,32] prevented cyclic peptide formation. When these last two amino acids were substituted separately with alanine, the P31A mutant (No. 24 in Table 3) was found to yield □11 times less segetalin A than that produced from the WT substrate. On the basis of the activity of *S. vaccaria* PCY1 on substrates previously discussed, it would appear that the proline at position 31 in presegetalin A1[14,32] is a critical amino acid in the cyclization reaction.

At the same time, it is important to note that the substitutions at positions 25, 26 and 29 (No. 18, 19 and 22) yielded relatively higher amounts of segetalin A than that produced from WT substrate. The maximum increase in segetalin A production was observed for the S29A mutant (No. 22 in Table 3), which yielded a 30% increase in segetalin A production relative to wild type presegetalin A1[14,32].

The effect of alanine scanning showed less dramatic differences in linear peptide (linear segetalin A) production when compared to those observed with the cyclic peptide (segetalin A) production. *S. vaccaria* PCY1 showed a relative increase in production of linear segetalin A from all mutant substrates except with No. 13 and No. 14 when compared to that from WT (FIG. 10).

D-Amino Acid Mutants Corresponding to Variants of the Mature Segetalin A Sequence Gadhiri et al. (Gadhiri 1993) and Hourani et al. (Hourani 2011) have reported that cyclic peptides containing an even number of amino acids with the alternating D- and L-chirality are able to form nanotubes, some of which have antimicrobial activity and other interesting commercial properties. Given this, it was of interest to see whether D-amino acids can be tolerated in the presegetalin A1[14,32] so as to give rise to segetalin A with variant stereochemistry.

Seven mutant peptides containing D-amino acids were synthesized (No. 26 to 32 in Table 3) and tested with *S. vaccaria* PCY1 under optimized in vitro conditions. In initial experiments, each amino acid corresponding to segetalin A was substituted with its D-amino acid consecutively from position 15 to 19 (No. 26 to 30). Glycine at position 14 is achiral and no substitution was required. In vitro assay results revealed that the PCY1 can tolerate all L- to D-substitutions except at position 19 (No. 30) where neither cyclic peptide nor linear peptide were detected in the LC/MS analysis (FIG. 11). From these results, it appeared that the initial 5 positions are not sensitive to L- to D-amino acid substitution and it may be possible to generate cyclic peptides with alternating D- and L-amino acids using *S. vaccaria* PCY1. To test this possibility two peptides were synthesized No. 31 and No. 32 in Table 3. In No. 31 and No. 32, a tryptophan (W) at the 18th position of the WT substrate was replaced with alanine, because the W18w mutant of presegetalin A1 was apparently relatively weakly converted to cyclic peptide. In in vitro assays, *S. vaccaria* PCY1 and *D. superbus* PCY1-c1141 made cyclic peptides from both No. 31 and No. 32 (Table 3). The cyclic peptides were detected as diagnostic ions $(M+H)^+$ and $(M+Na)^+$ in LC/MS and their presence was further confirmed by MS/MS analysis. It is noteworthy that *D. superbus* PCY1-c1141 was relatively more active on No. 32 than was *S. vaccaria* PCY1 (FIG. 12). The cyclic peptide produced from No. 32 has alternating D- and L-forms of amino acids (with the exception of the glycine), which gives it the potential to self-assemble into nanotube under appropriate conditions (Gadhiri 1993).

Insertion Mutants Corresponding to Variants of the Mature Segetalin A Sequence

The largest known Caryophyllaceae-like cyclic peptide (Stelladein A, cyclo-(PPPLLGPPYYG)-; SEQ ID NO: 75) is made up 11 amino acids according to Tan and Zhou (Tan 2006). This fact led us to investigate whether PCY1 can produce versions of segetalin A with extra amino acids.

A mutant peptide was synthesized with insertion of an extra alanine between position 16 and 17 (No. 33) in presegetalin A1[14,32] and assayed with PCY1. The cyclic peptide and linear peptide with 7 amino acids were both detected with LC/MS analysis of the in vitro assay. The cyclic peptide with additional alanine cyclo-(GVPAVWA) (SEQ ID NO: 76) was detected as diagnostic ions m/z 681.5 (M+H)$^+$ and 703.5 (M+Na)$^+$ while the linear peptide was detected as m/z 699.5 (M+H)$^+$ and 721.5 (M+Na)$^+$ (FIG. 13).

As an insertion of one alanine in presegetalin A1[14,32] was tolerated, a modified presegetalin A1[14,32] peptide with three alanine insertions between position 16 and 17 was synthesized (No. 34 in Table 3) and tested with *S. vaccaria* PCY1 for its ability to produce the cyclized 9 amino acid product. The LC/MS analysis confirmed that PCY1 produced the expected 9 amino acid cyclic peptide (confirmed by MS/MS analysis) and linear peptide products from No. 34 This result demonstrates that *S. vaccaria* PCY1 can tolerate three extra amino acids.

Other A-Class and F-Class of Presegetalins

There are 9 different segetalins, divided into two groups which were designated A- and F-class segetalins. The A-class includes segetalins A, B, D, G, H, K and L while the F-class includes segetalins F and J (No. 41 and 42). The A-class cyclic peptides are comprised of 5 to 7 amino acids, of which glycine is the first amino acid in the corresponding presegetalin. In contrast, the F-class cyclic peptides are comprised of 9 amino acids, of which phenylalanine is the first amino acid in the corresponding.

Of the 8 presegetalins (No. 1, 35, 36, 38, 39, 40, 41 and 42, Table-3) assayed with *S. vaccaria* PCY1, cyclic peptide products were detected from all of them (FIG. 14). The production of cyclic peptides and linear peptides were confirmed by the presence of expected diagnostic ions $(M+H)^+$ and/or $(M+Na)^+$ in LC/MS. The F-class segetalins (F and J) were further confirmed by MS/MS analysis. Due to unavailability of standards for each of these segetalins, cyclic peptides and linear peptides produced during in vitro assays were not quantified except for segetalin A.

In addition, proline at the 20$^{th}$ position was replaced with glutamine in presegetalin D1[14,31] sequence (No. 37) and assayed with *S. vaccaria* PCY1 as a substrate candidate. Interestingly, the proline to glutamine substitution in No. 37 resulted in a 5 amino acid cyclic peptide product (cyclo (GLSFA); SEQ ID NO: 77), and the substituted glutamine was not part of the final cyclic peptide.

Cyclic Peptide Precursors from a *Dianthus caryophyllus*

Condie et al. (Condie 2011) had reported two putative cyclic peptide precursors from *Dianthus caryophyllus*. The amino acid sequences of these two precursors (No. 43 and 44 in Table 3) appeared to be similar to the A-class segetalin precursors. The activity of *S. vaccaria* PCY1 was tested on No. 43 and 44. Analysis of the assays indicated there was a small amount of cyclic peptide production from No. 43 but none from No. 44. The cyclic peptide produced from No. 43 was detected by LC/MS as diagnostic ions as m/z 732.5 $(M+H)^+$ and m/z 754.5 $(M+Na)^+$ and its presence was further confirmed by MS/MS analysis.

Free Listing of Sequences:

ORF of Pcy1-consensus cDNA (2172 nt) encoding PCY1 (*S. vaccaria*)
SEQ ID NO: 1

```
ATGGCGACTTCAGGATTCTCGAAACCGCTGCATTATCCACCGGTTCGCCGCGACGAGACC

GTCGTCGACGATTACTTTGGCGTTAAAGTCGCTGATCCTTACCGTTGGCTAGAGGATCCG

AATTCGGAGGAGACGAAGGAATTCGTGGATAATCAGGAAAAACTCGCGAATTCAGTGCTT

GAAGAATGCGAGTTGATAGACAAATTCAAGCAAAAAATCATTGATTTTGTTAATTTTCCG

CGGTGTGGCGTGCCGTTTAGGCGTGCCAACAAGTATTTTCACTTCTATAATTCCGGCCTT

CAAGCGCAAAATGTTTTTCAGATGCAGGATGATTTGGACGGAAAGCCAGAGGTGCTATAC

GATCCTAATCTTAGAGAGGGTGGACGATCCGGTTTGAGCCTGTATTCTGTAAGCGAGGAT

GCCAAATATTTTGCATTTGGTATACATTCAGGTTTGACTGAATGGGTGACTATCAAAATA

TTGAAAACTGAAGACCGGAGCTATTTACCCGACACTTTAGAGTGGGTGAAGTTTAGTCCT

GCCATCTGGACTCATGACAATAAAGGATTTTTCTATTGCCCGTATCCACCCCTCAAGGAA

GGAGAAGATCATATGACTCGTTCTGCCGTCAATCAAGAGGCAAGATATCATTTTTTGGGT

ACTGACCAGTCCGAAGATATTTTGTTGTGGAGAGACCTTGAGAACCCCGCACATCACTTA

AAGTGCCAGATAACTGATGACGGAAAGTATTTTCTTCTCTACATTCTGGACGGCTGTGAT

GATGCGAACAAAGTATACTGTTTGGATTTAACAAAGCTGCCTAATGGGCTTGAAAGTTTC

CGGGGGAGAGAAGACTCAGCTCCTTTCATGAAGCTTATCGATAGTTTTGATGCATCATAT

ACAGCCATTGCTAATGATGGCTCTGTGTTTACATTTCAAACTAATAAGGATGCGCCCAGA

AAAAAGTTAGTTCGTGTTGATTTGAATAATCCCAGTGTATGGACTGATCTCGTTCCAGAG

TCGAAGAAGGATTTGCTTGAATCAGCACATGCTGTCAATGAAAACCAGCTTATTCTCCGT

TACCTAAGTGATGTCAAACATGTTCTGGAGATTAGAGATCTTGAAAGTGGCGCTCTGCAG

CATCGCTTACCCATCGACATTGGATCTGTTGATGGTATTACTGCACGACGAAGAGACAGT

GTCGTGTTTTTTAAGTTTACAAGTATCCTGACTCCTGGCATTGTTTATCAATGTGATTTG
```

```
AAAAATGATCCTACACAGTTGAAGATCTTCAGAGAAAGTGTGGTCCCTGATTTTGATCGT

TCCGAGTTTGAAGTTAAGCAGGTTTTTGTGCCCAGCAAAGATGGCACAAAGATACCAATA

TTTATAGCGGCAAGAAAGGGAATATCTTTGGATGGATCACACCCATGTGAAATGCATGGT

TATGGCGGGTTTGGCATAAACATGATGCCAACTTTTTCCGCCAGTCGCATAGTATTTCTG

AAGCACCTAGGTGGCGTCTTCTGCTTGGCTAATATCCGAGGTGGGGGTGAATACGGAGAG

GAATGGCATAAGGCAGGATTTCGCGATAAGAAGCAAAACGTTTTTGATGACTTCATCTCT

GCAGCCGAGTATCTTATTTCCAGTGGCTATACCAAGGCTAGAAGAGTGGCTATTGAAGGT

GGTAGTAATGGTGGCCTTCTCGTTGCTGCTTGTATTAATCAGAGACCAGACCTTTTCGGT

TGTGCTGAAGCAAACTGTGGTGTTATGGACATGCTTCGATTCCATAAATTTACCCTTGGT

TATCTTTGGACGGGAGACTATGGATGCTCCGACAAAGAGGAAGAATTCAAATGGCTTATC

AAGTACTCACCGATTCATAACGTGAGGAGGCCATGGGAACAACCAGGGAACGAAGAGACA

CAATACCCTGCTACTATGATATTGACAGCTGATCACGACGATCGTGTCGTGCCACTGCAC

TCGTTTAAATTGCTGGCTACTATGCAGCATGTTTTGTGCACAAGTTTGGAGGACAGCCCT

CAGAAGAATCCAATAATTGCTCGGATTCAGCGCAAAGCTGCACATTACGGACGTGCCACA

ATGACCCAGATTGCTGAAGTAGCTGATCGGTATGGCTTTATGGCAAAGGCGCTTGAAGCT

CCTTGGATAGAC
```

PCY1 enzyme-(724 aa) encoded by Pcy1 (*S. vaccaria*)
                                              SEQ ID NO: 2
MATSGFSKPLHYPPVRRDETVVDDYFGVKVADPYRWLEDPNSEETKEFVDNQEKLANSVL

EECELIDKFKQKIIDFVNFPRCGVPFRRANKYFHFYNSGLQAQNVFQMQDDLDGKPEVLY

DPNLREGGRSGLSLYSVSEDAKYFAFGIHSGLTEWVTIKILKTEDRSYLPDTLEWVKFSP

AIWTHDNKGFFYCPYPPLKEGEDHMTRSAVNQEARYHFLGTDQSEDILLWRDLENPAHHL

KCQITDDGKYFLLYILDGCDDANKVYCLDLTKLPNGLESFRGREDSAPFMKLIDSFDASY

TAIANDGSVFTFQTNKDAPRKKLVRVDLNNPSVWTDLVPESKKDLLESAHAVNENQLILR

YLSDVKHVLEIRDLESGALQHRLPIDIGSVDGITARRRDSVVFFKFTSILTPGIVYQCDL

KNDPTQLKIFRESVVPDFDRSEFEVKQVFVPSKDGTKIPIFIAARKGISLDGSHPCEMHG

YGGFGINMMPTFSASRIVFLKHLGGVFCLANIRGGGEYGEEWHKAGFRDKKQNVFDDFIS

AAEYLISSGYTKARRVAIEGGSNGGLLVAACINQRPDLFGCAEANCGVMDMLRFHKFTLG

YLWTGDYGCSDKEEEFKWLIKYSPIHNVRRPWEQPGNEETQYPATMILTADHDDRVVPLH

SFKLLATMQHVLCTSLEDSPQKNPIIARIQRKAAHYGRATMTQIAEVADRYGFMAKALEA

PWID

Presegetalin A1-linear polypeptide (32 aa) (*S. vaccaria*)

SEQ ID NO: 3

MSPILAHDVVKPQGVPVWAFQAKDVENASAPV

Presegetalin B1-linear polypeptide (31 aa) (*S. vaccaria*)

SEQ ID NO: 4

MSPILAHDVVKPQGVAWAFQAKDVENASAPV

Presegetalin D1-linear polypeptide (31 aa) (*S. vaccaria*)

SEQ ID NO: 5

MSPIFAHDVVNPQGLSFAFPAKDAENASSPV

Presegetalin D2-linear polypeptide (31 aa) (*S. vaccaria*)

SEQ ID NO: 6

MSPIFAHDVVKPQGLSFAFPAKDAENASSPV

Presegetalin D3-linear polypeptide (31 aa) (*S. vaccaria*)

SEQ ID NO: 7

MSPILAHDVVKPQGLSFAFPAKDAENASSPV

Presegetalin G1-linear polypeptide (31 aa) (S. vaccaria)
SEQ ID NO: 8
MSPIFVHEVVKPQGVKYAFQPKDSENASAPV Presegetalin H1-linear polypeptide (31 aa) (S. vaccaria)
SEQ ID NO: 9
MSPIFAHDIVKPKGYRFSFQAKDAENASAPV Presegetalin K1-linear polypeptide (31 aa) (S. vaccaria)
SEQ ID NO: 10
MSPILALDRYKPEGRVKAFQAKDAENASAPV Presegetalin L1-linear polypeptide (32 aa) (S. vaccaria)
SEQ ID NO: 11
MSPILSHDVVKPQGLPGWPFQAKDVENASAPV Presegetalin F1-linear polypeptide (38 aa) (S. vaccaria)
SEQ ID NO: 12
MATSFQFDGLKPSFSASYSSKPIQTQVSNGMDNASAPV Presegetalin J1-linear polypeptide (36 aa) (S. vaccaria)
SEQ ID NO: 13
MATSFQLDGLKPSFGTHGLPAPIQVPNGMDDACAPM Segetalin A-cyclic polypeptide (6 aa) (S. vaccaria)
SEQ ID NO: 14
GVPVWA Presegetalin A1 [14,32]-linear polypeptide (19 aa) (S. vaccaria)
SEQ ID NO: 15
GVPVWAFQAKDVENASAPV Presegetalin A1[1,13]-linear polypeptide (13 aa) (S. vaccaria)
SEQ ID NO: 16
MSPILAHDVVKPQ Presegetalin A1 [2,13]-linear polypeptide (12 aa) (S. vaccaria)
SEQ ID NO: 17
SPILAHDVVKPQ Presegetalin A1 [20,32]-linear polypeptide (13 aa) (S. vaccaria)
SEQ ID NO: 18
FQAKDVENASAPV Primer (21 bp)
SEQ ID NO: 19
ATGGCGACTTCAGGATTCTCG Primer (25 bp)
SEQ ID NO: 20
TCAGTCTATCCAAGGAGCTTCAAGC contig c150 polynucleotide-(2178 nt) (Silene vulgaris)
SEQ ID NO: 21
ATGGCTTCCTCCGCCTTCTCCAAACCCTTGAACTACCCTCCCGTCCGCCGTGACGAAACC

GTCGTCAATGATTACTTCGGCGTCAAAGTCGCCGATCCTTACCGTTGGCTAGAGGATCAG

GAAGGGGAAGAGACGATAGAGTTTGTAGATAATCAAGTGAAATTGGCTGATTCAGTGCTT

GAAGAATGTGAGTTGAGAGATAAGATCAAGCAGAAAATCACGGATCTTGTCAATTTTCCG

CGTTGCGGTGTGCCGTTTAAGCGTGCTGACAAGTATTTTCATTTTTATAATTCTGGACTT

CAAGCTCAAAATGTGCTTCATATGCAGGATGATTTGGACGGAAAGCCAGAGGTGCTATAT

GATCCTAACCTTAGAGAAGGTGGAAGATCTGGATTGCACCAGTATGCTGTAAGCGAGGAT

GCCAAATATCTCGCGTTTGGTATAAATTCAGGTTTTTCAGAATGGTTGACTATCAAAGTG

ATGAGAATTGAAGACCGGAGTGTTTTACCTGACTCTTTATCATGGGTGAAGTTTAGTGGT

ATTCACTGGACACATGACAGTAAGGGATTTTTCTTTTCCCCATATCCACCCGCCACTGAA

GGACTAGAAGTTGGGATGAAAACTAATTCTAGCTTCAATCAGGAGTTGAGGTATCATTTT

CTTGGTACTGATGAGTCTGAAGACGTTCTGTGCTGGAGAGACCCGGAAAACCCCACACAT

CACTTGAAATCTGATTTAACTGCTGACGGAAAGTATTTACTACTCTATATATCAGCGGGT

TGTGATGCAACGAACAAAGTTTACTATATGGATTTAACAACTTTGCCTAATGGGCTTGAA

-continued

```
GGTTTGCGTGGGGGAAAGGACTTGCTTCCTTTCAAAAGGCTTATTGATGAGTTTGATGCA

ACGTATACAGCTATTGCTAATGATGGCTCTGTGTTTACTTTCCTAACCAACAAGGATGCT

CCAAGAAATAAGATAGTTCGTGTAGATTTGAATAATCCAGACATATGGACTGAGGTGATT

CCAGAGTCTAAGAAGGATGTGCTTGAATCAGCACACGCTGTTAATGGAAACCAACTTCTT

GTCCGTTACCTAAGTGATGTCAAACATATTCTGGAGGTTAGAGATCTAGAGAGTGGCTCT

CTACTGCATCGCTTACCCGTCGACCTCGGAGTTATTGATGGAATCACTGCACGACCACAA

GATAGTGTTGTGTTTTTCAAGTTTACAAGCTTCCTGACTCCTACCATAATTTATCAGTGT

GATTTGAAGGAAGATTCTCCACAGTTAAAGATTTTCCGAGAAAGTGTTGTTCCTGAATTT

GACCGTTCCGAGTTTGAGGTTAAACAGGTGTTTGTATCAGCCAAAGATGGCACAAAGATA

CCAATGTTCATAGTGGCAAGGAAGGGAATATCTTTGGATGGATCACACCCATGTGAACTA

CATGGTTATGGCGGGTTCAGCATATCTATAAAACCATTTTTTTCCGCCAGTCGCATTGTA

ATTTTGAAGCACCTTGATGCCGTCTTCTGCGTGGCTAATATCCGAGGTGGTGGTGAATAT

GGAGAGGAATGGCACCAAGCAGGATGGCGTGAAAAGAAGCAGATTGTTTTTGATGACTTC

ATCTCTTCAGCTGAGTATCTTGTTTCTAGTGGCTATACCCAGCCTCAAAAGTTGAGTATT

GAAGGAGGCAGTAATGGTGGCCTGCTTGTTGCTGCTTGTATTAATCAGAGACCAGACCTT

TTTGGTTGCGCTCAGGCCAATTGCGGTGTAATGGACATGCTTCGATTCCATAAATTTACC

CTCGGTTATCTTTGGACATCGGATTATGGTTGCTCCGAGAAAGAGGAAGATTTTAACTGG

CTTATAAAGTACTCACCGATACATAATGTGAGGAGGCCATGGGAGCACTCAAAGAATCCA

CAGTTACAATACCCTGCTGTTATGATACTGACAGCTGATCATGATGATCGTGTGGTGCCT

CTTCACTCCTTCAAACTGCTGGCTACTTTGCAGCATGTTCTTTGCACAAGTTTAGAGGAC

TCCCCTCAGAAAAATCCAATAATTGCTCGAATTGAGCGCAAAGCATCACACTGTGGGCGT

GCGACGATGAAGCAGATTGATGAAGCTGCAGATCGGTACGCCTTTATGGCCAAGGCGCTT

AGAGCCACTTGGACTGAT
``` contig c150 predicted polypeptide-(726 aa) (*Silene vulgaris*)
SEQ ID NO: 22

```
MASSAFSKPLNYPPVRRDETVVNDYFGVKVADPYRWLEDQEGEETIEFVDNQVKLADSVL

EECELRDKIKQKITDLVNFPRCGVPFKRADKYFHFYNSGLQAQNVLHMQDDLDGKPEVLY

DPNLREGGRSGLHQYAVSEDAKYLAFGINSGFSEWLTIKVMRIEDRSVLPDSLSWVKFSG

IHWTHDSKGFFFSPYPPATEGLEVGMKTNSSFNQELRYHFLGTDESEDVLCWRDPENPTH

HLKSDLTADGKYLLLYISAGCDATNKVYYMDLTTLPNGLEGLRGGKDLLPFKRLIDEFDA

TYTAIANDGSVFTFLTNKDAPRNKIVRVDLNNPDIWTEVIPESKKDVLESAHAVNGNQLL

VRYLSDVKHILEVRDLESGSLLHRLPVDLGVIDGITARPQDSVVFFKFTSFLTPTIIYQC

DLKEDSPQLKIFRESVVPEFDRSEFEVKQVFVSAKDGTKIPMFIVARKGISLDGSHPCEL

HGYGGFSISIKPFFSASRIVILKHLDAVFCVANIRGGGEYGEEWHQAGWREKKQIVFDDF

ISSAEYLVSSGYTQPQKLSIEGGSNGGLLVAACINQRPDLFGCAQANCGVMDMLRFHKFT

LGYLWTSDYGCSEKEEDFNWLIKYSPIHNVRRPWEHSKNPQLQYPAVMILTADHDDRVVP

LHSFKLLATLQHVLCTSLEDSPQKNPIIARIERKASHCGRATMKQIDEAADRYAFMAKAL

RATWTD
``` contig c250 polynucleotide-(2169 nt) (*Dianthus superbus*)
SEQ ID NO: 23

```
ATGGCGTCCTGTGGATTCACTAAACCCTTGCATTATCCTACGGCACGCCGTGACGAAACC

GTCGTCGACGATTACTTCGGCCTCAAAGTCGCCGATCCTTACCGCTGGCTCGAGGATCGG
```

-continued

```
GATTCGGAAGAGACGAAGAAATTCGTGGAGGATCAAGTGAAGTTTACTGATTCAGTGCTT

GAGGAATGCGAGTTGATCGGCAAAGTCAAGCAAAAGATCATAGATTATGTTAGTTTTCCG

CGTTGGAGTGTGCCGCTTAGGCGTGCCAACAAATATTTTCACTTCTATAACTCTGGACTT

CAATCGCAAAATGTTTATCGGATGCAGGATGGTTTGGACGGAAAGCCAGAGGTGATATGT

GATCCTAATCTTAGAGAAGACGGACGAACTGGCTTGAGCGTGTATTCTGTAAGCGAGGAT

GCCAAATATTTTGCATTTGGTATAGCAGAAGGCTTTACTGAATGGCTCACGATTAGAGTA

ATGAGAACGGAAGACCGGAGTATGTTACCCGACTGTTTAACCGAGGTGAAATTTACTACT

GTTCATTGGACGCATGATAATAAAGGATTTTTCTATTGTGCATATCCGCCCCTCGAGGAA

GGACAAGATCATATGGTTCATGCTAGCATCAGTCAAGAGGCGAGATATCATTATCTTGGT

ACAGACCAGTCTGAAGATATTTTGTGCTGGAAAGATCCTGAAAACCCCACACACCACTTC

AGGAGCTATTTTACTGATGACGGAAAGTATTTTGTTCTCTACATTTTAGAGGGATGTGAT

AAGAAGAACAAAGTATACTGTCTGGATTTAACAAAGCTACCTAACGGGCCTGAAAGTCTC

CGAGGGAGAGAAGGCTCAGCTCCTTTCATAAAACTTGTGGATAGTTTTGATGCATCGTAT

ACAGTCATTGCTAATGATGATTCTGTGTTTACACTCCTAACTGATAAGGATGCAAAAGA

TGTAAGTTAGTTCGTGTTGATTTGAATAATCCGAGCGTGTGGACTGATGTGATTCCGGAG

TCCAAGGACTTGCTTGAATCAGCACATGCAGTCAACGGAAACCAGCTTCTTCTTCGTTAC

CTACGTGATGTCAAACATGTACTTGAGCTTAGGGATCTCGAAAGTGGCTCTCTACTACAT

AGCATACCCATAGACATTGGAGCTGTTGATGGTATTAATGCACGACGAGGAGACAGTATC

GTGTTTTTAGGTTTACAAGCATCCTGACTCCTGGCATAATTTATCAATGTGATTTGAAA

AATGATCCTACACAGTTAAATATCTTCAGAGAAAGTCTTGTCCCTGGGTTTGACCGTTCT

GAGTTCGAGGTTAAACAGGTTTTTGTGCCTGGCAAAGATGGAACAAAGATACCAGCATTC

ATAGCAGCAAGAAAGGGAATATCTTTGGATGGATCACATCCATGTGAAATGCATGGCTAC

GGCGGATATGGCCATAATATGATGCCAACTTTTTCCGCCAGTCGCTTAGTATTTTTGAAG

CACCTTGGTGGCGTCTTCTGTTTGGCTAATATTCGAGGTGGTGGTGAATATGGAGTTGAC

TGGCATAAAGCAGGAGCCCGTGAAAACAAGCAAACCAGTTTTGATGACTTCATCTCCTCA

GCTGAGTTTCTTGTTTCTAGTGGCTACAGCGCACCTAAAAAAATTTGTATCGAAGGTGGA

AGTAACGGGGGCCTTCTCATTGCTGTTTGTATTACTCAGAGACCAGACCTGTTCGGTTGT

GCCGAGCCGAACTGTGGTCCTATGGACATGCTTCGATTCCATAAATTTACGCTTGGTTAT

CTTTGGACTGATGAATATGGTAACCCCGACAATGAGGAAGAGTTCAACTGGCTTATCAAG

TACTCACCGCTACACAACGTGAGGAGACCATGGGAACAGCCAGGGCATGAACAGACACAA

TACCCCGCGACTATGATAATAACGGCTGATCATGATGATCGTGTGGTGCCAATGCATTCG

TATAAAATGATTGCTACTATGCAGCATGTTCTGTGCACAAGCTTAGAGAACAGCCCTCAG

AAGTATCCAATAATTTGTCGCATTCAGCGCAAAGCTTCACATTACGGACGTTCCACAATG

GTTCAGATCGCTGAGGTAGCAGATCGGTATGGCTTTATGGCAAAGGCGCTTAACGCTACT

TGGACAGAC
``` contig c250 predicted polypeptide -(723 aa) (*Dianthus superbus*)
SEQ ID NO: 24

MASCGFTKPLHYPTARRDETVVDDYFGLKVADPYRWLEDRDSEETKKFVEDQVKFTDSVL

EECELIGKVKQKIIDYVSFPRWSVPLRRANKYFHFYNSGLQSQNVYRMQDGLDGKPEVIC

DPNLREDGRTGLSVYSVSEDAKYFAFGIAEGFTEWLTIRVMRTEDRSMLPDCLTEVKFTT

VHWTHDNKGFFYCAYPPLEEGQDHMVHASISQEARYHYLGTDQSEDILCWKDPENPTHHF

RSYFTDDGKYFVLYILEGCDKKNKVYCLDLTKLPNGPESLRGREGSAPFIKLVDSFDASY

-continued

TVIANDDSVFTLLTDKDAKRCKLVRVDLNNPSVWTDVIPESKDLLESAHAVNGNQLLLRY

LRDVKHVLELRDLESGSLLHSIPIDIGAVDGINARRGDSIVFFRFTSILTPGIIYQCDLK

NDPTQLNIFRESLVPGFDRSEFEVKQVFVPGKDGTKIPAFIAARKGISLDGSHPCEMHGY

GGYGHNMMPTFSASRLVFLKHLGGVFCLANIRGGGEYGVDWHKAGARENKQTSFDDFISS

AEFLVSSGYSAPKKICIEGGSNGGLLIAVCITQRPDLFGCAEPNCGPMDMLRFHKFTLGY

LWTDEYGNPDNEEEFNWLIKYSPLHNVRRPWEQPGHEQTQYPATMIITADHDDRVVPMHS

YKMIATMQHVLCTSLENSPQKYPIICRIQRKASHYGRSTMVQIAEVADRYGFMAKALNAT

WTD contig c1141 polynucleotide-(2175 nt) (*Dianthus superbus*)
SEQ ID NO: 25
ATGGCGGTGTCCTGTGGATTCACCAAAACCTTGCATTATCCTCCCGTACGCCGTGACGAA

ACCGTCGTCGACGATTATTTCGGCCTCAAAATCGCCGATCCTTACCGCTGGCTTGAGGAT

CTGAATTCAGAAGAGACAAAGAAATTCGTGGATGATCAAGTGAAGTTTACAGAGTCGGTG

CTTGAAGAATGCGAGTTGATTGGCAAAGTCAAGCAGAAAATCATAGATTATGTCAGTTTT

CCGCGTTGGAGTGTGCCGCTTAGGCGTGCCAACAAATATTTCCACTTCTATAACTCCGGC

CTTCAATCGCAAAATGTGTATCGGATGCAGGATGGTTTGGACGGAAAGCCAGAGGTGGTA

TATGATCCTAACCTTAGAGAAGGGGGAAGAACTGGTTTGACCCTGTATTCTGTAAGCGAG

GATGCCAATTATTTTGCATTTGGTATAGCTGAAGGCTTTACTGAATGGCTCACGATTAGA

GTCATGAGAATTGAAGACCGGAGTATGTTACCGGACTGTATAACCGGGGTGAAACATAGC

GGTATTCACTGGACGCATGACAATAAAGGATTTTTCTATTGCCCATATCCACCCCTCGAG

GAAGGACAAGATCTTATGATTCATCCTAGCATGAGTCAAGAGGTGCGGTATCATTTTATT

GGTACCGACCAGTCTGAAGATATTCTGTGCTGGAAAGATACTGTGAACCCCACTCATCAC

CTCAAGAGCTATTTTACTGATGACGGAAAGTATTTTGTTCTCTACATTTTAGAGGGATGT

AATAACATGAACAAAGTATACTGCTTGGATTTGACAGAGCTGCCAAATGGGCCTGAAAGT

CTCCGTGGGAGAGAAGGCTCAGCGCCTTTCATAAAACTTGTGGATAGTTTTGATGCATTG

TATACAGCCATTGCTAATGATGGTTCTGTGTTTACATTCCTAACTGATAAGGATGCGACG

AGGCGTAAGTTAGTTCGCGTTGATTTGAATAATCCGAGCGTGTGGACTGATGTGCTTCCG

GAGTCCAAGGACTTGCTTGAATCGGCACATGCAGTCAACGGAAACCAGCTTCTTATTCGT

TACCTAAGTGATGTCAAACATATACTAGAGCTTAGGGATCTCGAAAGTGGCTCTCTATTG

CATCGCATACCCATAGACATTGGAGCTGTTGATGGTACTATTAATGCACGACGCGGAGAC

AGTGTCGTGTTTTTCAAGTTTACAAGCATCCTGACTCCTAGCATTATTTATCAATGTGAT

TTGAAAAATGATCCTCCACAATTAAAGATCTTCAGAGAAAGTGTTGTCCCTGGGTTTGAC

CGTTCTGAGTTCGAGGTTAAACAGCTTTTTGCGCCTAGCAAAGATGGCACAATGATACCA

ACATTCGTAGCAGCACGAAAGGGAATTTCTTTGGATGGTTCACACCCATGTGAAATGCAT

GGTTATGGTGCATATGGCCAGTGTATGATGCCAACTTTTTCTGCCAGTCGCTTAGTATTT

TTGAAGCACCTTGGCGGCGTCTTCTGTTTGGCTAATATTCGAGGCGGTGGTGAATATGGA

GTAGAATGGCATAAAGCAGGAGCCCGTGAAAACAAGCAAAACAGTTATGATGACTTCATC

GCCTCAGCTGAGTTCTTGTTTCTAGTGGCTACACCGCACCTAAAAAAATTTGTATCGAA

GGTGGAAGTAACGGGGGCCTTCTCATTGCTGTTTGTATTACTCAGAGACCAGACCTGTTC

GGTTGCGCCGAGCCAAACTGTGGTCCTATGGACATGATTCGATTTCATCATTTTACACAA

GGTTATGTGGTGATGTCGGAATATGGTTCCCCCGACAAAGAGGAAGAGTTCAACTGGCTT

-continued

```
ATCAAGTACTCACCGCTACATAACGTGAGGAGACCATGGGAACAGCCAGGTCATGAACAG

ACGCAATACCCCGCAACTATGATAATAACGGCTGATCATGATGATCGCGTGGTGCCATTT

CATTCGTATAAAATGATAGCTACTATGCAGCATGTTCTGTGCACAAGCTTAGAAAACAGC

CCGCAGAAATTTCCAATAATTTGTCGGATTCAGCGCAACGCTTCACATTATGGACGTGCC

ACAATGGTTCAGATCGCTGAAGTAGCAGATCGGTATGGCTTTATGGCAAAGGCGCTGAAC

GCCACTTGGACAGAC
``` contig c1141 predicted polypeptide-(725 aa) (*Dianthus superbus*)
SEQ ID NO: 26

```
MAVSCGFTKTLHYPPVRRDETVVDDYFGLKIADPYRWLEDLNSEETKKFVDDQVKFTESV

LEECELIGKVKQKIIDYVSFPRWSVPLRRANKYFHFYNSGLQSQNVYRMQDGLDGKPEVV

YDPNLREGGRTGLTLYSVSEDANYFAFGIAEGFTEWLTIRVMRIEDRSMLPDCITGVKHS

GIHWTHDNKGFFYCPYPPLEEGQDLMIHPSMSQEVRYHFIGTDQSEDILCWKDTVNPTHH

LKSYFTDDGKYFVLYILEGCNNMNKVYCLDLTELPNGPESLRGREGSAPFIKLVDSFDAL

YTAIANDGSVFTFLTDKDATRRKLVRVDLNNPSVWTDVLPESKDLLESAHAVNGNQLLIR

YLSDVKHILELRDLESGSLLHRIPIDIGAVDGTINARRGDSVVFFKFTSILTPSIIYQCD

LKNDPPQLKIFRESVVPGFDRSEFEVKQLFAPSKDGTMIPTFVAARKGISLDGSHPCEMH

GYGAYGQCMMPTFSASRLVFLKHLGGVFCLANIRGGGEYGVEWHKAGARENKQNSYDDFI

ASAEFLVSSGYTAPKKICIEGGSNGGLLIAVCITQRPDLFGCAEPNCGPMDMIRFHHFTQ

GYVVMSEYGSPDKEEEFNWLIKYSPLHNVRRPWEQPGHEQTQYPATMIITADHDDRVVPF

HSYKMIATMQHVLCTSLENSPQKFPIICRIQRNASHYGRATMVQIAEVADRYGFMAKALN

ATWTD
```

Segetalin A variant aa1 = A - cyclic polypeptide (6 aa)
SEQ ID NO: 27
AVPVWA

Segetalin A variant aa2 = A - cyclic polypeptide (6 aa)
SEQ ID NO: 28
GAPVWA

Segetalin A variant aa3 = A - cyclic polypeptide (6 aa)
SEQ ID NO: 29
GVAVWA

Segetalin A variant aa4 = A - cyclic polypeptide (6 aa)
SEQ ID NO: 30
GVPAWA

Segetalin A variant aa5 = A - cyclic polypeptide (6 aa)
SEQ ID NO: 31
GVPVAA

Presegetalin A1
SEQ ID NO: 32
AVPVWAFQAKDVENASAPV

Presegetalin A1
SEQ ID NO: 33
GAPVWAFQAKDVENASAPV

Presegetalin A1
SEQ ID NO: 34
GVAVWAFQAKDVENASAPV

Presegetalin A1
SEQ ID NO: 35
GVPAWAFQAKDVENASAPV

Presegetalin A1
SEQ ID NO: 36
GVPVAAFQAKDVENASAPV

-continued

| | |
|---|---|
| Presegetalin A1<br>GVPVWVFQAKDVENASAPV | SEQ ID NO: 37 |
| Presegetalin A1<br>GVPVWAFQAKDVENAPV | SEQ ID NO: 38 |
| Presegetalin A1<br>GVPVWAFQAKDVENA | SEQ ID NO: 39 |
| Presegetalin A1<br>GVPVWAFQAKD | SEQ ID NO: 40 |
| Presegetalin A1<br>GVPVWAF | SEQ ID NO: 41 |
| Presegetalin A1<br>GVPVWA | SEQ ID NO: 42 |
| Presegetalin A1<br>GVPVWAAQAKDVENASAPV | SEQ ID NO: 43 |
| Presegetalin A1<br>GVPVWAFAAKDVENASAPV | SEQ ID NO: 44 |
| Presegetalin A1<br>GVPVWAFQVKDVENASAPV | SEQ ID NO: 45 |
| Presegetalin A1<br>GVPVWAFQAADVENASAPV | SEQ ID NO: 46 |
| Presegetalin A1<br>GVPVWAFQAKAVENASAPV | SEQ ID NO: 47 |
| Presegetalin A1<br>GVPVWAFQAKDAENASAPV | SEQ ID NO: 48 |
| Presegetalin A1<br>GVPVWAFQAKDVANASAPV | SEQ ID NO: 49 |
| Presegetalin A1<br>GVPVWAFQAKDVEAASAPV | SEQ ID NO: 50 |
| Presegetalin A1<br>GVPVWAFQAKDVENVSAPV | SEQ ID NO: 51 |
| Presegetalin A1<br>GVPVWAFQAKDVENAAPV | SEQ ID NO: 52 |
| Presegetalin A1<br>GVPVWAFQAKDVENASVPV | SEQ ID NO: 53 |
| Presegetalin A1<br>GVPVWAFQAKDVENASAAV | SEQ ID NO: 54 |
| Presegetalin A1<br>GVPVWAFQAKDVENASAPA | SEQ ID NO: 55 |
| Presegetalin A1<br>GvPVWAFQAKDVENASAPV | SEQ ID NO: 56 |

-continued

| Presegetalin A1 | |
|---|---|
| GVpVWAFQAKDVENASAPV | SEQ ID NO: 57 |

| Presegetalin A1 | |
|---|---|
| GVPvWAFQAKDVENASAPV | SEQ ID NO: 58 |

| Presegetalin A1 | |
|---|---|
| GVPVwAFQAKDVENASAPV | SEQ ID NO: 59 |

| Presegetalin A1 | |
|---|---|
| GVPVWAAFQAKDVENASAPV | SEQ ID NO: 60 |

| Presegetalin A1 | |
|---|---|
| GVpVAAFQAKDVENASAPV | SEQ ID NO: 61 |

| Presegetalin A1 | |
|---|---|
| GVpVaAFQAKDVENASAPV | SEQ ID NO: 62 |

| Presegetalin A1 | |
|---|---|
| GVPAVWAFQAKDVENASAPV | SEQ ID NO: 63 |

| Presegetalin A1 | |
|---|---|
| GVPAAAVWAFQAKDVENASAPV | SEQ ID NO: 64 |

| Presegetalin B1 | |
|---|---|
| GVAWAFQAKDVENASAPV | SEQ ID NO: 65 |

| Presegetalin D1 | |
|---|---|
| GLSFAFPAKDAENASSPV | SEQ ID NO: 66 |

| Presegetalin D1 | |
|---|---|
| GLSFAFQAKDAENASSPV | SEQ ID NO: 67 |

| Presegetalin G1 | |
|---|---|
| GVKYAFQPKDSENASAPV | SEQ ID NO: 68 |

| Presegetalin H1 | |
|---|---|
| GYRFSFQAKDAENASAPV | SEQ ID NO: 69 |

| Presegetalin L1 | |
|---|---|
| GLPGWPFQAKDVENASAPV | SEQ ID NO: 70 |

| Presegetalin F1 | |
|---|---|
| FSASYSSKPIQTQVSNGMDNASAPV | SEQ ID NO: 71 |

| Presegetalin J1 | |
|---|---|
| FGTHGLPAPIQVPNGMDDACAPM | SEQ ID NO: 72 |

| *Dianthus* Precursor A | |
|---|---|
| GPIPFYGFQAKDAENASVPV | SEQ ID NO: 73 |

| *Dianthus* Precursor B | |
|---|---|
| GYKDCCVQAKDLENAAVPV | SEQ ID NO: 74 |

| Stelladein A-cyclic polypeptide (11 aa) | |
|---|---|
| PPPLLGPPYYG | SEQ ID NO: 75 |

```
-continued
Segetalin A ins 3A4-cyclic polypeptide (7 aa)
                                                    SEQ ID NO: 76
GVPAVWA Cyclization product of presegetalin D1
                                                    SEQ ID NO: 77
GLSFA
```

REFERENCES

The Contents of the Entirety of Each of which are Incorporated by this Reference.

Alvarez J P, Pekker I, Goldshmidt A, Blum E, Amsellem Z, Eshed Y. (2006) Endogenous and synthetic microRNAs stimulate simultaneous, efficient, and localized regulation of multiple targets in diverse species. Plant Cell. 8, 1134-51.

Austin J, Wang W, Puttamadappa S, Shekhtman A, Camarero J A. (2009) Chembiochem. 10:2663-2670.

Bechtold N, Ellis J, Pellefer G. (1993) In planta Agrobacterium-mediated gene transfer by infiltration of adult Arabidopsis thaliana plants. C. R. Acad. Sci. Ser. III Sci. Vie, 316: 1194-1199.

Becker D, Brettschneider R, Lorz H. (1994) Fertile transgenic wheat from microprojectile bombardment of scutellar tissue. Plant J. 5: 299-307.

Bolscher J G, Oudhoff M J, Nazmi K, Antos J M, Guimaraes C P, Spooner E, Haney E F, Garcia Vallejo J J, Vogel H J, Van't Hof W, Ploegh H L, Veerman E C. (2011) Sortase A as a tool for high-yield histatin cyclization. FASEB J. 25(8), 2650-2658.

Camarero J A. (2010) Combinatorial approaches and conditional protein splicing methods for rapid biosynthesis and in vivo screening of biologically relevant peptides. International Patent Publication WO 2011-005598 published Jan. 13, 2011. Cascales L, Craik D J. (2010) Org. Biomol. Chem. 8, 5035-5047.

Chevreux B, Pfisterer T, Drescher B, Driesel A J, Muller W E, Wetter T, Suhai S. (2004) Genome Res. 14, 1147-1159.

Condie J A, Nowak G, Reed D W, Balsevich J J, Reaney M J, Arnison P G, Covello P S. The biosynthesis of Caryophyllaceae-like cyclic peptides in Saponaria vaccaria L. from DNA-encoded precursors. (2011) Plant J. 67, 682-690.

Covello P S, Datla R S S, Stone S L, Balsevich J J, Reaney M J, Arnison P G, Condie J A. (2010) Genes encoding linear precursors of cyclic peptides of Caryophyllaceae and their use in the manufacture of cyclic peptides and their analogs. International Patent Publication WO 2010-130030 published Nov. 18, 2010.

Craik D J, Cemazar M, Daly N L. (2007) Curr. Opin. Drug Discov. Devel. 10, 176-184.

Datla R, Anderson J W, Selvaraj G. (1997) Plant promoters for transgene expression. Biotechnology Annual Review. 3: 269-296.

Davies J S. (2003) J. Pept. Sci. 9, 471-501.

DeBlock M, DeBrouwer D, Tenning P. (1989) Transformation of Brassica napus and Brassica oleracea using Agrobacterium tumefaciens and the expression of the bar and neo genes in the transgenic plants. Plant Physiol. 91: 694-701.

Depicker A, Montagu M V. (1997) Post-transcriptional gene silencing in plants. Curr Opin Cell Biol. 9, 373-82.

Donia M S, Ravel J, Schmidt E W. (2008) Nat. Chem. Biol. 4, 341-343.

Fulop V, Bocskei Z, Polgar L. (1998). Prolyl Oligopeptidase: An Unusual b-Propeller Domain Regulates Proteolysis. Cell. 94, 161-170.

Gaasterland T, Sensen C W. (1996) Biochimie. 78, 302-310.

Gambino G, Perrone I, Gribaudo I. (2008) Phytochem Anal. 19, 520-525.

GenBank Accession No. CAN70125. (2008) Hypothetical protein VITISV_001107 [Vitis vinifera].

GenBank Accession No. XP_002890385. (2010) Hypothetical protein ARALYDRAFT_472267 [Arabidopsis lyrata subsp. lyrata].

Ghadiri R M, Granja J R, Milligan R A, McRee D E, Khazanovich N. (1993) Self-assembling organic nanotubes based on a cyclic peptide architecture. Nature. 366, 324-327.

Grunewald J, Marahiel M A. (2006) Microbiol. Mol. Biol. Rev. 70, 121-146.

Helliwell C A, Waterhouse P M. (2005) Constructs and methods for hairpin RNA-mediated gene silencing in plants. Methods Enzymology. 392, 24-35.

Henikoff S, Till B J, Comai L. (2004) TILLING. Traditional mutagenesis meets functional genomics. Plant Physiol. 135, 630-6.

Hourani R, Zhang C, van der Weegen R, Ruiz L, Li C, Keten S, Helms B A, Xu T. (2011) Processable cyclic peptide nanotubes with tunable interiors. J Am Chem. Soc. 133 (39), 15296-9.

Katavic Y, Haughn G W, Reed D, Martin M, Kunst L. (1994) In planta transformation of Arabidopsis thaliana. Mol. Gen. Genet. 245: 363-370.

Katoh T, Goto Y, Reza M S, Suga H. (2011) Chem. Commun. (Camb.) 47, 9946-9958.

Kohli R M, Trauger J W, Schwarzer D, Marahiel M A., Walsh C T. (2001) Biochemistry. 40, 7099-7108.

Lambert J N, Mitchell J P, Roberts K D. (2001) J. Chem. Soc, Perkin Trans. 1 471-484.

Li X, Song Y, Century K, Straight S, Ronald P, Dong X, Lassner M, Zhang Y. (2001) A fast neutron deletion mutagenesis-based reverse genetics system for plants. Plant J. 27, 235-242.

McIntosh J A, Robertson C R, Agarwal V, Nair S K, Bulaj G W, Schmidt E W. (2010) J. Am. Chem. Soc. 132, 15499-15501.

Meyer P. (1995) Understanding and controlling transgene expression. Trends in Biotechnology. 13: 332-337.

Moloney M M, Walker J M, Sharma K K. (1989) High efficiency transformation of Brassica napus using Agrobacterium vectors. Plant Cell Rep. 8: 238-242.

Morita H, Yun Y S, Takeya K, Itokawa H. (1994) Tetrahedron Lett. 51, 9593-9596.

Morita H, Takeya K. (2010) Heterocycles. 80, 739-764.

Neddleman and Wunsch. (1970) J. Mol. Biol. 48: 443.

Nehra N S, Chibbar R N, Leung N, Caswell K, Mallard C, Steinhauer L, Baga M, Kartha K K. (1994) Self-fertile transgenic wheat plants regenerated from isolated scutellar tissues following microprojectile bombardment with two distinct gene constructs. Plant J. 5: 285-297. Pearson and Lipman. (1988) Proc. Natl. Acad. Sci. (U.S.A.) 85: 2444.

Pomilio A B, Battista M E, Vitale A A. (2006) Curr. Org. Chem. 10, 2075-2121.

Potrykus L. (1991) Gene transfer to plants: Assessment of publish approaches and results. Annu. Rev. Plant Physiol. Plant Mol. Biol. 42: 205-225.

Rappsilber J, Ishihama Y, Mann M. (2003) *Anal. Chem.* 75, 663-670.

Rhodes C A, Pierce D A, Mettler I J, Mascarenhas D, Detmer J J. (1988) Genetically transformed maize plants from protoplasts. *Science.* 240: 204-207.

Sambrook J, Fritsch E F, Maniatis T. (2001) *Molecular Cloning: A Laboratory Manual 3$^{rd}$ edn.* Cold Spring Harbor: Cold Spring Harbor Laboratory Press.

Sanford J C, Klein T M, Wolf E D, Allen N. (1987) Delivery of substances into cells and tissues using a particle bombardment process. *J. Part. Sci. Technol.* 5: 27-37.

Schmidt E W, Hathaway B, Nelson J T. (2007) Methods and Compositions Related to Cyclic Peptide Synthesis. International Patent Publication WO 2007-103739 published Sep. 13, 2007.

Schmidt E W, Hathaway B, Nelson J T, Donia M S. (2010) Methods and Compositions Related to Cyclic Peptide Synthesis. United States Patent Publication US 2010-209414 published Aug. 19, 2010.

Schwab R, Ossowski S, Riester M, Warthmann N, Weigel D. (2006) Highly specific gene silencing by artificial microRNAs in *Arabidopsis. Plant Cell* 18, 1121-33.

Sheoran I S, Olson D J, Ross A R, Sawhney V K. (2005) *Proteomics.* 5, 3752-3764.

Shimamoto K, Terada R, Izawa T, Fujimoto H. (1989) Fertile transgenic rice plants regenerated from transformed protoplasts. *Nature.* 335: 274-276.

Smith and Waterman. (1981) *Ad. App. Math.* 2: 482.

Songstad D D, Somers D A, Griesbach R J. (1995) Advances in alternative DNA delivery techniques. *Plant Cell, Tissue and Organ Culture.* 40:1-15.

Stam M, de Bruin R, van Blokland R, van der Hoorn R A, Mol J N, Kooter J M. (2000) Distinct features of post-transcriptional gene silencing by antisense transgenes in single copy and inverted T-DNA repeat loci. *Plant J.* 21, 27-42.

Studier F W. (2005) *Protein Expr. Purif.* 41, 207-234.

Tan N H, Zhou J. (2006) Plant cyclopeptides. *Chem. Rev.* 106, 840-895.

Tang G, Jian X, Pan H. (2011) Sequence of *Streptomyces nobilis* gene cluster for biosynthesis of cyclopeptide YN-216391. Chinese Patent Publication CN 102174530 published Sep. 7, 2011-Abstract.

Thongyoo P, Roque-Rosell N, Leatherbarrow R J, Tate E W. (2008) *Org. Biomol. Chem.* 6, 1462-1470.

Vasil I K. (1994) Molecular improvement of cereals. *Plant Mol. Biol.* 5: 925-937.

Walden R, Wingender R. (1995) Gene-transfer and plant regeneration techniques. *Trends in Biotechnology.* 13: 324-331.

White C J, Yudin A K. (2011) *Nat. Chem.* 3, 509-524.

Wu Z, Guo X, Guo Z. (2011) *Chem. Commun.* (Camb.) 47, 9218-9220.

Young T S, Young D D, Ahmad I, Louis J M, Benkovic S J, Schultz P G. (2011) *Proc. Natl. Acad. Sci. U.S.A.* 108, 11052-11056.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. An recombinant polypeptide comprising an amino acid sequence having at least 95% sequence identity to the amino acid sequence as set forth in SEQ ID NO: 2 and has a function of peptide cyclization, wherein the recombinant polypeptide is recombinantly expressed in a microorganism.

2. The recombinant polypeptide according to claim 1, wherein the amino acid sequence has at least 99% sequence identity to the amino acid sequence as set forth in SEQ ID NO: 2.

3. The recombinant polypeptide according to claim 1, wherein the amino acid sequence is as set forth in SEQ ID NO: 2.

4. A process of producing a cyclic peptide, the process comprising contacting a suitable linear peptide precursor of the cyclic peptide with the polypeptide of claim 1 to produce the cyclic peptide from the linear peptide precursor.

5. The process according to claim 1, wherein the amino acid sequence is as set forth in SEQ ID NO: 2.

6. The process according to claim 4, wherein the linear peptide precursor is provided to a microbial host cell transformed or transfected with a nucleic acid molecule encoding the recombinant polypeptide according to claim 1.

7. The process according to claim 4, wherein the cyclic peptide is segetalin A.

8. The process according to claim 4, wherein the cyclic peptide comprises the amino acid sequence as set forth in SEQ ID NO: 77.

9. The process according to claim 4, wherein the linear peptide precursor is produced by a recombinant organism.

* * * * *